United States Patent
Heller et al.

(10) Patent No.: US 6,284,478 B1
(45) Date of Patent: *Sep. 4, 2001

(54) SUBCUTANEOUS GLUCOSE ELECTRODE

(75) Inventors: Adam Heller; Michael V. Pishko, both of Austin, TX (US)

(73) Assignee: E. Heller & Company, Alameda, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/767,110

(22) Filed: Dec. 4, 1996

Related U.S. Application Data

(63) Continuation of application No. 08/299,526, filed on Sep. 1, 1994, now Pat. No. 5,593,852, which is a continuation-in-part of application No. 08/161,682, filed on Dec. 2, 1993, now Pat. No. 5,356,786.

(51) Int. Cl.[7] .............................. C12Q 1/54; C12Q 1/00; C12Q 1/26; C12Q 1/28
(52) U.S. Cl. ................................. 435/14; 435/4; 435/25; 435/28; 435/817; 435/287; 436/63; 436/149; 204/403
(58) Field of Search ................................. 435/4, 14, 25, 435/28, 817, 287; 436/63, 149; 204/403

(56) References Cited

U.S. PATENT DOCUMENTS

| | | | |
|---|---|---|---|
| Re. 32,947 | 6/1989 | Dormer et al. | 435/14 |
| 3,260,656 | 7/1966 | Ross, Jr. | 435/14 |
| 3,653,841 | 4/1972 | Klein | 435/14 |
| 3,719,564 | 3/1973 | Lilly, Jr. et al. | 435/14 |
| 3,776,832 | 12/1973 | Oswin et al. | 435/14 |
| 3,837,339 | 9/1974 | Aisenberg et al. | 435/14 |
| 3,926,760 | 12/1975 | Allen et al. | 435/14 |
| 3,972,320 | 8/1976 | Kalman | 435/14 |
| 3,979,274 | 9/1976 | Newman | 435/14 |
| 4,008,717 | 2/1977 | Kowarski | 435/14 |

(List continued on next page.)

FOREIGN PATENT DOCUMENTS

| | | |
|---|---|---|
| 227 029 A3 | 9/1985 | (DD) . |
| 29 03 216 | 8/1979 | (DE) . |
| 3934299 | 10/1990 | (DE) . |
| 44 01 400 A1 | 7/1995 | (DE) . |
| 0 010 375 A1 | 4/1980 | (EP) . |

(List continued on next page.)

OTHER PUBLICATIONS

Abruña, H. D. et al., "Rectifying Interfaces Using Two–Layer Films of Electrochemically Polymerized Vinylpyridine and Vinylbipyridine Complexes of Ruthenium and Iron on Electrodes," *J. Am. Chem. Soc.*, 103(1):1–5 (Jan. 14, 1981).

Albery, W. J. et al., "Amperometric enzyme electrodes. Part II. Conducting salts as electrode materials for the oxidation of glucose oxidase," *J. Electroanal. Chem. Interfacial Electrochem.*, 194(2)(1 page–13 Abstract only)(1985).

(List continued on next page.)

*Primary Examiner*—Louise N. Leary
(74) *Attorney, Agent, or Firm*—Merchant & Gould P.C.

(57) ABSTRACT

A small diameter flexible electrode designed for subcutaneous in vivo amperometric monitoring of glucose is described. The electrode is designed to allow "one-point" in vivo calibration, i.e., to have zero output current at zero glucose concentration, even in the presence of other electroreactive species of serum or blood. The electrode is preferably three or four-layered, with the layers serially deposited within a recess upon the tip of a polyamide insulated gold wire. A first glucose concentration-to-current transducing layer is overcoated with an electrically insulating and glucose flux limiting layer (second layer) on which, optionally, an immobilized interference-eliminating horseradish peroxidase based film is deposited (third layer). An outer (fourth) layer is biocompatible.

74 Claims, 10 Drawing Sheets

U.S. PATENT DOCUMENTS

| | | | |
|---|---|---|---|
| 4,016,866 | 4/1977 | Lawton | 435/14 |
| 4,055,175 | 10/1977 | Clemens et al. | 435/14 |
| 4,059,406 | 11/1977 | Fleet | 435/14 |
| 4,076,596 | 2/1978 | Connery et al. | 435/14 |
| 4,098,574 | 7/1978 | Dappen | 435/14 |
| 4,100,048 | 7/1978 | Pompei et al. | 435/14 |
| 4,151,845 | 5/1979 | Clemens | 435/14 |
| 4,168,205 | 9/1979 | Danninger et al. | 435/14 |
| 4,172,770 | 10/1979 | Semersky et al. | 435/14 |
| 4,178,916 | 12/1979 | McNamara | 435/14 |
| 4,206,755 | 6/1980 | Klein | 435/14 |
| 4,224,125 | 9/1980 | Nakamura et al. | 435/14 |
| 4,240,438 | 12/1980 | Updike et al. | 435/14 |
| 4,247,297 | 1/1981 | Berti et al. | 435/14 |
| 4,340,458 | 7/1982 | Lerner et al. | 435/14 |
| 4,352,960 | 10/1982 | Dormer et al. | 435/14 |
| 4,356,074 | 10/1982 | Johnson | 435/14 |
| 4,365,637 | 12/1982 | Johnson | 435/14 |
| 4,366,033 | 12/1982 | Richter et al. | 435/14 |
| 4,375,399 | 3/1983 | Havas et al. | 435/14 |
| 4,384,586 | 5/1983 | Christiansen | 435/14 |
| 4,390,621 | 6/1983 | Bauer | 435/14 |
| 4,401,122 | 8/1983 | Clark, Jr. | 435/14 |
| 4,404,066 | 9/1983 | Johnson | 435/14 |
| 4,418,148 | 11/1983 | Oberhardt | 435/14 |
| 4,427,770 | 1/1984 | Chen et al. | 435/14 |
| 4,431,004 | 2/1984 | Bessman et al. | 435/14 |
| 4,436,094 | 3/1984 | Cerami | 435/14 |
| 4,440,175 | 4/1984 | Wilkins | 435/14 |
| 4,450,842 | 5/1984 | Zick et al. | 435/14 |
| 4,458,686 | 7/1984 | Clark, Jr. | 435/14 |
| 4,461,691 | 7/1984 | Frank | 435/14 |
| 4,469,110 | 9/1984 | Slama | 435/14 |
| 4,477,314 | 10/1984 | Richter et al. | 435/14 |
| 4,484,987 | 11/1984 | Gough | 435/14 |
| 4,522,690 | 6/1985 | Venkatasetty | 435/14 |
| 4,524,114 | 6/1985 | Samuels et al. | 435/14 |
| 4,526,661 | 7/1985 | Steckhan et al. | 435/14 |
| 4,534,356 | 8/1985 | Papadakis | 435/14 |
| 4,538,616 | 9/1985 | Rogoff | 435/14 |
| 4,543,955 | 10/1985 | Schroeppel | 435/14 |
| 4,545,382 | 10/1985 | Higgins et al. | 435/14 |
| 4,552,840 | 11/1985 | Riffer | 435/14 |
| 4,560,534 | 12/1985 | Kung et al. | 435/14 |
| 4,571,292 | 2/1986 | Liu et al. | 435/14 |
| 4,573,994 | 3/1986 | Fischell et al. | 435/14 |
| 4,581,336 | 4/1986 | Malloy et al. | 435/14 |
| 4,595,011 | 6/1986 | Phillips | 435/14 |
| 4,619,754 | 10/1986 | Niki et al. | 435/14 |
| 4,627,445 | 12/1986 | Garcia et al. | 435/14 |
| 4,627,908 | 12/1986 | Miller | 435/14 |
| 4,633,878 | 1/1987 | Bombardieri | 435/14 |
| 4,637,403 | 1/1987 | Garcia et al. | 435/14 |
| 4,650,547 | 3/1987 | Gough | 435/14 |
| 4,654,197 | 3/1987 | Lilja et al. | 435/14 |
| 4,655,880 | 4/1987 | Liu | 435/14 |
| 4,655,885 | 4/1987 | Hill et al. | 435/14 |
| 4,671,288 | 6/1987 | Gough | 435/14 |
| 4,679,562 | 7/1987 | Luksha | 435/14 |
| 4,680,268 | 7/1987 | Clark, Jr. | 435/14 |
| 4,682,602 | 7/1987 | Prohaska | 435/14 |
| 4,684,537 | 8/1987 | Graetzel et al. | 435/14 |
| 4,685,463 | 8/1987 | Williams | 435/14 |
| 4,703,756 | 11/1987 | Gough et al. | 435/14 |
| 4,711,245 | 12/1987 | Higgins et al. | 435/14 |
| 4,717,673 | 1/1988 | Wrighton et al. | 435/14 |
| 4,721,601 | 1/1988 | Wrighton et al. | 435/14 |
| 4,721,677 | 1/1988 | Clark, Jr. | 435/14 |
| 4,726,378 | 2/1988 | Kaplan | 435/14 |
| 4,726,716 | 2/1988 | McGuire | 435/14 |
| 4,757,022 | 7/1988 | Shults et al. | 435/14 |
| 4,758,323 | 7/1988 | Davis et al. | 435/14 |
| 4,759,371 | 7/1988 | Franetzki | 435/14 |
| 4,759,828 | 7/1988 | Young et al. | 435/14 |
| 4,764,416 | 8/1988 | Ueyama et al. | 435/14 |
| 4,776,944 | 10/1988 | Janata et al. | 435/14 |
| 4,777,953 | 10/1988 | Ash et al. | 435/4 |
| 4,781,798 | 11/1988 | Gough | 435/14 |
| 4,784,736 | 11/1988 | Lonsdale et al. | 435/14 |
| 4,795,707 | 1/1989 | Niiyama et al. | 435/14 |
| 4,796,634 | 1/1989 | Huntsman et al. | 435/14 |
| 4,805,624 | 2/1989 | Yao et al. | 435/14 |
| 4,813,424 | 3/1989 | Wilkins | 435/14 |
| 4,815,469 | 3/1989 | Cohen et al. | 435/14 |
| 4,820,399 | 4/1989 | Senda et al. | 435/14 |
| 4,822,337 | 4/1989 | Newhouse et al. | 435/14 |
| 4,830,959 | 5/1989 | McNeil et al. | 435/14 |
| 4,832,797 | 5/1989 | Vadgama et al. | 435/14 |
| 4,840,893 | 6/1989 | Hill et al. | 435/14 |
| 4,848,351 | 7/1989 | Finch | 435/14 |
| 4,854,322 | 8/1989 | Ash et al | 435/4 |
| 4,871,351 | 10/1989 | Feingold | 435/14 |
| 4,871,440 | 10/1989 | Nagata et al. | 435/14 |
| 4,874,500 | 10/1989 | Madou et al. | 435/14 |
| 4,890,620 | 1/1990 | Gough | 435/14 |
| 4,894,137 | 1/1990 | Takizawa et al. | 435/14 |
| 4,897,162 | 1/1990 | Lewandowski et al. | 435/14 |
| 4,897,173 | 1/1990 | Nankai et al. | 435/14 |
| 4,909,908 | 3/1990 | Ross et al. | 435/14 |
| 4,911,794 | 3/1990 | Parce et al. | 435/14 |
| 4,917,800 | 4/1990 | Lonsdale et al. | 435/14 |
| 4,919,141 | 4/1990 | Zier et al. | 435/14 |
| 4,919,767 | 4/1990 | Vadgama et al. | 435/14 |
| 4,923,586 | 5/1990 | Katayama et al. | 435/14 |
| 4,927,516 | 5/1990 | Yamaguchi et al. | 435/14 |
| 4,934,369 | 6/1990 | Maxwell | 435/14 |
| 4,935,105 | 6/1990 | Churchouse | 435/14 |
| 4,935,345 | 6/1990 | Guilbeau et al. | 435/14 |
| 4,938,860 | 7/1990 | Wogoman | 435/14 |
| 4,944,299 | 7/1990 | Silvian | 435/14 |
| 4,950,378 | 8/1990 | Nagata | 435/14 |
| 4,953,552 | 9/1990 | DeMarzo | 435/14 |
| 4,954,129 | 9/1990 | Giuliani et al. | 435/14 |
| 4,969,468 | 11/1990 | Byers et al. | 435/14 |
| 4,970,145 | 11/1990 | Bennetto et al. | 435/14 |
| 4,974,929 | 12/1990 | Curry | 435/14 |
| 4,986,271 | 1/1991 | Wilkins | 435/14 |
| 4,994,167 | 2/1991 | Shults et al. | 435/14 |
| 5,001,054 | 3/1991 | Wagner | 435/14 |
| 5,002,054 | 3/1991 | Ash et al. | 435/4 |
| 5,058,592 | 10/1991 | Whisler | 435/14 |
| 5,070,535 | 12/1991 | Hochmair et al. | 435/14 |
| 5,082,550 | 1/1992 | Rishpon et al. | 435/14 |
| 5,082,786 | 1/1992 | Nakamoto | 435/14 |
| 5,089,112 | 2/1992 | Skotheim et al. | 435/14 |
| 5,095,904 | 3/1992 | Seligman et al. | 435/14 |
| 5,101,814 | 4/1992 | Palti | 435/14 |
| 5,106,365 | 4/1992 | Hernandez | 435/4 |
| 5,108,564 | 4/1992 | Szuminsky et al. | 435/14 |
| 5,109,850 | 5/1992 | Blanco et al. | 435/14 |
| 5,120,420 | 6/1992 | Nankai et al. | 435/14 |
| 5,126,034 | 6/1992 | Carter et al. | 435/14 |
| 5,133,856 | 7/1992 | Yamaguchi et al. | 435/14 |
| 5,135,003 | 8/1992 | Souma | 435/14 |
| 5,141,868 | 8/1992 | Shanks et al. | 435/14 |
| 5,161,532 | 11/1992 | Joseph | 435/14 |
| 5,165,407 | 11/1992 | Wilson et al. | 435/14 |
| 5,174,291 | 12/1992 | Schoonen et al. | 435/14 |
| 5,190,041 | 3/1993 | Palti | 435/14 |
| 5,192,416 | 3/1993 | Wang et al. | 435/14 |
| 5,198,367 | 3/1993 | Aizawa et al. | 435/14 |
| 5,202,261 | 4/1993 | Musho et al. | 435/14 |

| | | | | | | |
|---|---|---|---|---|---|---|
| 5,205,920 | 4/1993 | Oyama et al. | 435/14 | 0 127 958 A2 | 12/1984 | (EP) . |
| 5,208,154 | 5/1993 | Weaver et al. | 435/14 | 0 136 362 A1 | 4/1985 | (EP) . |
| 5,209,229 | 5/1993 | Gilli | 435/14 | 0 170 375 A2 | 2/1986 | (EP) . |
| 5,217,595 | 6/1993 | Smith et al. | 435/14 | 0 177 743 A2 | 4/1986 | (EP) . |
| 5,229,282 | 7/1993 | Yoshioka et al. | 435/14 | 0 080 304 B1 | 5/1986 | (EP) . |
| 5,250,439 | 10/1993 | Musho et al. | 435/14 | 0 184 909 A2 | 6/1986 | (EP) . |
| 5,262,035 | 11/1993 | Gregg et al. | 435/14 | 0 206 218 A2 | 12/1986 | (EP) . |
| 5,262,305 | 11/1993 | Heller et al. | 435/14 | 0 230 472 A1 | 8/1987 | (EP) . |
| 5,264,103 | 11/1993 | Yoshioka et al. | 435/14 | 0 241 309 A3 | 10/1987 | (EP) . |
| 5,264,104 | 11/1993 | Gregg et al. | 435/14 | 0 245 073 A2 | 11/1987 | (EP) . |
| 5,264,106 | 11/1993 | McAleer et al. | 435/14 | 0 278 647 A2 | 8/1988 | (EP) . |
| 5,271,815 | 12/1993 | Wong | 435/14 | 0 359 831 A1 | 3/1990 | (EP) . |
| 5,279,294 | 1/1994 | Anderson et al. | 435/14 | 0 368 209 A1 | 5/1990 | (EP) . |
| 5,286,362 | 2/1994 | Hoenes et al. | 435/14 | 0 390 390 A1 | 10/1990 | (EP) . |
| 5,286,364 | 2/1994 | Yacynych et al. | 435/14 | 0 400 918 A1 | 12/1990 | (EP) . |
| 5,288,636 | 2/1994 | Pollmann et al. | 435/14 | 0 453 283 A1 | 10/1991 | (EP) . |
| 5,293,546 | 3/1994 | Tadros et al. | 435/14 | 0 470 290 A1 | 2/1992 | (EP) . |
| 5,320,098 | 6/1994 | Davidson | 435/14 | 0 127 958 B2 | 3/1992 | (EP) . |
| 5,320,725 | 6/1994 | Gregg et al. | 435/14 | 0 255 291 B1 | 6/1992 | (EP) . |
| 5,322,063 | 6/1994 | Allen et al. | 435/14 | 1394171 | 5/1975 | (GB) . |
| 5,337,747 | 8/1994 | Neftel | 435/14 | 1599241 | 9/1981 | (GB) . |
| 5,352,348 | 10/1994 | Young et al. | 435/14 | 2 073 891 | 10/1981 | (GB) . |
| 5,356,786 | 10/1994 | Heller et al. | 435/14 | 2 154 003 | 2/1988 | (GB) . |
| 5,368,028 | 11/1994 | Palti | 435/14 | 2 204 408 | 11/1988 | (GB) . |
| 5,372,133 | 12/1994 | Hogen Esch | 435/14 | 2 254 436 | 10/1992 | (GB) . |
| 5,376,251 | 12/1994 | Kaneko et al. | 435/14 | 54-41191 | 4/1979 | (JP) . |
| 5,378,628 | 1/1995 | Grätzel et al. | 435/14 | 55-10581 | 1/1980 | (JP) . |
| 5,387,327 | 2/1995 | Khan | 435/14 | 55-10583 | 1/1980 | (JP) . |
| 5,390,671 | 2/1995 | Lord et al. | 435/14 | 55-10584 | 1/1980 | (JP) . |
| 5,391,250 | 2/1995 | Cheney, II et al. | 435/14 | 55-12406 | 1/1980 | (JP) . |
| 5,395,504 | 3/1995 | Saurer et al. | 435/14 | 56-163447 | 12/1981 | (JP) . |
| 5,411,647 | 5/1995 | Johnson et al. | 435/14 | 57-70448 | 4/1982 | (JP) . |
| 5,437,999 | 8/1995 | Diebold et al. | 435/14 | 60-173457 | 9/1985 | (JP) . |
| 5,462,645 | 10/1995 | Albery et al. | 435/4 | 60-173458 | 9/1985 | (JP) . |
| 5,469,846 | 11/1995 | Khan | 435/14 | 60-173459 | 9/1985 | (JP) . |
| 5,494,562 | 2/1996 | Maley et al. | 435/14 | 61-90050 | 5/1986 | (JP) . |
| 5,496,453 | 3/1996 | Uenoyama et al. | 435/14 | 62-85855 | 4/1987 | (JP) . |
| 5,497,772 | 3/1996 | Schulman et al. | 435/14 | 62-114747 | 5/1987 | (JP) . |
| 5,531,878 | 7/1996 | Vadgama et al. | 435/14 | 63-58149 | 3/1988 | (JP) . |
| 5,545,191 | 8/1996 | Mann et al. | 435/14 | 63-128252 | 5/1988 | (JP) . |
| 5,560,357 | 10/1996 | Faupel et al. | 435/14 | 63-139246 | 6/1988 | (JP) . |
| 5,565,085 | 10/1996 | Ikeda et al. | 435/14 | 63-294799 | 12/1988 | (JP) . |
| 5,567,302 | 10/1996 | Song et al. | 435/14 | 63-317757 | 12/1988 | (JP) . |
| 5,568,806 | 10/1996 | Cheney, II et al. | 435/14 | 63-317758 | 12/1988 | (JP) . |
| 5,569,186 | 10/1996 | Lord et al. | 435/14 | 1-114746 | 5/1989 | (JP) . |
| 5,582,184 | 12/1996 | Erickson et al. | 435/14 | 1-114747 | 5/1989 | (JP) . |
| 5,582,697 | 12/1996 | Ikeda et al. | 435/14 | 1-124060 | 5/1989 | (JP) . |
| 5,582,698 | 12/1996 | Flaherty et al. | 435/14 | 1-134244 | 5/1989 | (JP) . |
| 5,586,553 | 12/1996 | Halili et al. | 435/14 | 1-156658 | 6/1989 | (JP) . |
| 5,589,326 | 12/1996 | Deng et al. | 435/14 | 2-62958 | 3/1990 | (JP) . |
| 5,593,852 | 1/1997 | Heller et al. | 435/14 | 2-120655 | 5/1990 | (JP) . |
| 5,596,150 | 1/1997 | Arndt et al. | 435/14 | 2-287145 | 11/1990 | (JP) . |
| 5,617,851 | 4/1997 | Lipkovker | 435/14 | 2-310457 | 12/1990 | (JP) . |
| 5,628,890 | 5/1997 | Carter et al. | 435/14 | 3-26956 | 2/1991 | (JP) . |
| 5,651,869 | 7/1997 | Yoshioka et al. | 435/14 | 3-28752 | 2/1991 | (JP) . |
| 5,660,163 | 8/1997 | Schulman et al. | 435/14 | 3-202764 | 9/1991 | (JP) . |
| 5,670,031 | 9/1997 | Hintsche et al. | 435/14 | 5-72171 | 3/1993 | (JP) . |
| 5,680,858 | 10/1997 | Hansen et al. | 435/14 | 5-196595 | 8/1993 | (JP) . |
| 5,682,233 | 10/1997 | Brinda | 435/14 | 7-72585 | 3/1995 | (JP) . |
| 5,695,623 | 12/1997 | Michel et al. | 435/14 | 1281988 A1 | 1/1987 | (SU) . |
| 5,708,247 | 1/1998 | McAleer et al. | 435/14 | WO 85/05119 | 11/1985 | (WO) . |
| 5,711,861 | 1/1998 | Ward et al. | 435/14 | 89/08713 | 9/1989 | (WO) . |
| 5,711,862 | 1/1998 | Sakoda et al. | 435/14 | 90/05300 | 5/1990 | (WO) . |
| 5,741,211 | 4/1998 | Renirie et al. | 435/14 | 90/05910 | 5/1990 | (WO) . |
| 5,791,344 | 8/1998 | Schulman et al. | 435/14 | 91/01680 | 2/1991 | (WO) . |
| | | | | 91/04704 | 4/1991 | (WO) . |
| | | | | 91/15993 | 10/1991 | (WO) . |

FOREIGN PATENT DOCUMENTS

| | | |
|---|---|---|
| 0 026 995 A1 | 4/1981 | (EP) . |
| 0 048 090 A2 | 3/1982 | (EP) . |
| 0 078 636 A1 | 5/1983 | (EP) . |
| 0 096 288 A1 | 12/1983 | (EP) . |
| 0 125 139 A2 | 11/1984 | (EP) . |
| 92/13271 | 8/1992 | (WO) . |
| 94/20602 | 9/1994 | (WO) . |
| 94/27140 | 11/1994 | (WO) . |
| 96/30431 | 10/1996 | (WO) . |
| WO 96/30431 | 10/1996 | (WO) . |

| | | |
|---|---|---|
| 97/02847 | 1/1997 | (WO) . |
| 97/19344 | 5/1997 | (WO) . |
| 97/42882 | 11/1997 | (WO) . |
| 97/42883 | 11/1997 | (WO) . |
| 97/42886 | 11/1997 | (WO) . |
| 97/42888 | 11/1997 | (WO) . |
| 97/43962 | 11/1997 | (WO) . |

OTHER PUBLICATIONS

Albery, W. J. et al., "Amperometric Enzyme Electrodes," *Phil. Trans. R. Soc. Lond.* B316:107–119 (1987).

Alcock, S. J. et al., "Continuous Analyte Monitoring to Aid Clinical Practice," *IEEE Engineering in Medicine and Biology*, 319–325 (1994).

Anderson, L. B. et al., "Thin–Layer Electrochemistry: Steady–State Methods of Studying Rate Processes," *J. Electroanal. Chem.*, 10:295–395 (1965).

Bartlett, P. N. et al., "Covalent Binding of Electron Relays to Glucose Oxidation," *J. Chem. Soc. Chem. Commun.*, 1603–1604 (1987).

Bartlett, P. N. et al., "Modification of glucose oxidase by tetrathiafulvalene," *J. Chem. Soc., Chem. Commun.*, 16 (1 page–Abstract only) (1990).

Bartlett, P. N. et al., "Strategies for the Development of Amperometric Enzyme Electrodes," *Biosensors*, 3:359–379 (1987/88).

Bindra, D.S. et al., "Design and in Vitro Studies of a Needle–Type Glucose Sensor for Subcutaneous Monitoring", *Anal. Chem.*, 63(17):1692–1696 (Sep. 1, 1991).

Bobbioni–Harsch, E. et al., "Lifespan of subcutaneous glucose sensors and their performances during dynamic glycaemia changes in rats," *J. Biomed. Eng.* 15:457–463 (1993).

Brandt, J. et al., "Covalent attachment of proteins to polysaccharide carriers by means of benzoquinone," *Biochim. Biophys. Acta*, 386(1)(1 page Abstract only) (1975).

Brownlee, M. et al., "A Glucose–Controlled Insulin–Delivery System: Semisynthetic Insulin Bound to Lectin", *Science*, 206(4423):1190–1191 (Dec. 7, 1979).

Cass, A.E.G. et al., "Ferricinum Ion As An Electron Acceptor for Oxido–Reductases," *J. Electroanal. Chem.*, 190:117–127 (1985).

Cass, A.E.G. et al., "Ferrocene–Mediated Enzyme Electrode for Amperometric Determination of Glucose", *Anal. Chem.*, 56(4):667–671 (Apr. 1984).

Castner, J. F. et al., "Mass Transport and Reaction Kinetic Parameters Determined Electrochemically for Immobilized Glucose Oxidase," *Biochemisty*, 23(10):2203–2210 (1984).

Claremont, D.J. et al., "Biosensors for Continuous In Vivo Glucose Monitoring", *IEEE Engineering in Medicine and Biology Society 10th Annual International Conference*, New Orleans, Louisiana, 3 pgs. (Nov. 4–7, 1988).

Clark, L.C. et al., "Differential Anodic Enzyme Polarography for the Measurement of Glucose", *Oxygen Transport to Tissue: Instrumentation, Methods, and Physiology*, 127–132 (1973).

Clark, L.C., Jr. et al., "Electrode Systems for Continuous Monitoring in Cardiovascular Surgery," *Annals New York Academy of Sciences*, pp. 29–45 (1962).

Clark, L.C. et al., "Long–term Stability of Electroenzymatic Glucose Sensors Implanted in Mice," *Trans. Am. Soc. Artif. Intern. Organs*, XXXIV:259–265 (1988).

Clarke, W. L., et al., "Evaluating Clinical Accuracy of Systems for Self–Monitoring of Blood Glucose," *Diabetes Care*, 10(5):622–628 (Sep.–Oct. 1987).

Csöregi, E. et al., "Design, Characterization, and One–Point in Vivo Calibration of a Subcutaneously Implanted Glucose Electrode," *Anal. Chem.* 66(19):3131–3138 (Oct. 1, 1994).

Csöregi, E. et al., "Design and Optimization of a Selective Subcutaneously Implantable Glucose Electrode Based on "Wired" Glucose Oxidase," *Anal. Chem.* 67(7):1240–1244 (Apr. 1, 1995).

Csöregi, E. et al., "On–Line Glucose Monitoring by Using Microdialysis Sampling and Amperometric Detection Based on "Wired" Glucose Oxidase in Carbon Paste," *Mikrochim. Acta.* 121:31–40 (1995).

Davis, G., "Electrochemical Techniques for the Development of Amperometric Biosensors", *Biosensors*, 1:161–178 (1985).

Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme," *J. Phys. Chem.*, 91(6):1285–1289 (1987).

Degani, Y. et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.*, 110(8):2615–2620 (1988).

Degani, Y. et al., "Electrical Communication between Redox Centers of Glucose Oxidase and Electrodes via Electrostatically and Covalently Bound Redox Polymers," *J. Am. Chem. Soc.*, 111:2357–2358 (1989).

Denisevich, P. et al., "Unidirectional Current Flow and Charge State Trapping at Redox Polymer Interfaces on Bilayer Electrodes: Principles, Experimental Demonstration, and Theory," *J. Am. Chem. Soc.*, 103(16):4727–4737 (1981).

Dicks, J. M., "Ferrocene modified polypyrrole with immobilised glucose oxidase and its application in amperometric glucose microbiosensors," *Ann. Biol. clin.*, 47:607–619 (1989).

Engstrom, R.C., "Electrochemical Pretreatment of Glassy Carbon Electrodes", *Anal. Chem.*, 54(13):2310–2314 (Nov. 1982).

Engstrom, R.C. et al., "Characterization of Electrochemically Pretreated Glassy Carbon Electrodes", *Anal. Chem.*, 56(2):136–141 (Feb. 1984).

Ellis, C. D., "Selectivity and Directed Charge Transfer through an Electroactive Metallopolymer Film," *J. Am. Chem. Soc.*, 103(25):7480–7483 (1981).

Feldman, B.J. et al., "Electron Transfer Kinetics at Redox Polymer/Solution Interfaces Using Microelectrodes and Twin Electrode Thin Layer Cells", *J. Electroanal. Chem.*, 194(1):63–81 (Oct. 10, 1985).

Fischer, H. et al., "Intramolecular Electron Transfer Mediated by 4,4'–Bipyridine and Related Bridging Groups", *J. Am. Chem. Soc.*, 98(18):5512–5517 (Sep. 1, 1976).

Foulds, N.C. et al., "Enzyme Entrapment in Electrically Conducting Polymers," *J. Chem. Soc., Faraday Trans 1.*, 82:1259–1264 (1986).

Foulds, N.C. et al., "Immobilization of Glucose Oxidase in Ferrocene–Modified Pyrrole Polymers," *Anal. Chem.*, 60(22):2473–2478 (Nov. 15, 1988).

Frew, J.E. et al., "Electron–Transfer Biosensors", *Phil. Trans. R. Soc. Lond.*, B316:95–106 (1987).

Gorton, L. et al., "Selective detection in flow analysis based on the combination of immobilized enzymes and chemically modified electrodes," *Analytica Chimica Acta.*, 250:203–248 (1991).

Gregg, B. A. et al., "Cross–Linked Redox Gels Containing Glucose Oxidase for Amperometric Biosensor Applications," *Analytical Chemistry*, 62(3):258–263 (Feb. 1, 1990).

Gregg, B. A. et al., "Redox Polymer Films Containing Enzymes. 1. A Redox–Conducting Epoxy Cement: Synthesis, Characterization, and Electrocatalytic Oxidation of Hydroquinone," *J. Phys. Chem.*, 95(15):5970–5975 (1991).

Hale, P.D. et al., "A New Class of Amperometric Biosensor Incorporating a Polymeric Electron–Transfer Mediator," *J. Am. Chem. Soc.*, 111(9):3482–3484 (1989).

Harrison, D.J. et al., "Characterization of Perfluorosulfonic Acid Polymer Coated Enzyme Electrodes and a Miniaturized Integrated Potentiostat for Glucose Analysis in Whole Blood", *Anal. Chem.*, 60(19):2002–2007 (Oct. 1, 1988).

Hawkridge, F. M. et al., "Indirect Coulometric Titration of Biological Electron Transport Components," *Analytical Chemistry*, 45(7):1021–1027 (Jun. 1973).

Heller, A., "Amperometric biosensors based on three–dimensional hydrogel–forming epoxy networks," *Sensors and Actuators B*, 13–14:180–183 (1993).

Heller, A., "Electrical Connection of Enzyme Redox Centers to Electrodes," *J. Phys. Chem.*, 96(9):3579–3587 (1992).

Heller, A., "Electrical Wiring of Redox Enzymes," *Acc. Chem. Res.*, 23(5):129–134 (1990).

Ianniello, R.M. et al. "Immobilized Enzyme Chemically Modified Electrode as an Amperometric Sensor", *Anal. Chem.*, 53(13):2090–2095 (Nov. 1981).

Ianniello, R.M. et al., "Differential Pulse Voltammetric Study of Direct Electron Transfer in Glucose Oxidase Chemically Modified Graphite Electrodes", *Anal. Chem.*, 54:(7):1098–1101 (Jun. 1981).

Ikeda, T. et al., "Glucose oxidase–immobilized benzoquinone–carbon paste electrode as a glucose sensor," *Agric. Biol. Chem.*, 49(2) (1 page–Abstract only)(1985).

Ikeda, T. et al., "Kinetics of Outer–Sphere Electron Transfers Between Metal Complexes in Solutions and Polymeric Films on Modified Electrodes", *J. Am. Chem. Soc.*, 103(25):7422–7425 (Dec. 16, 1981).

Johnson, J. M. et al., "Potential–Dependent Enzymatic Activity in an Enzyme Thin–Layer Cell," *Anal. Chem.* 54:1377–1383 (1982).

Johnson, K.W., "Reproducible Electrodeposition of Biomolecules for the Fabrication of Miniature Electroenzymatic Biosensors," *Sensors and Actuators B Chemical*, B5:85–89 (1991).

Jönsson, G. et al., "An Amperometric Glucose Sensor Made by Modification of a Graphite Electrode Surface With Immobilized Glucose Oxidase and Adsorbed Mediator", *Biosensors*, 1:355–368 (1985).

Josowicz, M. et al., "Electrochemical Pretreatment of Thin Film Platinum Electrodes", *J. Elecrochem. Soc.*, 135(1):112–115 (Jan. 1988).

Katakis, I. et al., "Electrostatic Control of the Electron Transfer Enabling Binding of Recombinant Glucose Oxidase and Redox Polyelectrolytes," *J. Am. Chem. Soc.*, 116(8):3617–3618 (1994).

Katakis, I. et al., "L–α–Glycerophosphate and L–Lactate Electrodes Based on the Electrochemical "Wiring" of Oxidases," *Analytical Chemisry*, 64(9):1008–1013 (May 1, 1992).

Kenausis, G. et al., "'Wiring' of glucose oxidase and lactate oxidase within a hydrogel made with poly(vinyl pyridine) complexed with $[Os(4,4'-dimethoxy-2,2'-bipyridine)_2 Cl]^{+/2+}$," *J. Chem. Soc., Faraday Trans.*, 92(20):4131–4136 (1996).

Koudelka, M. et al., "In–Vivo Behaviour of Hypodermically Implanted Microfabricated Glucose Sensors", *Biosensors & Bioelectronics*, 6(1):31–36 (1991).

Kulys, J. et al., "Mediatorless peroxidase electrode and preparation of bienzyme sensors," *Bioelectrochemisty and Bioenergetics*, 24:305–311 (1990).

Lager, W. et al., "Implantable Electrocatalytic Glucose Sensor," *Horm. Metab. Res.*, 26:526–530 (Nov. 1994).

Lindner, E. et al. "Flexible (Kapton–Based) Microsensor Arrays of High Stability for Cardiovascular Applications", *J. Chem. Soc.Faraday Trans.*, 89(2):361–367 (Jan. 21, 1993).

Maidan, R. et al., "Elimination of Electrooxidizable Interferant–Produced Currents in Amperometric Biosensors," *Analytical Chemistry*, 64(23):2889–2896 (Dec. 1, 1992).

Mastrototaro, J.J. et al., "An Electroenzymatic Glucose Sensor Fabricated on a Flexible Substrate", *Sensors and Biosensors B Chemical*, B5:139–144 (1991).

McNeil, C. J. et al., "Thermostable Reduced Nicotinamide Adenine Dinucleotide Oxidase: Application to Amperometric Enzyme Assay," *Anal. Chem.*, 61(1):25–29 (Jan. 1, 1989).

Miyawaki, O. et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, 838:60–68 (1985).

Moatti–Sirat, D. et al., "Evaluating in vitro and in vivo the inteference of ascorbate and acetaminophen on glucose detection by a needle–type glucose sensor," *Biosensors & Bioelectronics*, 7(5):345–352 (1992).

Moatti–Sirat, D. et al., "Reduction of acetaminophen interference in glucose sensors by a composite Nafion membrane: demonstration in rats and man," *Diabetologia*, 37(6) (1 page–Abstract only) (Jun. 1994).

Moatti–Sirat, D. et al., "Towards continuous glucose monitoring: in vivo evaluation of a miniaturized glucose sensor implanted for several days in rat subcutaneous tissue," *Diabetologia*, 35(3) (1 page–Abstract only) (Mar. 1992).

Nagy, G. et al., "A New Type of Enzyme Electrode: The Ascorbic Acid Eliminator Electrode," *Life Sciences*, 31(23):2611–2616 (1982).

Nakamura, S. et al., "Effect of Periodate Oxidation on the Structure and Properties of Glucose Oxidase," *Biochimica et Biophysica Acta.*, 445:294–308 (1976).

Narazimhan, K. et al., "p–Benzoquinone activation of metal oxide electrodes for attachment of enzymes," *Enzyme Microb. Technol.*, 7(6)(1 page–Abstract only)(1985).

Ohara, T. J. et al., "Glucose Electrodes Based on Cross–Linked $[Os(bpy)_2Cl]^{+/2+}$ Complexed Poly(1–vinylimadazole) Films," *Analytical Chemistry*, 65(23):3512–3516 (Dec. 1, 1993).

Ohara, T. J., "Osmium Bipyridyl Redox Polymers Used in Enzyme Electrodes," *Platinum Metals Rev.*, 39(2):54–62 (Apr. 1995).

Ohara, T. J. et al., ""Wired" Enzyme Electrodes for Amperometric Determination of Glucose or Lactate in the Presence of Interfering Substances," *Analytical Chemistry*, 66(15):2451–2457 (Aug. 1, 1994).

Olievier, C. N. et al., "In vivo Measurement of Carbon Dioxide Tension with a Miniature Electrode," *Pflugers Arch.* 373:269–272 (1978).

Paddock, R. et al., "Electrocatalytic reduction of hydrogen peroxide via direct electron transfer from pyrolytic graphite electrodes to irreversibly adsorbed cytochrome c peroxidase," *J. Electroanal. Chem.*, 260:487–494 (1989).

Palleschi, G. et al., "A Study of Interferences in Glucose Measurements in Blood by Hydrogen Peroxide Based Glucose Probes", *Anal. Biochem.*, 159:114–121 (1986).

Pankratov, I. et al., "Sol–gel derived renewable–surface biosensors," *Journal of Electroanalytical Chemistry*, 393:35–41 (1995).

Pathak, C. P. et al., "Rapid Photopolymerization of Immunoprotective Gels in Contact with Cells and Tissue," *J. Am. Chem. Soc.*, 114(21):8311–8312 (1992).

Pickup, J., "Developing glucose sensors for in vivo use," *Tibtech*, 11: 285–289 (Jul. 1993).

Pickup, J. C. et al., "In vivo molecular sensing in diabetes mellitus: an implantable glucose sensor with direct electron transfer," *Diabetologia*, 32(3):213–217 (1989).

Pickup, J. et al., "Potentially–implantable, amperometric glucose sensors with mediated electron transfer: improving the operating stability," *Biosensors*, 4(2) (1 page–Abstract only) (1989).

Pishko, M.V. et al., "Amperometric Glucose Microelectrodes Prepared Through Immobilization of Glucose Oxidase in Redox Hydrogels", *Anal. Chem.*, 63(20):2268–2272 (Oct. 15, 1991).

Poitout, V. et al., "A glucose monitoring system for on line estimation in man of blood glucose concentration using a miniaturized glucose sensor implanted in the subcutaneous tissue and a wearable control unit," *Diabetolgia*, 36(7) (1 page–Abstract only) (Jul. 1993).

Poitout, V. et al., "Calibration in dogs of a subcutaneous miniaturized glucose sensor using a glucose meter for blood glucose determination," *Biosensors & Bioelectronics*, 7:587–592 (1992).

Poitout, V. et al., "In vitro and in vivo evaluation in dogs of a miniaturized glucose sensor," *ASAIO Transactions*, 37(3) (1 page–Abstract only) (Jul.–Sep. 1991).

Pollak, A. et al., "Enzyme Immobilization by Condensation Copolymerization into Cross–Linked Polyacrylamide Gels," *J. Am. Chem. Soc.*, 102(20):6324–6336 (1980).

Reach, G. et al., "Can Continuous Glucose Monitoring Be Used for the Treatment of Diabetes?" *Analytical Chemistry*, 64(6):381–386 (Mar. 15, 1992).

Rebrin, K. et al., "Automated Feedback Control of Subcutaneous Glucose Concentration in Diabetic Dogs", *Diabetologia*, 32(8):573–576 (Aug. 1989).

Sakakida, M. et al., "Ferrocene–mediate needle–type glucose sensor covered with newly designed biocompatible membrane," *Sensors and Actuators B*, 13–14:319–322 (1993).

Samuels, G. J. et al., "An Electrode–Supported Oxidation Catalyst Based on Ruthenium (IV). pH "Encapsulation" in a Polymer Film," *J. Am. Chem. Soc.*, 103(2):307–312 (1981).

Sasso, S.V. et al., "Electropolymerized 1,2–Diaminobenzene as a Means to Prevent Interferences and Fouling and to Stabilize Immobilized Enzyme in Electrochemical Biosensors", *Anal. Chem.*, 62(11):1111–1117 (Jun. 1, 1990).

Scheller, F. et al., "Enzyme electrodes and their application," *Phil. Trans. R. Soc, Lond.*, B 316:85–94 (1987).

Schmehl, R.H. et al., "The Effect of Redox Site Concentration on the Rate of Mediated Oxidation of Solution Substrates by a Redox Copolymer Film", *J. Electroanal. Chem.*, 152:97–109 (Aug. 25, 1983).

Shichiri, M. et al., "Glycaemic Control in Pancreatetomized Dogs with a Wearable Artificial Endocrine Pancreas", *Diabetologia*, 24(3):179–184 (Mar. 1983).

Sittampalam, G. et al., "Surface–Modified Electrochemical Detector for Liquid Chromatography", *Anal. Chem.*, 55(9):1608–1610 (Aug. 1983).

Soegijoko, S. et al., *Horm. Metabl. Res., Suppl. Ser*, 12 (1 page–Abstract only) (1982).

Sprules, S. D. et al., "Evaluation of a New Disposable Screen–Printed Sensor Strip for the Measurement of NADH and Its Modification to Produce a Lactate Biosensor Employing Microliter Volumes," *Electroanalysis*, 8(6):539–543 (1996).

Sternberg, F. et al., "Calibration Problems of Subcutaneous Glucosensors when Applied "In–Situ" in Man," *Horm. metabl. Res*, 26:524–525 (1994).

Sternberg, R. et al., "Covalent Enzyme Coupling on Cellulose Acetate Membranes for Glucose Sensor Development," *Analytical Chemistry*, 60(24):2781–2786 (Dec. 15, 1988).

Sternberg, R. et al., "Study and Development of Multilayer Needle–type Enzyme–based Glucose Microsensors," *Biosensors*, 4:27–40 (1988).

Suekane, M., "Immobolization of glucose isomerase," *Zeitschrift für Allgemeine Mikrobiologie*, 22(8):565–576 (1982).

Tajima, S. et al., "Simultaneous Determination of Glucose and 1,5–Anydroglucitol", *Chemical Abstracts*, 111(25):394 111:228556g (Dec. 18, 1989).

Tarasevich, M.R. "Bioelectrocatalysis", *Comprehensive Treatise of Electrochemistry*, 10(Ch. 4):231–295 (1985).

Tatsuma, T. et al., "Enzyme Monolayer– and Bilayer–Modified Tin Oxide Electrodes for the Determination of Hydrogen Peroxide and Glucose," *Anal. Chem.*, 61(21):2352–2355 (Nov. 1, 1989).

Taylor, C. et al., "'Wiring' of glucose oxidase within a hydrogel made with polyvinyl imidazole complexed with [(Os–4,4'–dimethoxy–2,2'–bipyridine)Cl]$^{+/2+}$," *Journal of Electroanalytical Chemistry*, 396:511–515 (1995).

Trojanowicz, M. et al., "Enzyme Entrapped Polypyrrole Modified Electrode for Flow–Injection Determination of Glucose," *Biosensors & Bioelectronics*, 5:149–156 (1990).

Turner, A.P.F. et al., "Diabetes Mellitus: Biosensors for Research and Management", *Biosensors*, 1:85–115 (1985).

Turner, R.F.B. et al., "A Biocompatible Enzyme Electrode for Continuous in vivo Glucose Monitoring in Whole Blood," *Sensors and Actuators*, B1(1–6):561–564 (Jan. 1990).

Tuzhi, P. et al., "Constant Potential Pretreatment of Carbon Fiber Electrodes for In Vivo Electrochemistry", *Analytical Letters*, 24(6):935–945 (1991).

Umaha, M., "Protein–Modified Electrochemically Active Biomaterial Surface," *U.S. Army Research Office Report*, (12 pages) (Dec. 1988).

Urban, G. et al., "Miniaturized Thin–Film Biosensors Using Covalently Immobilized Glucose Oxidase", *Biosensors & Bioelectronics*, 6(7):555–562 (1991).

Velho, G. et al., "In Vitro and In Vivo Stability of Electrode Potentials in Needle–Type Glucose Sensors", *Diabetes*, 38(2):164–171 (Feb. 1989).

Velho, G. et al., "Strategies for calibrating a subcutaneous glucose sensor," *Biomed. Biochin. Acta*, 48(11/12):957–964 (1989).

Von Woedtke, T. et al., "In Situ Calibration of Implanted Electrochemical Glucose Sensors," *Biomed. Biochim. Acta*, 48(11/12):943–952 (1989).

Vreeke, M.S. et al., "Chapter 15: Hydrogen Peroxide Electrodes Based on Electrical Connection of Redox Centers of Various Peroxidases to Electrodes through a Three–Dimensional Electron–Relaying Polymer Network," *Diagnostic Biosensor Polymers*, 7 pgs. (Jul. 26, 1993).

Vreeke, M. et al., "Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network," *Analytical Chemistry*, 64(24):3084–3090 (Dec. 15, 1992).

Wang, J. et al., "Activation of Glassy Carbon Electrodes by Alternating Current Electrochemical Treatment", *Analytica Chimica Acta*, 167:325–334 (Jan. 1985).

Wang, J. et al., "Amperometric biosensing of organic peroxides with peroxidase–modified electrodes," *Analytica Chimica Acta.* 254:81–88 (1991).

Wang, D. L. et al., "Miniaturized Flexible Amperometric Lactate Probe," *Analytical Chemistry*, 65(8):1069–1073 (Apr. 15, 1993).

Wang, J. et al., "Screen–Printable Sol–Gel Enzyme–Containing Carbon Inks," *Analytical Chemistry*, 68(15):2705–2708 (Aug. 1, 1996).

Wang, J. et al., "Sol–Gel–Derived Metal–Dispersed Carbon Composite Amperometric Biosensors," *Electroanalysis*, 9(1):52–55 (1997).

Williams, D.L. et al., "Electrochemical–Enzymatic Analysis of Blood Glucose and Lactate", *Anal. Chem.*, 42(1):118–121 (Jan. 1970).

Wilson, G. S. et al., "Progress toward the Development of an Implantable Sensor for Glucose," *Clinical Chemistry*, 38(9):1613–1617 (1992).

Yabuki, S. et al., "Electro–conductive Enzyme Membrane," *J. Chem. Soc. Chem. Commun*, 945–946 (1989).

Yang, L. et al., "Determination of Oxidase Enzyme Substrates Using Cross–Flow Thin–Layer Amperometry," *Electroanalysis*, 8(8–9):716–721 (1996).

Yao, S.J. et al., "The Interference of Ascorbate and Urea in Low–Potential Electrochemical Glucose Sensing", *Proceedings of the Twelfth Annual International Conference of the IEEE Engineering in Medicine and Biology Society*, 12(2):487–489 (Nov. 1–4, 1990).

Yao, T. et al., "A Chemically–Modified Enzyme Membrane Electrode As An Amperometric Glucose Sensor," *Analytica Chimica Acta.*, 148:27–33 (1983).

Ye, L. et al., "High Current Density "Wired" Quinoprotein Glucose Dehydrogenase Electrode," *Anal. Chem.*, 65(3):238–241 (Feb. 1, 1993).

Yildiz, A. et al., "Evaluation of an Improved Thin–Layer Electrode," *Analytical Chemistry*, 40(70):1018–1024 (Jun. 1968).

Zamzow, K. et al., New Wearable Continuous Blood Glucose Monitor (BGM) and Artificial Pancreas (AP), *Diabetes*, 39:5A(20) (May 1990).

Zhang, Y. et al., "Application of cell culture toxicity tests to the development of implantable biosensors," *Biosensors & Bioelectronics*, 6:653–661 (1991).

Zhang, Y. et al., "Elimination of the Acetaminophen Interference in an Implantable Glucose Sensor," *Anal. Chem.* 66:1183–1188 (1994).

Aisenberg et al., "Blood glucose, level monitoring alarm system," Great Britain Patent GB 1394171, issued May 14, 1975, (Abstract only).

Cerami, "Monitor for continuous in vivo measurement of glucose concentration," United States Patent 4,436,094, issued Mar. 13, 1984, 2 pages (Abstract only).

Franetzki, "Implantable, calibrateable measuring instrument for a body substance and a calibrating method," United States Patent 4,759,371, issued Jul. 26, 1988, 2 pages (Abstract only).

Gilli, "Apparatus and method employing plural electrode configurations for cardioversi on of atrial fibrillation in an arrhythmia control system," United States Patent 5,209,229, issued May 11, 1993, 2 pgs (Abstract only).

Klein, "Control and regulation device for glycemia," Great Britain Patent 1599241A, issued Sep. 30, 1981 (Abstract only).

Klein, "Method and apparatus for the control and regulation of glycemia," United States Patent 4,206,755, issued Jun. 10, 1980, 2 pages (Abstract only).

Lawton, "Implantable electrochemical sensor," United States Patent 4,016,866, issued Apr. 12, 1977, 2 pages (Abstract only).

Vadgama et al., "Sensor devices," United States Patent 5,531,878, issued Jul. 2, 1996, 2 pages (Abstract only).

Abstract from Korf, J. et al., "Monitoring of Glucose and Lactate Using Microdialysis: Applications in Neonates and Rat Brain", *Developmental Neuroscience*, vol. 15, No. 3–5, pp. 240–46 (1993).

Flentge F. et al., "An Enzyne–Reactor for Electrochemical Monitoring of Choline and Acetylcholine: Applications in High–Performance Liquid Chromatography, Brain Tissue, Microdialysis and Cerebrospinal Fluid", *Analytical Biochemistry*, vol. 204, No. 2, pp. 305–310, (Aug. 1, 1992).

Laurell, T., "A Continuous Glucose Monitoring System Based on Microdialysis", *Journal of Med. Eng. & Tech.*, vol. 16, No. 5, pp. 187–193 (Sep./Oct. 1992).

Marko–Varga, G. et al., "Enzyme–Based Biosensor as a Selective Detection Unit in Column Liquid Chromatography", *Journal of Chromatography A*, vol. 660, pp. 153–167 (1994).

Schmidt, F.J. et al., "Calibration of a Wearable Glucose Sensor", *The International Journal of Artificial Organs*, vol. 15, No. 1, pp. 55–61 (1992).

SUBCUTANEOUS GLUCOSE ELECTRODE

This is a Continuation of application Ser. No. 08/299,526, filed Sep. 1, 1994, now U.S. Pat. No. 5,593,852 which application are incorporated herein by reference, which is a continuation in part of U.S. patent application Ser. No. 08/161,682, filed Dec. 2, 1993, now U.S. Pat. No. 5,356,786, which is hereby incorporated by reference for all purposes.

This work was supported in part by the National Institutes of Health (DK42015). Accordingly, the U.S. government may have rights in this invention.

FIELD OF THE INVENTION

The present invention relates to in vivo enzyme biosensors and more specifically to miniature glucose sensors for subcutaneous measurement of glucose with one-point calibration.

BACKGROUND

In response to the need for frequent or continuous in vivo monitoring of glucose in diabetics, particularly in brittle diabetes, a range of possible in vivo glucose electrodes have been studied. The desired characteristics of these electrodes include safety, clinical accuracy and reliability, feasibility of in vivo recalibration, stability for at least one hospital shift of eight hours, small size, ease of insertion and removal, and a sufficiently fast response to allow timely intervention. The in vivo recalibration should be based upon withdrawal of a single sample of body fluid, e.g., blood, and measuring its glucose concentration. This is termed "one point calibration".

Keys to safety are absence of leachable components, biocompatibility, and limiting of the potentially hazardous foreign matter introduced into the body to an amount that is inconsequential in a worst case failure. The clinical accuracy must be such that even when the readings are least accurate, the clinical decisions based on these be still correct. Feasibility of prompt confirmation of proper functioning of the sensors and of periodic in vivo recalibration is of essence if a physician is to allow the treatment of a patient to depend on the readings of the sensor. This one-point calibration, relying on the signal at zero glucose concentration being zero and measuring the blood glucose concentration at one point in time, along with the signal, is of essence, but has heretofore been elusive. The sensitivity must be sufficiently stable for the frequency of required in vivo recalibration to not be excessive. The sensor must be small enough to be introduced and removed with minimal discomfort to the patient and for minimal tissue damage. It is preferred that the sensor be subcutaneous and that it be inserted and removed by the patient or by staff in a physician's office. Finally, its response time must be fast enough so that corrective measures, when needed, can be timely.

In response to some of these needs, needle type and other subcutaneous amperometric sensors were considered. The majority of these utilized platinum-iridium, or platinum black to electrooxidize $H_2O_2$ generated by the glucose oxidase (GOX) catalyzed reaction of glucose and oxygen. In these sensors, the GOX was usually in large excess and immobilized, often by crosslinking with albumin and glutaraldehyde. To exclude electrooxidizable interferants, membranes of cellulose acetate and sulfonated polymers including Nafion™ were used. Particular attention was paid to the exclusion of the most common electrooxidizable interferants: ascorbate, urate and acetaminophen. Also to cope with the interferants, two-electrode differential measurements were used, one electrode being sensitive to glucose and electrooxidizable interferants and the other only to interferants. One strategy for overcoming the problem of interferants, applicable also to the present invention, involves their preoxidation. Another strategy involves shifting, through chemical changes, the redox potential of the polymer in the sensing layer to more reducing potentials. When the redox potential of the polymer is in the region between about −0.15 V and +0.15 V versus the standard calomel electrode (SCE), and the electrodes are poised in their in vivo operation between about −0.10 and +0.25 V, the rate of electrooxidation of interferants such as ascorbate, urate, and acetaminophen is very slow relative to that of glucose through its physiological concentration range. Thus, also the currents from electrooxidation of interferants are small relative to those of glucose.

To make the electrodes more biocompatible, hydrophilic polyurethanes, poly(vinyl alcohol) and polyHEMA membranes have been used.

Several researchers tested GOX-based glucose sensors in vivo and obtained acceptable results in rats, rabbits, dogs, pigs, sheep and humans. These studies validated the subcutaneous tissue as an acceptable glucose sensing site. Good correlation was observed between intravascular and subcutaneous glucose concentrations. They also demonstrated the need for in vivo sensor calibration. Another approach to in vivo glucose monitoring was based on coupling subcutaneous microdialysis with electrochemical detection. To control and adjust the linear response range, electrodes have been made glucose-diffusion limited, usually through glucose transport limiting membranes.

Diffusional mediators, through which the $O_2$ partial pressure dependence of the signals is reduced, are leached from sensors. Such leaching introduces an unwanted chemical into the body, and also leads to loss in sensitivity, particularly in small sensors. In microsensors, in which outward diffusion of the mediator is radial, the decline in sensitivity is rapid. This problem has been overcome in "wired" enzyme electrodes, i.e., electrodes made by connecting enzymes to electrodes through crosslinked electron-conducting redox hydrogels ("wires"). Glucose oxidase has been "wired" with polyelectrolytes having electron relaying $[Os(bpy)_2Cl]^{+/2+}$ redox centers in their backbones. Hydrogels were formed upon crosslinking the enzyme and its wire on electrodes. These electrodes had high current densities and operated at a potential of 0.3V vs. SCE. The electrooxidizable interferants are eliminated through peroxidase-catalyzed preoxidation in a second, nonwired, hydrogen peroxide generating layer on the "wired" enzyme electrode.

SUMMARY OF THE INVENTION

A small (e.g., 0.29 mm), recessed, non-corroding metal (e.g., gold, platinum, palladium) or carbon wire electrode for subcutaneous in vivo glucose monitoring, approaching in its performance all of the above listed requirements, including in vivo one-point calibration, has been produced. The electrode was constructed by depositing active polymer layers into a recess formed by etching away gold from an insulated gold wire.

The active polymer layers, including a sensing layer, a glucose flux-limiting layer, a biocompatable layer, and optionally a peroxidase-based interferant eliminating layer, were protected within the recess against mechanical damage. (The peroxidase-based interferant eliminating layer is not required when a lower redox potential polymer is used, as described above.) The recess and its polymer layers also reduced the transport of glucose to the wire electrode contacting sensing layer.

By limiting the glucose flux, the desired linear response range, spanning the clinically relevant glucose concentration range was obtained. The inventive biosensors are able to accurately measure, for example, approximately 2–30 m$\mu$ glucose and approximately 0.5–10 m$\mu$ lactate, in vivo. The sensor has no leachable components, and its four crosslinked polymer layers contain only about 5 $\mu$g of immobilized material, and only a few nanograms of polymer-bound osmium. Preoxidation of the interferants in one of the four layers makes possible one-point in vivo calibration of the sensor.

DETAILED DESCRIPTION OF THE INVENTION

Figure 1:
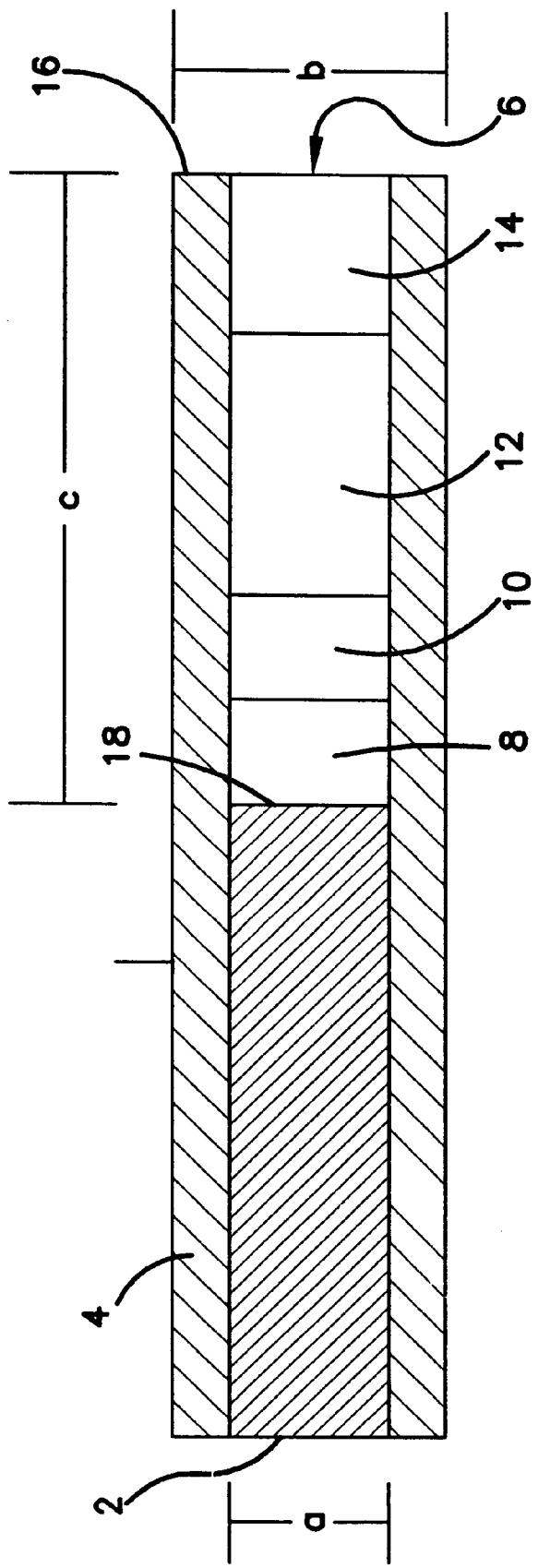
FIG. 1 is a schematic drawing of an electrode of the present invention.

The present invention includes an insulated, non-corroding conducting metal (e.g., gold, platinum, palladium) or carbon wire-based small (e.g., 290 $\mu$m) O.D. subcutaneous glucose sensor, allowing one-point calibration in vivo. As shown in FIG. 1, its construction involves coating a small (e.g., 250 $\mu$m) diameter non-corroding metal or carbon wire 2 with an electrically insulating material 4, e.g., a polyimide, and, layering in a recess 6 formed by etching or removing a portion of the metal or carbon, the following active polymeric layers: an immobilized, "wired," glucose oxidase layer 8; an electrically insulating and glucose diffusion limiting layer 10 formed, for example, by crosslinking a polyallylamine (PAL) with a polyaziridine (PAZ); optionally, an interference eliminating layer 12, e.g., of crosslinked horseradish-peroxidase and lactate oxidase; and a biocompatible film 14 e.g., of poly(ethylene oxide) (PEO) derivatized to allow its photo-crosslinking. The outside diameter a of the wire 2 is preferably about 0.25 mm or less, and the outside diameter b of the insulated wire is preferably about 0.3 mm or less. The recess 6 in the insulated electrode extends from the tip 16 of the electrode which is open to the surrounding environment, to the top 18 of the wire 2 in the insulating sheath, generally for a length c of less than about 0.150 mm, and preferably about 0.125 mm.

The electrodes have no leachable components. The total amount of polymers and enzymes is preferably about 5 $\mu$g. The glucose response through the physiologically relevant 2–20 mM concentration range is close to linear. The electrodes do not respond to ascorbate, urate or acetaminophenol for at least about 36 hours. Their 10–90% response time is about 90 seconds at 2 mM glucose and about 30 seconds at 20 mM glucose. Their sensitivity, after about 30 minutes equilibration, is stable for about 72 hours at 37° C. in 10 mM glucose, the current deviating from the average by less than ±5%. The electrodes have substantially no signal output, e.g., current, charge, or potential, when the concentration of the analyte to be measured is zero.

Two electrodes implanted subcutaneously in a rat tracked blood glucose levels, and their absolute, uncorrected current output was proportional to the blood glucose concentration. Analysis of the correlation between the blood glucose levels in the tail vein and the current output of the sensors in the subcutaneous regions of the thorax and between the scapulae of the same rat showed that even when the probed sites and organs differed in the extreme, one point in vivo calibration was valid. The analysis also showed the value of implanting redundant sensors. Had clinical decisions been made based on individual sensor readings, calibrated at one point, 94% would have been clinically correct. By using redundant sensors and accepting only those pairs of readings that were within one standard deviation, the percentage of the clinically correct decisions was increased to 99%.

It is understood that one of skill in the art may substitute various components of the biosensor described above with known materials to obtain an modified biosensor using the principles outlined herein. For example, the following substitutions are contemplated:

Base Electrode

The base electrode of the inventive sensor may be formed of a non-corroding metal or carbon wire, for example vitreous carbon, graphite, platinum, palladium, or gold. Gold is preferred, and is used in the following illustrative examples of the invention.

Insulator

The conductive metal or carbon wire is coated with an electrically insulating material, which also forms a wall about the recess which houses the active polymeric components. The insulating material may be, for example, polyurethane, teflon (fluorinated polymers), polyethyleneterephthalate (PET, Dacron) or polyimide. The insulating material is preferably a biocompatible polymer containing less than about 5% water when in equilibrium with physiological body fluids, e.g., subcutaneous tissue.

Recess

In general, the recess at the tip of the electrode is approximately 20 to 150 μm in length c, and preferably is approximately 50 to 125 μm.

Etching Method

The method for etching metal from the tip of the electrode described herein may utilize chloride, bromide or iodide in the bath in lieu of cyanide as described. Bromide is preferred, because it is less toxic and, like $Au(CN)_2^-$, $AuBr_4^-$ is a water soluble anion. Thus, in aqueous HBR, the metal, e.g., gold, an be etched by applying a sufficiently oxidizing potential where gold is electrolytically dissolved:

Au+4 HBr→HAuBr$_4$+3/2 H$_2$

Wired Enzyme Layer

In the sensing enzyme-containing layer, glucose oxidase may be substituted with other redox enzymes to measure other relevant clinical compounds. For example, lactate oxidase may be used for the in vivo detection of lactate, important in determining if an organ is receiving sufficient oxygen through the blood.

Useful redox polymers and methods for producing the sensing layer are described, for example, in U.S. Pat. Nos. 5,264,104; 5,356,786; 5,262,035, and 5,320,725. Additional redox polymers include, for example, poly(1-vinyl imidazole); poly(4-vinyl pyridine); or copolymers of 1-vinyl imidazole such as poly (acrylamide co-1-vinyl imidazole) where the imidazole or pyridine complexes with [Os (bpy)$_2$ Cl]$^{+/2+}$; [Os (4,4'-dimethyl bipyridine)$_2$Cl]$^{+/2+}$; [Os (4,4'-dimethyl phenanthroline)$_2$Cl]$^{+/2+}$; [Os (4,4'-dimethyoxy phenanthroline)$_2$Cl]$^{+/2+}$; and [Os (4,4'-dimethoxy bipyridine)$_2$Cl]$^{+/2+}$; to imidazole rings. The imidazole ring compounds are preferred because their complexes have more reducing redox potentials, i.e., closer to that of the SCE potential. At these more reducing potentials, the rate of electrooxidation of interferants and the current generated thereby.

Barrier Layer

The polymeric barrier layer is electrically insulating and limits diffusion of glucose through to the sensing layer. It may be formed, for example, by crosslinking a polyallylamine (PAL) with a polyaziridine (PAZ). Alternatively, PAL may be replaced wholly or in part with a zwitterionic polymer obtained by quaternizing poly(vinylpyridine) with bromoacetate and dialyzing against 0.15M NaCl or by a polyanion such as a polysulfonic acid.

The barrier layer may contain a polyanionic polymer, in which the rate of permeation of anionic interferants such as ascorbate and urate is slowed. This layer may also contain a polycation that enhances the retention of the polyanion by electrostatic bonds and improves wetting by the biocompatable layer.

Interference Eliminating Layer

As described above, this layer is optional, in that it is not required when a redox polymer having a more reducing potential is used, such as PVI$_{15}$-dmeOs (Ohara et al., *Analytical Chemistry*, 1994, 64:2451–2457). At operating potentials of approximately −0.10 to +0.25 for the glucose biosensor, the rate of electrooxidation of interferants such as ascorbate, urate and acetaminophen is very slow relative to that of glucose through its physiological concentration range.

When a separate interferant eliminating layer is used, it preferably contains a peroxidase enzyme which may or may not be preactivated. Such interferant eliminating layers are disclosed, for example, in U.S. Pat. No. 5,356,786, which discloses the structure and function of interferant eliminating biosensors. The glucose biosensor preferably contains lactate oxidase (LOX) in combination with peroxidase in the interferant eliminating layer. However, for biosensors used to detect lactate, glucose oxidase would be used with peroxidase. In a similar manner, the enzyme composition of the interferant eliminating layer may be altered for a specified function.

Biocompatable Layer

In general, the biocompatable layer is comprised of hydrogels, e.g., polymeric compositions which contain more than about 20% by weight of water when in equilibrium with a physiological environment such as living tissue or blood. An example is crosslinked poly(ethylene oxide), e.g., poly (ethylene oxide) tetraacrylate. The polymeric compositions must be non-toxic and compatible with living systems.

Method for Making Multi-Layered Recessed Biosensors

Insulated non-corroding metal or carbon wires that have been etched as described above to contain a recess at the tip, are placed in a block that serves as an X-Y positioner. The wires vertically traverse the block and are held in place, e.g., by pressure. The blocks with the wires can be formed of elements, each element having multiple half-cylinder grooves running vertically. The wires are placed in these grooves and the elements are assembled into the block using screws. For example, the block may be formed of aluminum having equally spaced holes, (900 for a 30×30 array of wires), each hole to contain one wire. The block is positioned under a fixed micronozzle that ejects a fluid in to the recess of the insulated wire.

To reduce the requirement of precision in the positioning of the block and the micronozzle, the nozzle is electrically charged, with the wire having an opposite charge, or the wire being grounded or at least having a potential such that there is a potential difference between the nozzle and the wire. Because the nozzle is charged, the microdroplets it ejects are also charged with the same type of charge (positive or negative) as the nozzle. The higher the potential on the nozzle (e.g., versus ground potential), the higher the charge on the ejected microdroplets. If the tip of the wire to be coated is at ground potential or has a charge of the opposite type, the charged microdroplets are guided into the recess to deposit on the electrode, even if the jet of microdroplets is not vertical, i.e., even if the micronozzle is not precisely aligned above the wire's tip.

Furthermore, the higher the electrical potential on the nozzle (relative to ground) the greater the charge on the ejected microdroplet. When the charge is high enough, the droplet breaks up into two or more smaller droplets because of electrostatic repulsion of charges on the droplet. Thus, the very small droplets all "drift" (drift meaning transport assisted by an electrical field) to the recessed electrode surface and are collected on it, even if they did not originate in a nozzle precisely aligned with the electrode.

This coating method is useful in making any small biosensor, not only those in recessed zones.

Clinical Use of the Recessed Biosensors

The recessed biosensors of the present invention have sufficient sensitivity and stability to be used as very small, subcutaneous biosensors for the measurement of clinically relevant compounds such as glucose and lactate. The electrodes accurately measure glucose in the range of about 2–30 $\mu$M and lactate in the range of about 0.5–10 mM. One function of the implanted biosensor is to sound an alarm when, for example, a patient's glucose concentration is too low or too high. When pairs of implanted electrodes are used, there are three situations in which an alarm is triggered: low glucose concentration, high glucose concentration; sensor malfunction as determined by a discrepancy between paired readings of the two sensors. A discrepancy sufficient to trigger the alarm may be, for example more than two or three times the standard deviation persisting for a defined period, e.g., not less than ten minutes. Such a system may be useful in sleeping patients, and also in emergency and intensive care hospital rooms, where vital functions are continuously monitored.

Another function of the inventive biosensors in to assist diabetics in maintaining their blood glucose levels near normal. Many diabetics now maintain higher than normal blood glucose levels because of danger of coma and death in severe hypoglycemia. However, maintaining blood glucose levels substantially, e.g., approximately 40% or more above normal leads to retinopathy and blindness as well as to kidney failure. Use of the subcutaneous biosensors to frequently, if not continuously, monitor glucose concentrations is desirable so that glucose concentrations can be maintained closer to an optimum level.

The subcutaneous biosensors can be used to measure the rate of rise and decline of glucose concentrations after a meal or the administration of glucose (e.g., a glucose tolerance test). The sensors are also useful in feedback loops for automatic or manually controlled maintenance of glucose concentrations within a defined range. For example, when used in conjunction with an insulin pump, a specified amount of insulin is delivered from the pump if the sensor glucose reading is above a set value.

In all of these applications, the ability to promptly confirm that the implanted sensor reading is accurate is essential. Prompt confirmation and rapid recalibration are possible only when one-point calibration is valid. Generally, even if a sensor's response is linear through the relevant concentration range, calibration requires at least two blood or fluid samples, withdrawn from the patient at times when the glucose concentration differs. It usually takes several hours for the glucose concentration to change sufficiently to validate proper functioning by two-point calibration. The ability to confirm and recalibrate using only one point is thus a highly desirable feature of the present invention.

Redundant sensors (e.g., at least two) are preferred in the clinical application of the subcutaneous biosensors. Such redundancy permits signaling of failure of any one sensor by recognition of an increase in the discrepancy between the readings of the sensors at one time point, e.g., more than two standard deviations apart. The redundant sensors may be implanted near each other or at remote sites.

It is preferred that the biosensors be implanted in subcutaneous tissue so as to make the sensor relatively unobtrusive, and at a site where they would not be easily dislodged, e.g., with turning or movement. It is also preferred, when readings are not corrected for temperature (which they generally are) that the sensors be implanted where they are likely to be at body temperature, e.g., near 37° C., and preferably covered by clothing. Convenient sites include the abdomen, inner thigh, arm.

Although we describe here continuous current measurement for assaying glucose, the electrical measurement by which the glucose concentration is monitored can be continuous or pulsed. It can be a current measurement, a potential measurement or a measurement of charge. It can be a steady state measurement, where a current or potential that does not substantially change during the measurement is monitored, or it can be a dynamic measurement, e.g., one in which the rate of current or potential change in a given time period is monitored. These measurements require at least one electrode in addition to the sensing electrode. This second electrode can be placed on the skin or can be implanted, e.g., subcutaneously. When a current is measured it is useful to have a potentiostat in the circuit connecting the implanted sensing electrode and the second electrode, that can be a reference electrode, such as an Ag/AgCl electrode. When a current is measured the reference electrode may serve also as the counter electrode. The counter electrode can also be a separate, third electrode, such as a platinum, carbon, palladium or gold electrode.

In addition to implanting the sending electrode in the body, fluid from the body, particularly fluid from the subcutaneous region, can be routed to an external sensor. it is preferred in this case to implant in the subcutaneous region a microfiltration giver and pull fluid to an evacuated container, the fluid traversing a cell containing the sensing electrode. Preferably this cell also contains a second electrode, e.g., a reference electrode which may serve also as a counter electrode. Alternatively, the reference and counter electrodes may be separate electrodes. In coulometric measurements only two electrodes, the sensing electrode and the counter electrode are required. The flow of body fluid amy be pulsed or continuous. Other than an implanted microfiltration fiber, also a microdialysis fiber may be used, preferably in conjunction with a pump.

Increased Stability of the Biosensors

To increase the stability and useful life of the inventive biosensors, it is advantageous to use intrinsically more stable enzymes and redox polymers. However, even if the enzyme and redox polymer degrade in the glucose electrooxidation process by which the signal (current) is generated, it is possible to greatly extend the useful life of the implanted electrodes and reduce the frequency of their required recalibration after implantation.

A simple measure by which the life of the implanted electrodes can be extended and the frequency of their required recalibration reduced involves turning the electrodes "on" by applying a bias, i.e., a potential, only during the period of measurement, then turning the biasing potential off or reducing it, so that a lesser current will flow. It is generally sufficient to perform only one measurement every five or even ten minutes, or longer, because glucose concentrations do not change abruptly.

Another measure is to lower the glucose flux to the sensing layer much as possible, consistent with maintaining adequate sensitivity and detectivity. Reduction of the glucose flux to the sensing layer reduces the current. Therefore, even though this stabilizes the electrodes, i.e., slows the loss in sensitivity, the flux dependent current must not be excessively reduced. Usually a current of 3–5 nA at 2 mM glucose concentration is adequate. When the glucose flux is lowered by using one or more glucose-flux reducing polymer slayers, such as the PAL/PAZ layer, the lifetime of the sensor is increased.

EXAMPLES

Example 1

Electrode Preparation

Electrodes were made of a polyamide-insulated 250 $\mu$m diameter gold wire, having an outer diameter (O.D.) of 290 $\mu$m (California Fine Wire Co., Grover City, Calif.). Heat shrinkable tubing (RNF 100 $3/64$– BK and $1/16$" BK, Thermofit®, Raychem, Menlo Park, Calif.) and a two component silver epoxy (Epo-tek $H_2OE$; Epoxy Tech, Inc., Billerica, Mass.) were used for electrode preparation.

The glucose sensing layer was made by crosslinking a genetically engineered glucose oxidase (rGOX) (35% purity, Chiron Corp., Emeryville, Calif.) with a polymer derived of poly(vinylimidazole) (PVI), made by complexing part of the imidazoles to $[Os(bpy)_2Cl]^{+/2+}$. The resulting redox polymer, termed PVI-Os, was synthesized according to a previously published protocol. (Ohara et al., 1993, *Anal. Chem.*, 65:24). Poly(ethylene glycol) diglycidyl ether 400 (PEDGE; Polysciences, Warrington, Pa.) was used as the crosslinker.

The barrier layer between the sensing and interference-eliminating layers was made of polyallylamine (PAL; Polysciences) crosslinked with a polyfunctional aziridine (PAZ) (XAMA-7; Virginia Chemicals, Portsmouth, Va.).

The interference-eliminating layer was prepared by co-immobilizing horseradish peroxidase (HRP) type VI (Cat. no. P-8375, 310 U/mg, denoted herein as HRP-VI, Sigma, St. Louis, Mo.) and HRP for immunological assay (No. 814407, min 1000 U/mg, denoted HRP-BM, Boehringer-Mannheim, Indianapolis, Ind.) with lactate oxidase from *Pediococcus sp. (Cat. No.* 1361, 40 U/mg denoted LOX, Genzyme, Cambridge, Mass.) and a recombinant microbial source (Cat. No. 1381 denoted rLOX, Genzyme). Co-immobilization was performed using sodium periodate (Cat. No. S-1147, Sigma) according to the methods described in Maidan and Heller, 1992, *Anal. Chem.* 64:2889–2896.

The biocompatible layer was made of 10% aqueous poly(ethylene oxide) tetraacrylate (PEO-TA). To form the photocrosslinkable polymer, PEO was acrylated by reaction with acryloyl chloride. The 18,500 g/mol PEO (Polysciences) is a tetrahydroxylated compound by virtue of two hydroxyl groups on a bisphenol A bisepoxide that linked two $\alpha$, $\omega$-hydroxy-terminated 9,000 g/mol PEO units. Acryloyl chloride (Aldrich, Milwaukee, Wis.) in a 2 to 5 molar excess was used to acrylate the polymer (10% w/v PEO in benzene). Triethylamine (Mallinkrodt, Paris, Ky.) was used as a proton acceptor equimolar with theacryloyl chloride.

Other chemicals used were bovine serum albumin (BSA) fraction V (Cat. No. A-2153), BSA, ascorbic acid, uric acid, 4-acetaminophenol, L(+)=lactic acid, and hydrogen peroxide 30%, all from Sigma. All chemicals were used as received. Solutions (if not otherwise specified) were made with distilled, deionized water. Glucose monitoring was performed in buffer, in bovine serum (Sigma, Cat. No. S-6648) containing antibiotic-antimycotic solution (Sigma, Cat. No. A-8909) at 37° C. and in rats.

Instrumentation

In making the recessed gold electrodes, a potentiostat/galvanostat (PAR Model 173, Princeton Applied Research, Princeton, N.J.) operated in a galvanostatic mode, and a sonicator (Fisher Scientific, Pittsburgh, Pa.) were used. Cyclic voltammograms were recorded with a potentiostat (PAR Model 273A) and a conventional electrochemical cell having a Pt wire counter and a SCE reference electrode and were evaluated with PAR 270 software. Glucose signals were monitored with a bipotentiostat (Biometra EP 30) and a two channel strip-chart recorder. The recessed electrodes were coated under a microscope (Bausch & Lomb) using a micromanipulator (Narishige, Seacliff, N.Y.). The micropipettes were pulled with a micropipette puller (Narishige). Temperature was controlled with an isothermal circulator (Fisher Scientific).

Electrode Preparation

Five cm lengths of polyamide insulated gold wire were cut with a sharp razor blade. Electrical contact was made at one end with silver epoxy to an insulated stainless steel wire and the junction was covered with insulating heat shrinkable tubing. The recess forming electrochemical etching process was carried out in 10 ml of 3M potassium cyanide, with the gold wire as the working electrode and a platinum or gold wire as the counter electrode. The wires were placed in contact with the bottom of the beaker, all electrodes being equidistant from the counter electrode. The beaker was sonicated during the etching procedure. The ends of the gold wires were bent upwards, so that agitation by the sonicator caused the oxygen bubbles formed during the etching process to rise and escape. The electrodes were then thoroughly washed and immersed in water for 30 minutes.

A recess 6, i.e., channel, in a polyamide insulated gold wire 2 is formed by electrochemical etching of the gold under galvanostatic control. By controlling the charge, the total amount of gold electrooxidized and dissolved as $Au(CN)_2$ is defined. When the conditions were set so that the CN- transport into the channel and the $Au(CN)_2$- transport out of it are not rate limiting, (e.g., sonicated bath and high concentration of potassium cyanide, at least approximately 0.2M, and preferably 3M), a flat gold wire surface is produced at the bottom of channels with aspect ratios of 0.5 to 2.0. Thus, when the CN-concentration is high enough and the wires are ultrasonically vibrated, the tips of gold wires are flat. Passage of 1.5 coulombs per electrode at 8 mA current produced approximately 125 $\mu$m deep cavities or channels. At theoretical efficiency for one-electron oxidation, 3.08 mg of gold would have been etched. The amount of gold actually etched was only 0.076 mg, showing significant CN- or water oxidation.

Nevertheless, the process is reproducible, accurate and fast with 20 electrodes being processed in each batch in less than five minutes. The recess-forming procedure was highly reproducible, with a deviation of ±10 $\mu$m found (using an objective micrometer) for a batch of 30 recessed electrodes. Before coating, the electrodes were examined under a microscope for flatness of the gold surface and correct depth.

FIG. 1 shows a schematic side view in cross-section of an electrode of the present invention, showing the gold wire 2, insulating coating 4, and recess or channel 6. The recessed gold surfaces were coated by filling of the cavities or channels 6 with aqueous solutions containing the crosslinkable components of the different layers, and their crosslinkers. The solutions were introduced under a microscope with a micropipette (connected to a microsyringe by polyethylene tubing and shrink tubing), using a micromanipulator. After application of each of the individual layers, the electrodes were cured overnight at room temperature, in air.

Electrode Structure

The electrodes were prepared by sequentially depositing four layers within the recess or channel 6. The layers were: the sensing layer 8, the insulating layer 10, the interference-eliminating layer 12 and the biocompatible layer 14. The sensing layer, containing "wired" redox enzyme is positioned adjacent to and in contact with the gold wire 2. The insulating layer 10 is positioned between the sensing layer 8 and the peroxidase-based interferant-eliminating layer 12. The biocompatible layer 14 fills the remaining space in the recess 6 and is in contact with the environment outside the electrode. The thin polymer layers are well protected by containment within the polyamide sleeve 4.

The sensing layer 8 was made by "wiring" rGOX to the gold electrode through a redox hydrogel to which the enzyme was covalently bound. The electrodes were prepared as follows: 10 mg/ml solutions were made from
1. the PVI-Os redox polymer in water,
2. the crosslinker, PEGDGE, in water, and
3. the enzyme, rGOX, in a 10 mM HEPES solution adjusted to pH 8.15.

A redox hydrogel was formed by mixing the three solutions so that the final composition (by weight) was 52% redox polymer, 35% enzyme and 13% crosslinker.

The insulating layer 10 prevented electrical contact between the redox hydrogel and the interference eliminating enzymes (HRP and LOX). PAL:PAZ was used as the insulating material. The film was deposited from a solution obtained by mixing in volume ratio of 1/1, 1/2 or 1/3, a PAL solution (4.5 mg in 100 mM HEPES buffer at pH 7.0) and a freshly prepared PAZ solution (30 mg/ml). The PAZ solution was used within 15 minutes of preparation.

The interference-eliminating layer 12 was prepared according to a previously published protocol, Maidan and Heller, 1992, *Anal. Chem.*, 64:2889–2896. 50 µl of a 12 mg/ml freshly prepared sodium periodate solution was added to 100 µl of a solution containing 20 mg/ml HRP (HRP-VI or HRP-BM) and 100 mg/ml LOX (LOX or rLOX) in 0.1 M sodium bicarbonate and the mixture was incubated in the dark for two hours. Alternatively, the oxidation of HRP could be carried out prior to adding LOX and crosslinking.

The biocompatible layer 14 films were photocrosslinked by exposure to UV light (UVP, Inc., San Gabriel, Calif.; Blak-Ray; spectral peak at 360 nM, UV irradiance at the sample 200 mW/cm$^2$) for one minute. The initiator used was 2,2-dimethoxy-2-phenylacetophenone (Aldrich). A solution of 300 mg/ml of the initiator in 1-vinyl-2-pyrrolidinone (Aldrich) was added to the prepolymer mixtures. Approximately 30 µl of the initiator solution was added per ml of 10% w/w aqueous solution of the tetraacrylated PEO. The prepolymers were crosslinked in situ inside the recess of the electrode. The films were prepared by filling the recess with the prepolymer solution twice and exposing the electrode to the UV light source after each time the cavity was filled.

In vitro Testing of Electrodes

In vitro experiments were carried out in batch fashion at 25° and 37° C., using a conventional three electrode electrochemical cell with the enzyme-modified gold wire as the working electrode, a platinum wire as the counter electrode and a saturated calomel reference electrode (SCE). The electrolyte was a 20 mM phosphate buffered-saline solution containing 0.15 M NaCl at pH 7.15. Experiments in serum were performed at 37° C., adding 100 µL antibiotic-antimycotic solution to 10 ml serum. Phosphate buffered-saline and serum were agitated during the experiments. The working potential was +0.3 V versus SCE for experiments with the PVI-Os polymers.

Structure and Performance

The depth c of the channel 6 and the thickness of the polymer layers in it controls the mass transport, i.e., flux of glucose, to the sensing layer. By controlling these parameters, the apparent Michaelis constant ($K_m$) is adjusted to about 20–30 mM glucose. The polyimide wall 4 of the channel 6 also protects the four polymer and polymer/enzyme layers 8, 10, 12, 14 against mechanical damage and reduces the hazard of their loss in the body. Because the glucose electrooxidation current is limited by glucose mass transport through the recess 16 and its polymer films 8, 10, 12, 14, rather than by mass transport to the tissue-exposed tip 16, the current is practically insensitive to motion. Evidently, the electrooxidation rate of glucose in the recessed sensing layer 8 is slower than the rate of glucose diffusion to the channel's outer fluid contacting interface.

Figure 2:
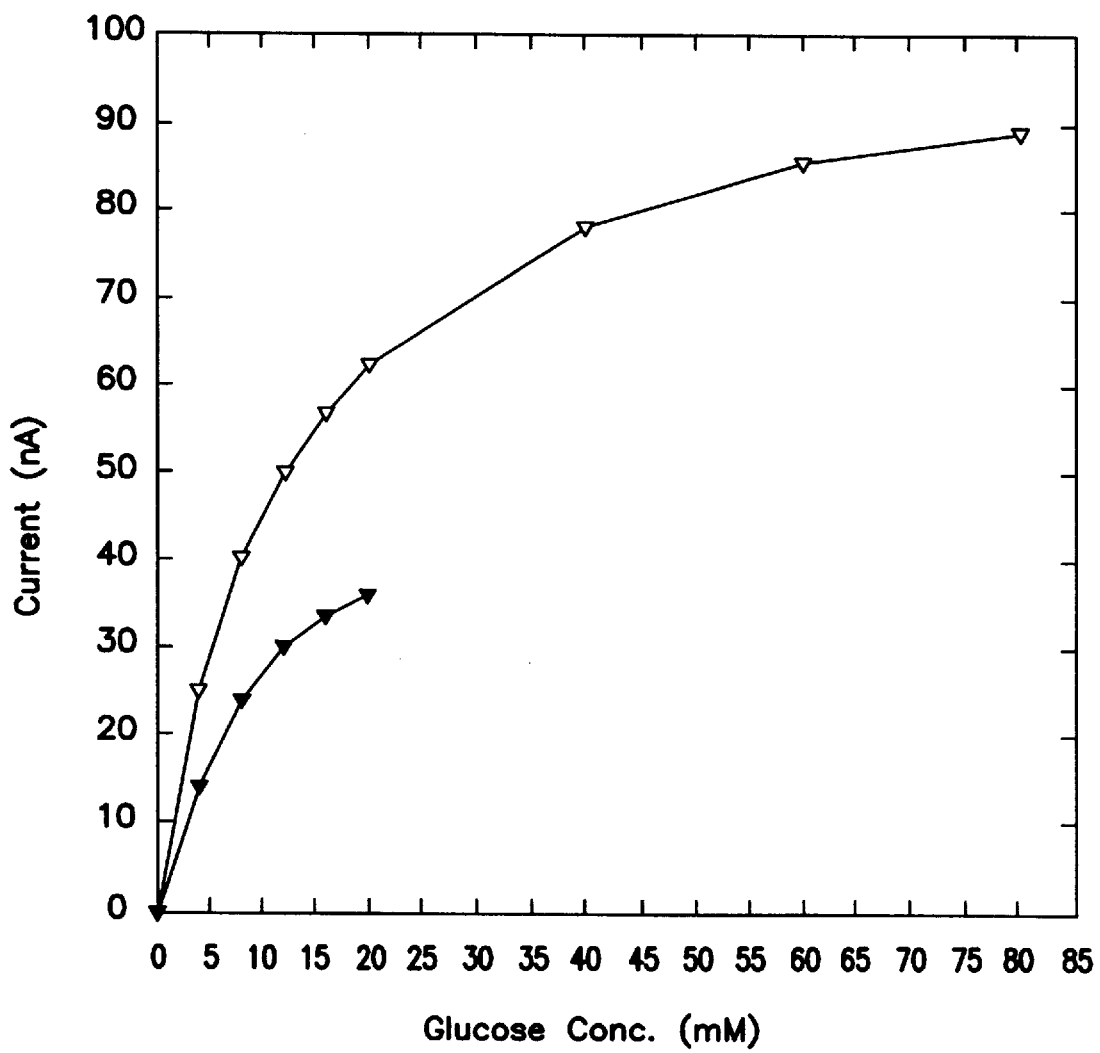
FIG. 2 is a graphical representation of data generated comparing current density of glucose electrooxidation on electrodes made with $PVI_5$-Os (open triangles) with those made with $PVI_3$-Os (filled triangles).

$PVI_5$-Os is preferred as the "wire" of the sensing layer when an interference eliminating layer of HRP and LOX is used, but not in the absence of this layer, i.e., when redox polymers with more reducing redox potential are preferred. The subscript (5) is used to indicate that, on the average, every fifth vinylimidazole mer carries an electron-relaying osmium center. Use of electrodes formed with $PVI_5$-Os and $PVI_3$-Os (every third 1-vinylimidazole mer carrying an osmium center) are compared in FIG. 2, and show higher current density of glucose electrooxidation on electrodes made with $PVI_5$ - Os (open triangle) than on those made with $PVI_3$ - Os (filled triangles).

Depth of the Recess and the Sensing Layer

Figure 3:
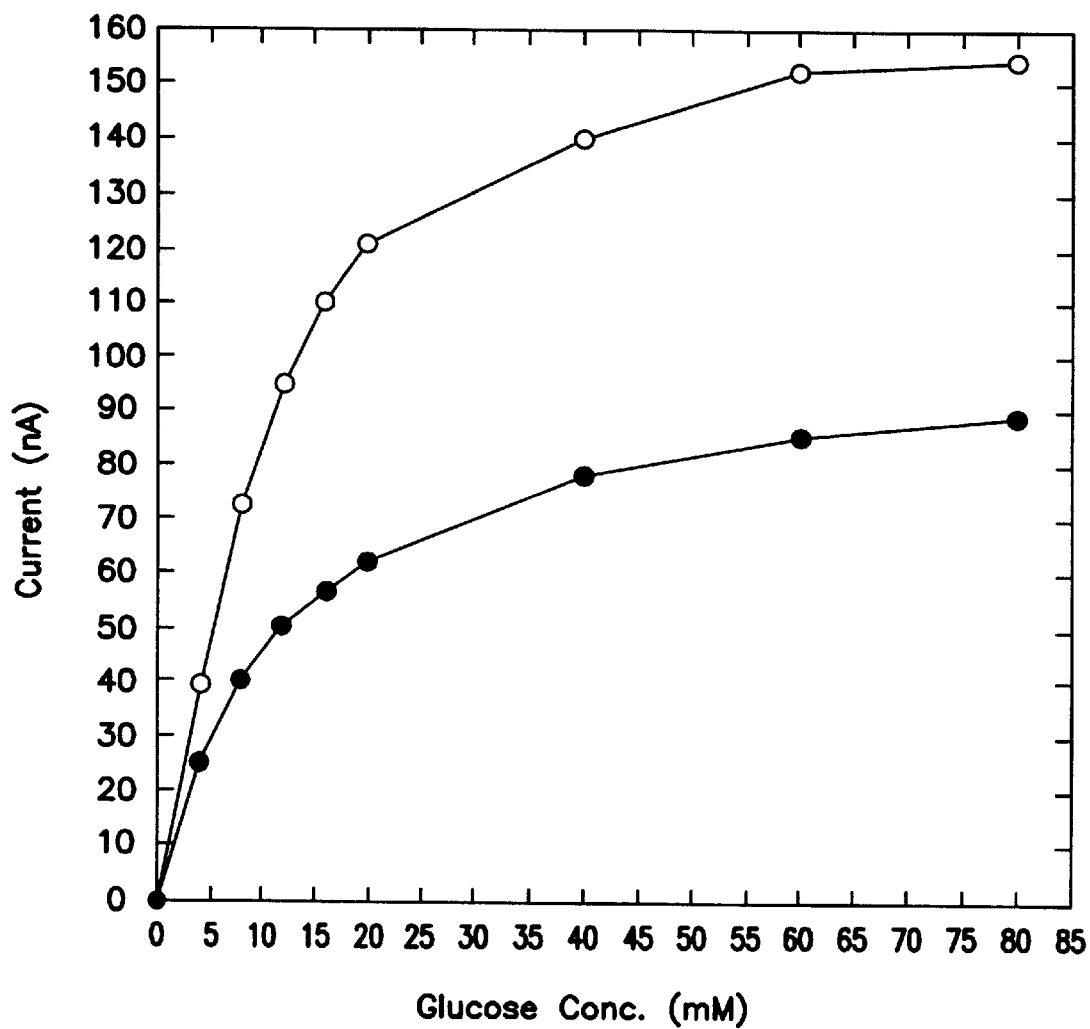
FIG. 3 is a graphical representation of data generated comparing dependency of current generated on the depth of the recess.
Figure 4:
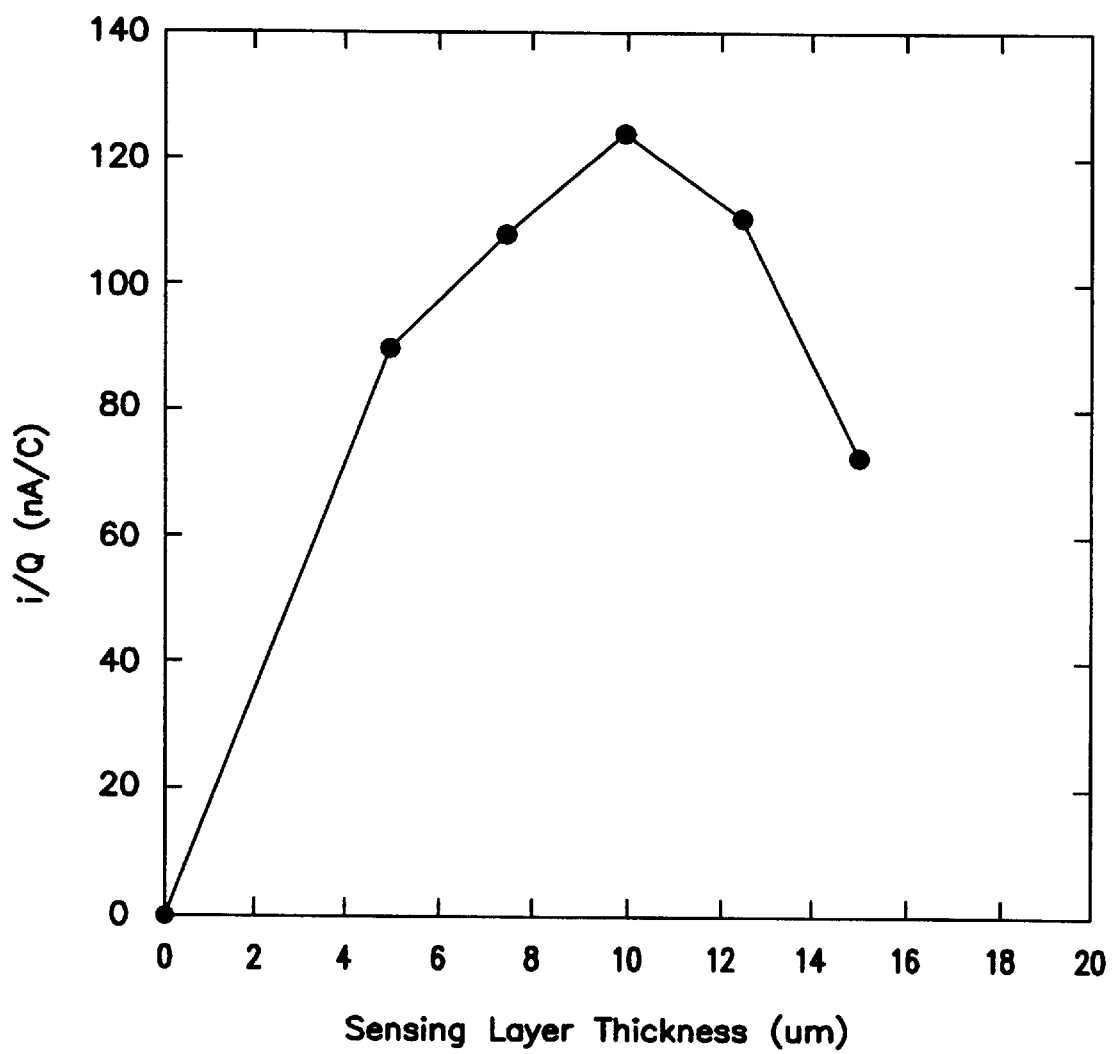
FIG. 4 is a graphical representation of data generated comparing dependency of the ratio of the current generated and the charge required to electoreduce or oxidize the polymer redox centers in the sensing layer on the thickness of the sensing layer.

Channels of 125, 250, and 500 µm depth, were investigated to assess the dependence of the current on the depth of the recess (FIG. 3), with the total amount of $PVI_5$ - Os and rGOX being kept constant. Much of the loss in current in the deeper cavities resulted not from reduced glucose mass transport, but from adsorptive retention of part of the enzyme and polymer on the polyamide wall when microdrops of the component solutions were introduced into the recess in the process of making the electrodes. Through repeated rinsing with water, some of the adsorbed polymer and enzyme on the walls were washed onto the electrode surface, increasing the current. The highest currents were seen after five washings. When the thickness of the sensing layer was increased through increasing the number of coatings (FIG. 4) the ratio of current to charge required to electroreduce or electrooxidize the redox polymer in the sensing layer reached a maximum, then dropped. For the preferred 125 µm recess, 10 coatings, producing an approximately 13 µm thick wired-rGOX sensing layer, yielded sensors that had the desired characteristics for in vivo use.

The Insulating Layer

This layer electrically insulates the redox enzymes of the interference eliminating layer (HRP and LOX) from the "wired" rGOX layer and limits the glucose flux to the sensing layer, thereby extending the useful life of the electrode. PAL crosslinked with PAZ, forming a polycationic network at pH 7.09 is preferred. The best results, i.e., best stability of current outputs, were obtained using 1:2 PAL-:PAZ (FIG. 5), with three coatings applied to form an approximately 7 $\mu$m thick crosslinked film.

The Interference Eliminating Layer

Figure 6:
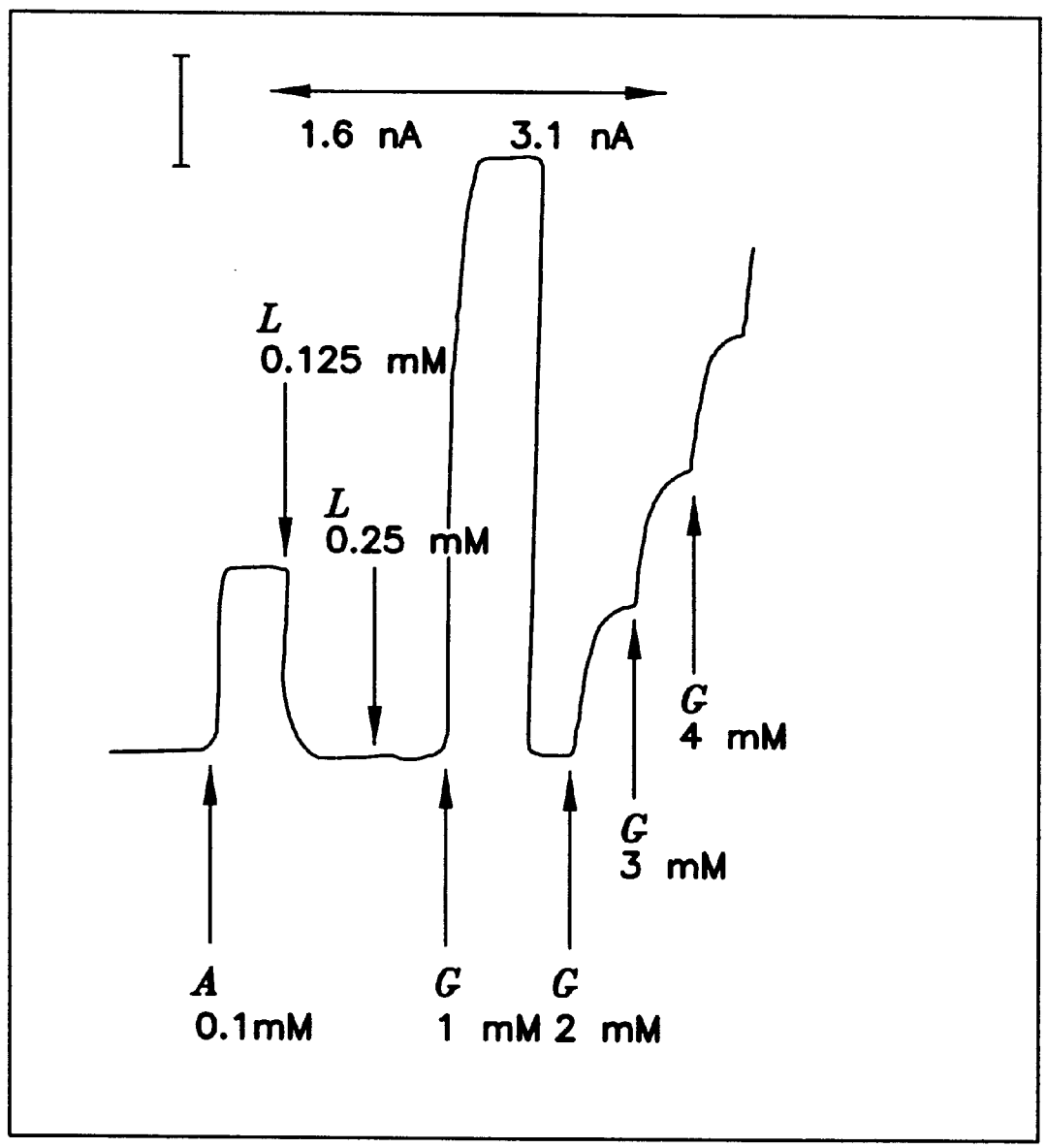
FIG. 6 is a graphical representation of data generated comparing dependency of current generated on the presence of ascorbate, in the absence and presence of lactate and glucose. The concentrations of ascorbate (A), lactate (L) and glucose (G) are shown. Ascorbate is an electrooxidzable interferant. Upon addition of lactate its electrooxidation current is suppressed while that of glucose is not suppressed.

Interferants, particularly ascorbate, urate, and acetaminophenol, are oxidized in the third layer, containing LOX and HRP. In this layer, lactate, the typical concentration of which in blood is 1 mM, reacts with $O_2$ to form $H_2O_2$ and pyruvate. $H_2O_2$, in the presence of HRP, oxidizes ascorbate, urate, and acetaminophenol, being reduced to water. The preferred coimmobilization process involved two separate steps: periodate oxidation of oligosaccharide functions of HRP to aldehydes, followed by mixing with LOX and formation of multiple Schiff bases between HRP-aldehydes and LOX amines (e.g. lysines) and between HRP aldehydes and amines. The thickness of the interference eliminating layer is approximately 85 $\mu$m and is made by applying successive coatings, e.g., about six coatings. FIG. 6 shows that electrooxidizable interferants were eliminated in the presence of lactate at physiological levels. LOX slowly lost its activity in the crosslinked HRP-LOX layer. This led to degradation of the ability of the layer to eliminate interferants. After 36 hours of operation at 37° C., a measurable current increment was noted when enough ascorbate was added to produce a 0.1 mM concentration.

The Biocompatible Layer

A preferred biocompatible layer consists, for example, of photocrosslinked tetraacrylated 18,500 Da poly(ethylene oxide) (Pathak et al., 1993, *J. Am. Chem. Soc.*, 114:8311–8312). The thickness of this layer, made by sequential photo-crosslinking of two coatings, is about 20 $\mu$m. One minute UV exposure required for the photo-crosslinking process reduced the sensitivity by 16±2%.

Example 2

In vivo Use of Sensor

The objective of this experiment was to establish the validity of a one-point in vivo calibration. Two sensors were simultaneously implanted subcutaneously in a rat, one on the thorax, the second between the scapulae. To make the difference between the blood sampled and the subcutaneous fluid proved with the sensors as extreme as possible, i.e., to probe whether the one-point calibration holds even if the organs sampled are different and the sampling sites are remote, blood was withdrawn from the tail vein. Blood glucose levels were periodically measured in withdrawn samples, while the absolute uncorrected sensor current output was continuously monitored.

In vivo experiments (6–10 hours) were carried out in 300 g male Sprague-Dawley rats. The rats were fasted overnight and prior to the experiment were anaesthetized with an intraperitoneal (i.p.) injection of sodium pentobarbital (65 mg/kg rat wt). An i.p. injection of atropine sulfate (166 mg/kg rat wt) was then administered to suppress respiratory depression. Once the rat was anaesthetized, a portion of the rat's abdomen was shaved, coated with a conductive gel, and an Ag/AgCl surface skin reference electrode was attached. This electrode served also as the counter electrode. Sensors were then implanted subcutaneously using a 22 gauge Per-Q-Cath Introducer (Gesco International, San Antonio, Tex.) on the rat's thorax, or subcutaneously in the intrascepular area through a small surgical incision. The sensors were taped to the skin to avoid sensor movement. The sensors, along with the reference electrode, were connected to an in-house built bipotentiostat. The operating potential of the sensors was 0.3 V vs. Ag/AgCl, with the Ag/AgCl electrode serving as both the reference counter electrode. Sensor readings were collected using a data logger (Rustrak Ranger, East Greenwich, R.I.) and at the end of the experiment were transferred to a computer. During the experiment, the rat's body temperature was maintained at 37° C. by a homeostatic blanket. The sensors were allowed to reach a basal signal level for at least one hour before blood sampling was started. Blood samples were obtained from the tail vein and all blood samples were analyzed using a glucose analyzer (YSI, Inc., Yellow Springs, Ohio; Model 23A).

Approximately thirty minutes after the start of blood sampling, an i.p. glucose infusion was started using a syringe pump (Harvard Apparatus, South Natick, Mass.) at a rate of 120 mg glucose/min kg rat wt. The glucose infusion was maintained for approximately one hour.

Figure 7:
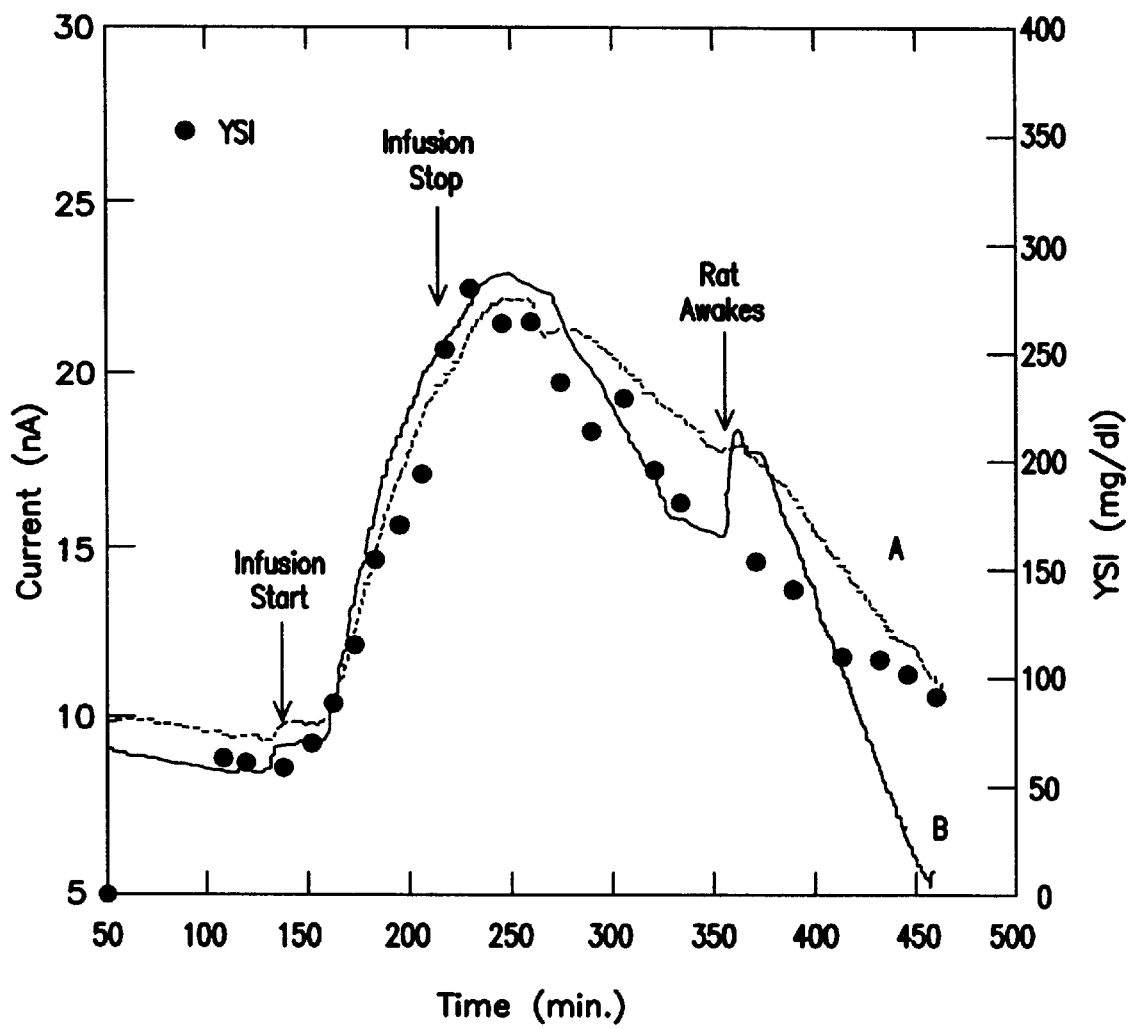
FIG. 7. is a graphical representation of data showing current density and corresponding subcutaneous glucose concentration measured with the subcutaneously implanted electrodes of the present invention in a rat animal model. Large solid circles show blood glucose concentrations measured on withdrawn blood samples using a YSI analyzer.
Figure 8:
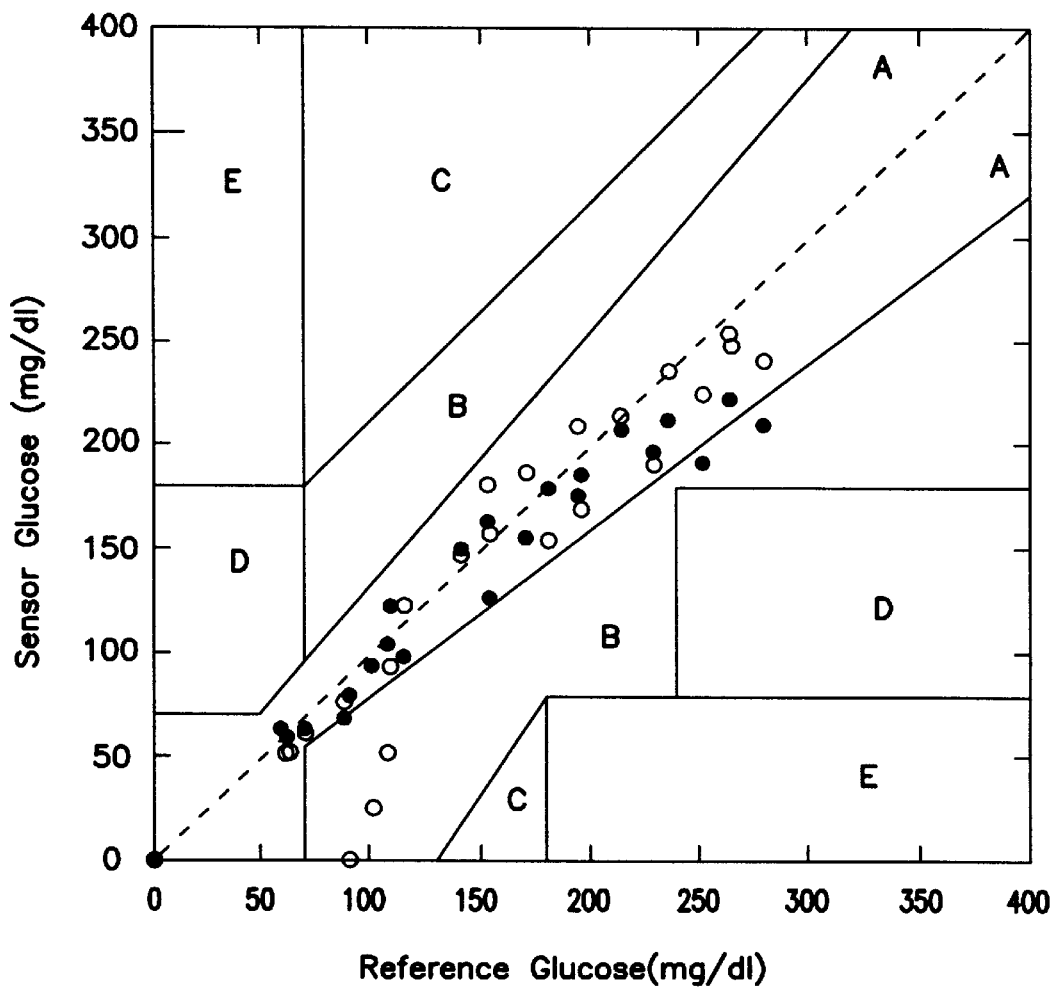
FIG. 8 is a Clarke-type clinical grid analyzing the clinical relevance of the blood glucose measurements of FIG. 7.

As seen in FIG. 7, at 410 min the current dropped precipitously. Such a drop was observed in other measurements with subcutaneously implanted electrodes between 400 and 600 min, but was never observed in electrodes operated in buffer at 37° C. When the failed electrodes were withdrawn and retested in buffer, most of their original sensitivity was found to be intact. The cause for this apparent deactivation was failure of the counter/reference Ag/AgCl electrode on the rat's skin to make good electrolytic contact, and was not due to any failure of the implanted sensor. Using an arbitrarily chosen point to calculate a calibration curve for each electrode, i.e., one blood glucose level determination and one current measurement to establish the scales, all the data from FIG. 7 were plotted in a Clarke-type, (Clarke et al., 1987, *Diabetes Care*, 5:622–627) clinical grid (FIG. 8), without further correction. In this analysis, points falling in region A of the grid are considered clinically accurate, while those in region B are considered clinically correct. Points falling in region C are not correct, but would not lead to improper treatment. Points in regions D and E are incorrect and if treatment would rely on these, it would be improper.

All of the points, from both electrodes, were in regions A and B, with 43 of the 48 points being in region A. The three points in region B near 100 mg/dl glucose, for the electrode implanted between the scapulae, were the last three points of the experiment, at about 410 min. Notwithstanding the failure mode at 400–600 min because of poor electrolytic contact of the counter/reference electrode with the skin and failure after 36 hours by deactivation of the lactate oxidase, resulting in loss of interference elimination, one-point calibration is shown here to be practical. After such calibration, the readings of the subcutaneous sensors provide, without any correction, clinically useful estimates of blood glucose levels.

Figure 9:
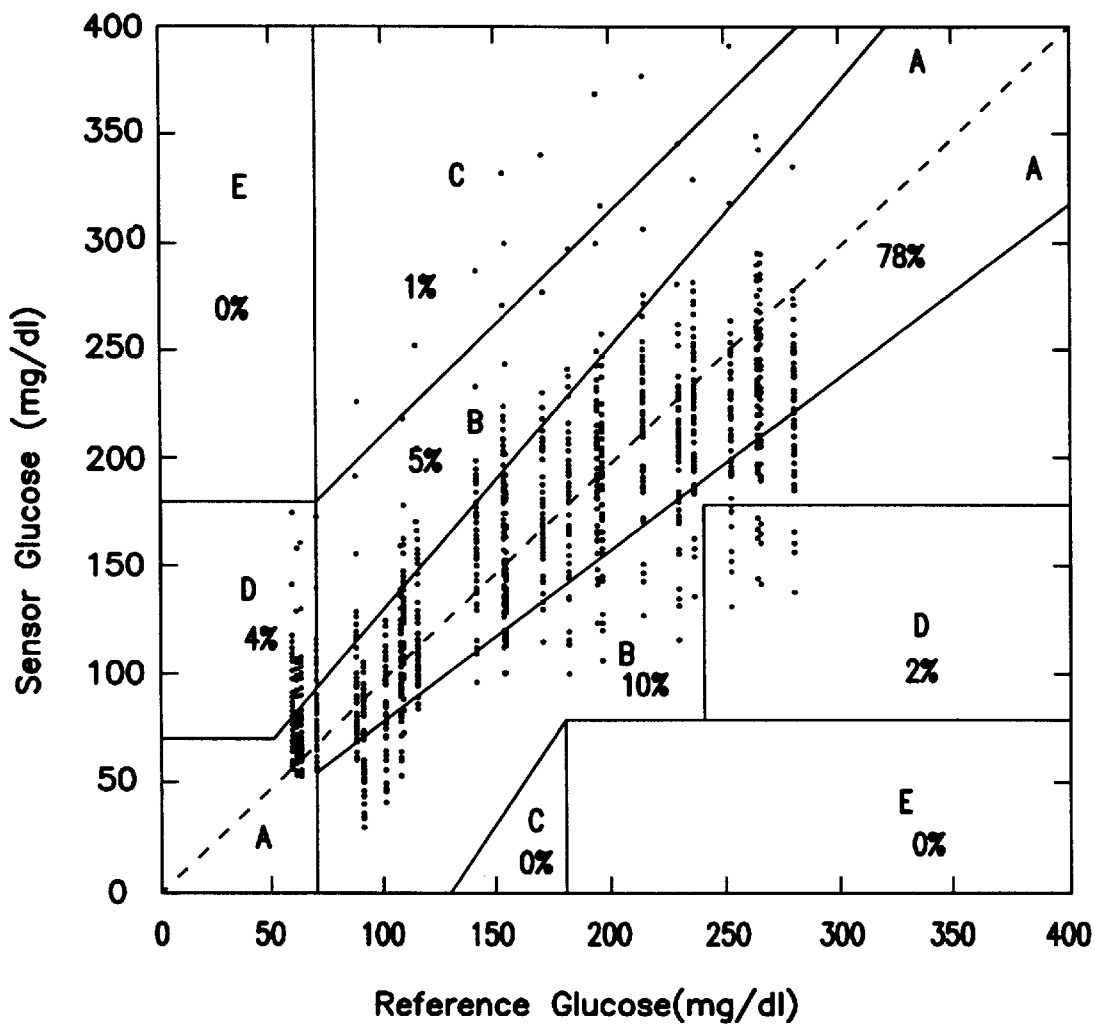
FIG. 9 is a Clarke-type clinical grid of all possible correlations obtained when each of the 24 glucose analyses of FIG. 7 were used for single point calibration of either implanted electrode.

FIG. 9 shows the distribution of all possible correlations obtained when each of the 24 glucose analyses was used for single point calibration of either implanted electrode. There are 2×24×24=1152 points in the distribution. Of these, 78% are in region A, 15% are in region B, 1% in region C, 6% are in region D, and no points are in region E.

Figure 10:
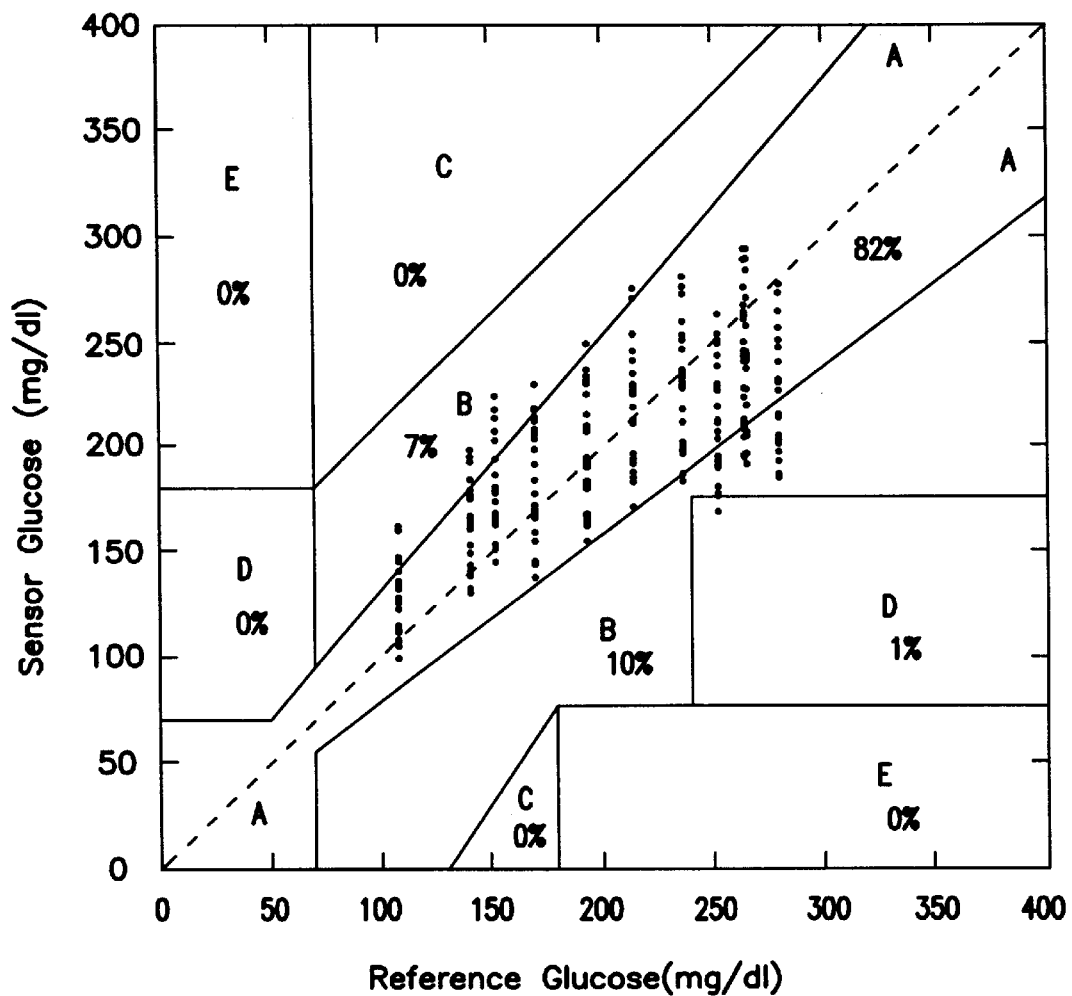
FIG. 10 is a Clarke-type clinical grid testing improvement of the single point calibration through redundant electrodes, the readings of which were within the standard deviation calculated for all differences between simultaneous readings by a pair of implanted electrodes.

In FIG. 10, we tested for the improvement of the single point calibration through using redundant electrodes. First, the readings of electrode A were normalized with respect to those of electrode B by multiplying each reading by the average output of electrode B divided by the average output of electrode A. Next the standard deviation was calculated for the differences between the 24 sets of readings of implanted electrode B and corrected readings of implanted electrode A. Then, all those sets of readings that differed by more than the standard deviation were rejected. The number of sets was reduced thereby from 24 to 11; 82% of the points were in region A, 17% in region B, 1% in region D, and no points in regions C and E. The distribution demonstrates that the sensors can be calibrated through a single independent measurement of the glucose concentration in a withdrawn blood sample. They also demonstrate the improvement in clinical accuracy resulting from the use of redundant subcutaneous sensors. The selection of those data points that differed by less than the standard deviation for the entire set led to a sixfold reduction in the probability of clinically erring in a decision based on readings of the implanted sensors.

Stability and Other Characteristics

In order to improve the stability, more thermostable recombinant GOX, (rGOX; Heller, 1992, *J. Phys. Chem.*, 96:3579–3587) rather than GOX is used in the sensor and glucose transport is reduced to make the sensor current diffusion, not enzyme turnover, limited. The glucose flux is attenuated by the three outer layers and the sensing layer itself. Because the sensing layer contains a large excess of glucose oxidase, its activity greatly exceeds that needed for electrooxidizing the attenuated glucose flux, and the sensor's stability is improved.

The stability can be tested by methods known, for example, tested in the presence of 0.1 mM ascorbate in 10 mM glucose at 37° C. The current output of a typical optimized electrode was about 35 nA and the apparent $K_m$, derived from an Eadie-Hofstee plot, was about 20 mM (Table 1). The 10–90% response time was approximately one minute.

Figure 5:
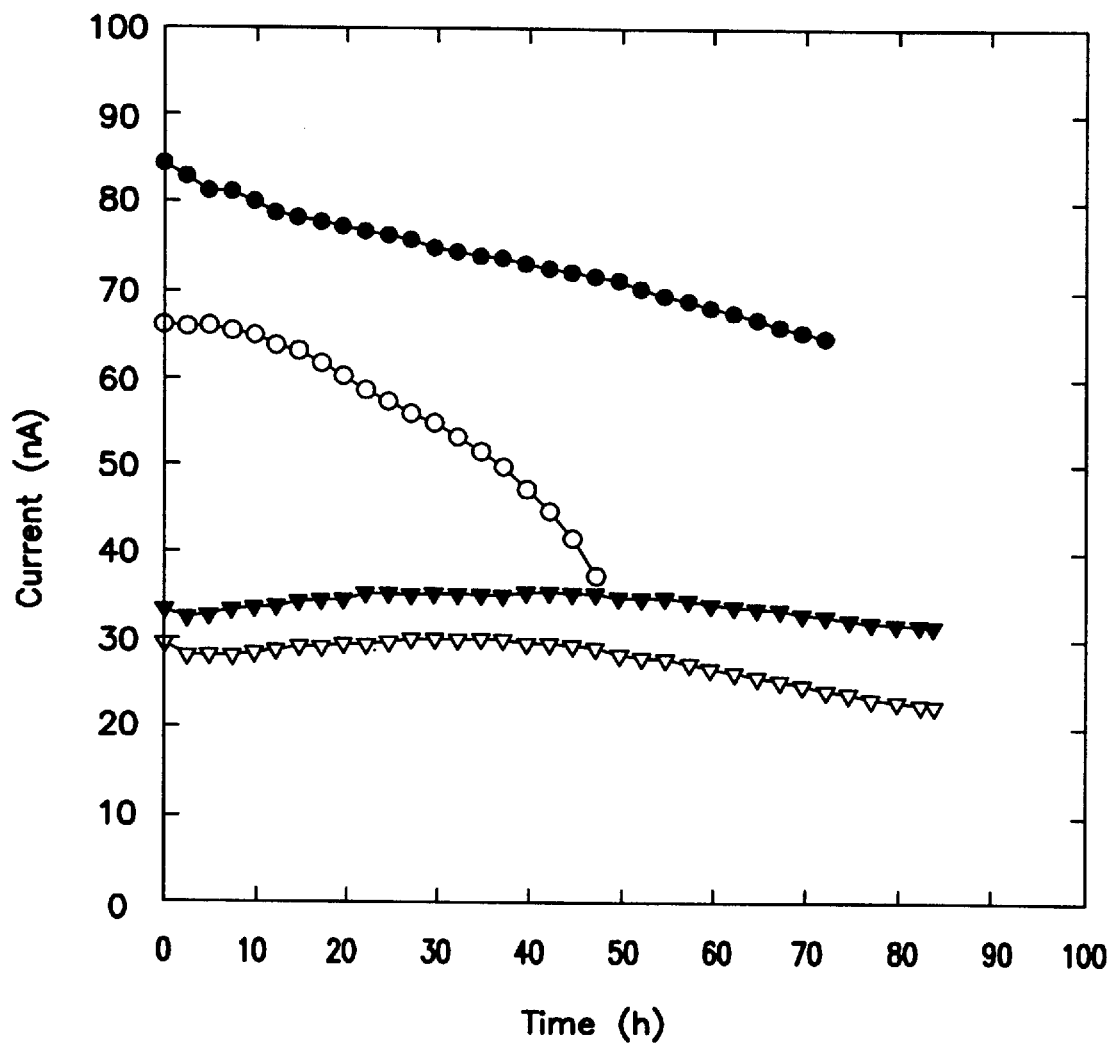
FIG. 5 is a graphical representation of data generated comparing variation of current generated by electrodes having sensing layers of differing thickness and diffusion limiting layers of different compositions and thickness. Solid circles: 7.5 $\mu$m thick sensing layer of $PVI_5$-Os (52%), rGOX (35%), PEGDGE (13%), coated with 4 $\mu$m PAL/PAZ (1:1 ratio). Open circles: 5.0 sensing layer. Solid triangles: 12.5 $\mu$m sensing layer and 7 $\mu$m PAL/PAZ (1:2 ratio). Open triangles: 7.5 $\mu$m sensing layer and 4.5 $\mu$m PAL/PAZ (1:2 ratio).

As expected, and as can be seen in FIG. 5, with thinner films the glucose mass transport was increased, i.e., the current was higher, while for thicker films the stability was improved. Because of the high sensitivity of thin sensing film (approximately 1 μm) electrodes (less than $10^{-2} A\, cm^{-2}\, M^{-1}$), an order of magnitude decrease in sensitivity could be traded for stability, while the currents remained high enough to be easily measured.

As seen in FIG. 5, the sensitivity of the stabilized sensors does not change by more than ±5% for 72 hours of operation at 37° C. After a small initial decrease in sensitivity, it increased to a maximum after 40 hours and the final 72 hour sensitivity was almost identical with the initial.

The characteristics of the electrodes of the present invention are summarized in Table 1. Each entry represents an average value for five tested electrodes. Baseline currents are typically less than 0.5 nA and the noise less than 10 pA. The currents observed throughout the physiological glucose concentration range (2–20 mM) exceed the noise equivalent current by at least a factor of 100. The apparent $K_m$ is 20 mM, and the 10% to 90% response time is, for aged electrodes, about 90 seconds at the lowest physiologically relevant glucose concentration (2 mM) and 20 seconds at the highest (20 mM).

The baseline of nil at 0 mM glucose is stable for 36 hours in the presence of 0.1 mM ascorbate. The stability observed and the existence of a valid zero-point in the presence of interferants suggest that the sensor can be used in vivo for 72 hours and tested/recalibrated in vivo through a single point calibration, i.e., by withdrawing only a single sample of blood for independent analysis.

TABLE 1

SENSOR CHARACTERISTICS

| i(nA) | j(μA/cm²) | $K_M^{app}$(mM) EH | $K_M^{app}$(mM) LB | $t_r$(s) | Current Variance (%) |
|---|---|---|---|---|---|
| 33.9 | 69.1 | 18.5 | 33.4 | 30–90 | 5.0 | where:
i is the current measured at 37° C. and at 10 mM glucose concentration
j is the current density measured at 37° C. at 10 mM glucose concentration
$K_M^{app}$ is the apparent Michaelis-Menten coefficient determined from an electrochemical Eadie-Hoffstee (EH) of Lineweaver-Burk (LB) plot
$t_r$ is the 10–90% risetime, 90s for 2 mM and 30 s for 20 mH glucose concentration.
Current Variance is the maximum deviation from the mean value, measured during the 72 hour test, conducted in 10 mM glucose in the presence of interferants. The current was continuously monitored at 37° C.

The foregoing examples are designed to illustrate certain aspects of the present invention. The examples are not intended to be comprehensive of all features and all embodiments of the present invention, and should not be construed as limiting the claims presented herein.

We claim:

1. An electrochemical sensor comprising:
   one or more non-corroding metal or carbon electrodes;
   a sensing layer comprising an enzyme coupled to each electrode; and
   a biocompatible layer comprising a biocompatible hydrogel chemically bound to the sensing layer of each electrode.

2. The electrochemical sensor of claim 1, wherein the biocompatible layer is indirectly chemically bound to the sensing layer.

3. The electrochemical sensor of claim 2, wherein the sensor further comprises an interferent eliminating layer or an analyte flux limiting layer or both and the biocompatible layer is chemically bound to the interferent eliminating layer or the analyte flux limiting layer.

4. An analyte measurement system comprising:
   an electrochemical sensor including two or more non-corroding metal or carbon electrodes, each electrode adapted for subcutaneous implantation in an animal, and a non-leachable analyte-responsive enzyme disposed on each of the electrodes; and
   a device for comparing signals generated at the two or more electrodes.

5. An electrochemical sensor comprising:
   one or more non-corroding metal or carbon electrode;
   a sensing layer coupled to each electrode wherein the sensing layer comprises a non-leachable redox enzyme; and
   a microfiltration device for transporting a fluid sample into contact with the sensing layer of at least one of the electrodes.

6. The electrochemical sensor of claim 5, wherein the microfiltration device comprises a microfiltration fiber or a microdialysis membrane.

7. The electrochemical sensor of claim 5, wherein the electrochemical sensor is adapted for implantation in the body of an animal, the sensor comprising a redox compound and the redox enzyme which are both non-leachable by fluids in the body of the animal at a pH between about 6.5 and about 7.8.

8. The electrochemical sensor of claim 7, wherein the sensor is configured and arranged so that when the sensor is implanted in the body of an animal, only animal fluids containing the sample will be transported by the microfiltration device to the sensor.

9. An electrochemical sensor for measuring an analyte in an animal, comprising:
  one or more analyte responsive electrodes, at least one of said analyte-responsive electrodes adapted for subcutaneous implantation in an animal, each of the analyte responsive electrodes comprising
    a non-corroding metal or carbon electrode, and
    a sensing layer covering at least a portion of each non-corroding metal or carbon electrode, comprising a redox enzyme and a redox compound,
    wherein the redox enzyme and redox compound are non-leachable by fluids in the body of the animal at a pH of between about 6.5 and about 7.8.

10. The electrochemical sensor of claim 9, wherein the redox compound comprises a non-leachable redox polymer.

11. The electrochemical sensor of claim 10, wherein the redox polymer is a crosslinked redox polymer.

12. The electrochemical sensor of claim 11, wherein the redox polymer is crosslinked with the redox enzyme.

13. The electrochemical sensor of claim 9, wherein the redox compound comprises a metal ion selected from the group consisting of $Os^{3+/2+}$, $Ru^{3+/2+}$, and $Fe^{3+/2+}$.

14. The electrochemical sensor of claim 13, wherein the metal ion is $Os^{3+/2+}$.

15. The electrochemical sensor of claim 13, wherein the metal ion is $Ru^{3+/2+}$.

16. The electrochemical sensor of claim 13, wherein the metal ion is bound to a polymer.

17. The electrochemical sensor of claim 16, wherein the polymer is poly(1-vinylimidazole) or a copolymer of 1-vinylimidazole.

18. The electrochemical sensor of claim 16, wherein the metal ion is bound to the polymer by electrostatic or ionic bonding.

19. The electrochemical sensor of claim 16, wherein the metal ion is bound to the polymer by covalent bonding.

20. The electrochemical sensor of claim 16, wherein the metal ion is bound to the polymer by coordinative bonding.

21. The electrochemical sensor of claim 9, wherein the redox potential of the redox compound is not more reducing than about −0.15 V and not more oxidizing than about +0.15 V versus the standard calomel electrode in an aqueous solution at about pH 7.4.

22. The electrochemical sensor of claim 9, wherein the redox potential of the redox compound is substantially invariant in a pH range of between about 6.5 and 7.8.

23. The electrochemical sensor of claim 9, wherein the one or more non-corroding metal or carbon electrodes are flexible.

24. The electrochemical sensor of claim 9, wherein the electrochemical sensor further comprises a biocompatible layer covering the sensing layer of each non-corroding metal or carbon electrode.

25. The electrochemical sensor of claim 24, wherein the biocompatible layer comprises repeating units of ethylene oxide.

26. The electrochemical sensor of claim 9, wherein the electrochemical sensor further comprises an analyte flux limiting layer over the sensing layer of at least one of the one or more non-corroding metal or carbon electrodes.

27. The electrochemical sensor of claim 9, wherein the electrochemical sensor further comprises an electrically insulating polymer coating at least a part of one of the one or more non-corroding metal or carbon electrodes.

28. The electrochemical sensor of claim 27, wherein the electrically insulating polymer is selected from the group consisting of polyimide, polyester, polyurethane, and perfluorinated polymer.

29. The electrochemical sensor of claim 9, wherein the outer diameter of each of the one or more non-corroding metal or carbon electrodes is smaller than about 0.3 mm.

30. The electrochemical sensor of claim 9, wherein the sensor further comprises an interference eliminating layer covering the sensing layer of each non-corroding metal or carbon electrode.

31. The electrochemical sensor of claim 30, wherein the interference eliminating layer comprises a peroxidase enzyme.

32. The electrochemical sensor of claim 9, wherein the sensitivity of the sensor does not change by more than about ±5% for 72 hours of operation at 37° C.

33. The electrochemical sensor of claim 9, wherein the sensitivity of the sensor does not change by more than about ±5% for 8 hours of operation at 37° C.

34. The electrochemical sensor of claim 9, wherein the sensor further comprises one or more reference or reference/counter electrodes, at least one of the reference or reference/counter electrodes adapted for placement on the surface of the animal.

35. The electrochemical sensor of claim 9, wherein each non-corroding metal or carbon electrode is substantially coated with an electrically insulating polymer and has a gap or recess in the coating exposing a bare, non-insulated surface of the electrode, the insulating polymer containing less than 5% water by weight when in equilibrium with physiological body fluids at about 37° C.

36. The electrochemical sensor of claim 35, wherein the exposed electrode is recessed in the insulating polymer coat forming a channel in the insulating polymer coat.

37. The electrochemical sensor of claim 36, wherein the channel has a depth ranging from about 20 microns to about 1 mm.

38. The electrochemical sensor of claim 9, further comprising
  one or more alarms, each alarm coupled to one or more of the non-corroding metal or carbon electrodes.

39. The electrochemical sensor of claim 38, wherein one or more of the alarms is configured to activate if a signal generated at one of the electrodes coupled to the alarm is outside a predetermined range.

40. The electrochemical sensor of claim 38, wherein at least one of the alarms is configured to activate if a signal generated at the electrode indicates a blood glucose concentration above a predetermined concentration.

41. The electrochemical sensor of claim 38, wherein at least one of the alarms is configured to activate if a signal generated at the electrode indicates an increase in glucose concentration with time over a predetermined rate.

42. The electrochemical sensor of claim 38, wherein at least one of the alarms is configured to activate if a signal generated at the electrode indicates a changing glucose concentration that accelerates over time above a predetermined acceleration.

43. The electrochemical sensor of claim 38, wherein at least one of the alarms is configured to activate if a signal generated at the electrode indicates a blood glucose concentration below a predetermined concentration.

44. The electrochemical sensor of claim 38, wherein at least one of the alarms is configured to activate if a signal generated at the electrode indicates a decrease in glucose concentration with time over a predetermined rate.

45. The electrochemical sensor of claim 38, wherein at least one of the alarms is configured to activate if a signal generated at the electrode indicates hypoglycemia or impending hypoglycemia.

46. The electrochemical sensor of claim 38, wherein at least one of the alarms is configured to activate if a signal generated at the electrode indicates hyperglycemia or impending hyperglycemia.

47. The electrochemical sensor of claim 38, wherein the sensor of the system comprises two or more non-corroding metal or carbon electrodes and one or more alarms each coupled to two or more of the non-corroding metal or carbon electrodes.

48. The electrochemical sensor of claim 47, wherein at least one of the alarms is configured to activate if any two of the non-corroding metal or carbon electrodes to which the alarm is coupled generate electrical signals that differ by greater a predetermined amount for a predetermined period of time.

49. The electrochemical sensor of claim 47, wherein at least one of the alarms is configured to activate if any two of the non-corroding metal or carbon electrodes to which the alarm is coupled generate electrical signals that differ by greater than about 10% for a predetermined period of time.

50. The electrochemical sensor of claim 47, wherein at least one of the alarms is configured to activate if any two of the non-corroding metal or carbon electrodes to which the alarm is coupled generate electrical signals that differ by greater than about one standard deviation for a predetermined period of time.

51. The electrochemical sensor of claim 48, wherein the predetermined period of time is greater than about 10 minutes.

52. A method of calibrating an electrochemical sensor, comprising the steps of:
  withdrawing a single calibration sample from an animal;
  assaying an analyte concentration of the single calibration sample; and
  correlating the assayed analyte concentration to a signal generated by one or more implanted working electrodes of an electrochemical sensor, each working electrode having an analyte-responsive enzyme disposed thereon.

53. The method of claim 52, wherein the sensor is an electrochemical sensor for measuring an analyte in an animal, comprising: one or more analyte responsive electrodes, at least one of said analyte-responsive electrodes adapted for subcutaneous implantation in an animal, each of the analyte responsive electrodes comprising
  a non-corroding metal or carbon electrode, and
  a sensing layer covering at least a portion of each non-corroding metal or carbon electrode, comprising a redox enzyme and a redox compound;
  wherein the redox enzyme and redox compound are non-leachable by fluids in the body of the animal at a pH of between about 6.5 and about 7.8.

54. A method of measuring the concentration of a biochemical in an animal comprising:
  contacting body fluid of the animal with the electrochemical sensor of claim 9 to generate an electrical signal; and
  determining from the generated electrical signal the concentration of a biochemical in the body fluid.

55. The method of claim 54, wherein the body fluid is blood, plasma, or serum.

56. The method of claim 54, wherein the measuring is intermittent.

57. The method of claim 54, wherein the contacting includes implanting the electrode subcutaneously in the animal.

58. The method of claim 54, further comprising placing a reference electrode or combined reference and counter electrode on or in the skin of the animal.

59. The method of claim 54, wherein the biochemical to be detected is glucose.

60. The method of claim 54, wherein the biochemical to be detected is lactate.

61. The method of claim 54, wherein the sensor is capable of being calibrated by the method of claim 52.

62. The method of claim 54, wherein the sensor has two or more non-corroding metal or carbon electrodes and substantially simultaneous readings of the two or more non-corroding metal or carbon electrodes are accepted as correctly measuring the concentration of the biochemical when the two or more readings do not differ by more than a specified percentage of the measured electrical signals.

63. The method of claim 56, wherein the sensor has two or more non-corroding metal or carbon electrodes and readings of the two or more non-corroding metal or carbon electrodes that do not differ by more than about 20% or by more than about one standard deviation are accepted as correctly measuring the concentration of the biochemical.

64. A method for the analysis of a bioanalyte, comprising:
  providing an analyte measurement system comprising two or more subcutaneously implantable electrodes;
  subcutaneously implanting two or more electrodes in the body of an animal;
  obtaining readings from each of the electrodes at substantially one point in time;
  comparing two or more of the readings from the electrodes; and
  accepting those readings which do not vary by more than a predetermined degree.

65. The method of claim 64, wherein the analyte measurement system is an analyte measurement system comprising:
  an electrochemical sensor including two or more non-corroding metal or carbon electrodes, each electrode adapted for subcutaneous implantation in an animal, and a non-leachable analyte-responsive enzyme disposed on each of the electrodes; and a device for comparing signals generated at the two or more electrodes.

66. The method of claim 64, wherein the readings are obtained continuously.

67. The method of claim 64, wherein the readings are obtained intermittently.

68. The method of claim 64, wherein the method further comprises
  measuring a temperature near one or more electrodes at substantially the same point in time as obtaining the readings from the electrodes, and
  correcting the readings from the electrodes based on the measured temperature.

69. The method of claim 64, wherein the sensor is capable of calibration by a method of calibrating an electrochemical sensor, comprising the steps of:

withdrawing a single calibration sample from an animal;

assaying an analyte concentration of the single calibration sample; and correlating the assayed analyte concentration to a signal generated by one or more implanted working electrodes of an electrochemical sensor, each working electrode having an analyte-responsive enzyme disposed thereon.

70. The method of claim 52, wherein a baseline current of the one or more working electrodes is 0.5 nA or less.

71. The method of claim 52, wherein a baseline current is 1.5% or less of a total current of the one or more working electrodes at 10 mM analyte concentration.

72. The method of claim 52, wherein a baseline current is 5% or less of a total current of the one or more working electrodes over a physiological analyte concentration range.

73. The method of claim 52, wherein the one or more working electrodes are subcutaneously implanted.

74. The electrochemical sensor of claim 9, further comprising one or more reference or reference/counter electrodes, at least one of said reference or reference/counter electrodes adapted for placement on the surface of the animal.

* * * * *

UNITED STATES PATENT AND TRADEMARK OFFICE
CERTIFICATE OF CORRECTION

PATENT NO.   : 6,284,478 B1
DATED        : September 4, 2001
INVENTOR(S)  : Heller et al.

It is certified that error appears in the above-identified patent and that said Letters Patent is hereby corrected as shown below:

Title page,
Item [63], Related U.S. Application Data, after "Pat. No. 5,356,786" insert -- , which is a continuation of U.S. Patent Application having Serial No. 07/664,054 filed March 4, 1991, now abandoned --.

Column 1,
Line 7, after "Pat No. 5,536,786, insert -- which is a continuation of U.S. Patent Application having Serial No. 07/664,054 filed March 4, 1991, now abandoned --

Signed and Sealed this

Eleventh Day of February, 2003

JAMES E. ROGAN
*Director of the United States Patent and Trademark Office*

(12) EX PARTE REEXAMINATION CERTIFICATE (7085th)
United States Patent
Heller et al.

(10) Number: US 6,284,478 C1
(45) Certificate Issued: Sep. 29, 2009

(54) SUBCUTANEOUS GLUCOSE ELECTRODE

(75) Inventors: Adam Heller, Austin, TX (US); Michael V. Pishko, Austin, TX (US)

(73) Assignee: Abbott Diabetes Care, Inc.

Reexamination Request:
No. 90/007,913, Feb. 1, 2006
No. 90/008,665, May 25, 2007

Reexamination Certificate for:
Patent No.: 6,284,478
Issued: Sep. 4, 2001
Appl. No.: 08/767,110
Filed: Dec. 4, 1996

Certificate of Correction issued Feb. 11, 2003.

Related U.S. Application Data

(63) Continuation of application No. 08/299,526, filed on Sep. 1, 1994, now Pat. No. 5,593,852, which is a continuation-in-part of application No. 08/161,682, filed on Dec. 2, 1993, now Pat. No. 5,356,786, which is a continuation of application No. 07/664,054, filed on Mar. 4, 1991, now abandoned.

(51) Int. Cl.
*C12Q 1/00* (2006.01)

(52) U.S. Cl. .................. 435/14; 435/4; 435/25; 435/28; 435/288.5; 435/817; 436/63; 436/149; 204/403.1; 204/403.13; 204/403.14; 204/403.15; 205/778; 600/345; 600/347

(58) Field of Classification Search .......... None
See application file for complete search history.

(56) References Cited

U.S. PATENT DOCUMENTS

| | | |
|---|---|---|
| 2,402,306 A | 6/1946 | Turkel |
| 3,132,123 A | 5/1964 | Harris, Jr. et al. |
| 3,219,533 A | 11/1965 | Mullins |
| 3,260,656 A | 7/1966 | Ross, Jr. |
| 3,282,875 A | 11/1966 | Connolly et al. |
| 3,304,413 A | 2/1967 | Lehmann et al. |
| 3,310,606 A | 3/1967 | Fritz |
| 3,397,191 A | 8/1968 | Beckerbauer |

(Continued)

FOREIGN PATENT DOCUMENTS

| | | |
|---|---|---|
| EP | 0010375 | 4/1980 |
| EP | 1579690 | 11/1980 |
| EP | 0026995 | 4/1981 |
| EP | 0048090 | 3/1982 |
| EP | 0078636 | 5/1983 |
| EP | 0080304 | 6/1983 |
| EP | 0 098 592 | 1/1984 |
| EP | 0107634 | 5/1984 |

(Continued)

OTHER PUBLICATIONS

W. Reusch, Virtual Textbook of Organic Chemistry, Speacial Topics: Organometallic Chemistry pp. 1–25, copyright 1999; latest revison 2004.*
Sternberg et al., Biosensors, 4:27–40, 1988.*
Wade, Organic Chemistry, 5th Edition, pp. 762–763, 2003.*
Heller, "Electrical Connection of Enzyme Redox Centers to Electrodes", J. Phys. Chem. vol. 96, pp. 3579–3587, 1992.*

(Continued)

*Primary Examiner*—Dwayne C Jones

(57) ABSTRACT

A small diameter flexible electrode designed for subcutaneous in vivo amperometric monitoring of glucose is described. The electrode is designed to allow "one-point" in vivo calibration, i.e., to have zero output current at zero glucose concentration, even in the presence of the other electroactive species of serum or blood. The electrode is preferably three or four-layered, with the layers serially deposited within a recess upon the tip of a polyamide insulated gold wire. A first glucose concentration-to-current transducing layer is overcoated with an electrically insulating and glucose flux limiting layer (second layer) on which, optionally, an immobilized interference-eliminating horse-radish peroxidase based film is deposited (third layer). An outer (fourth) layer is biocompatible.

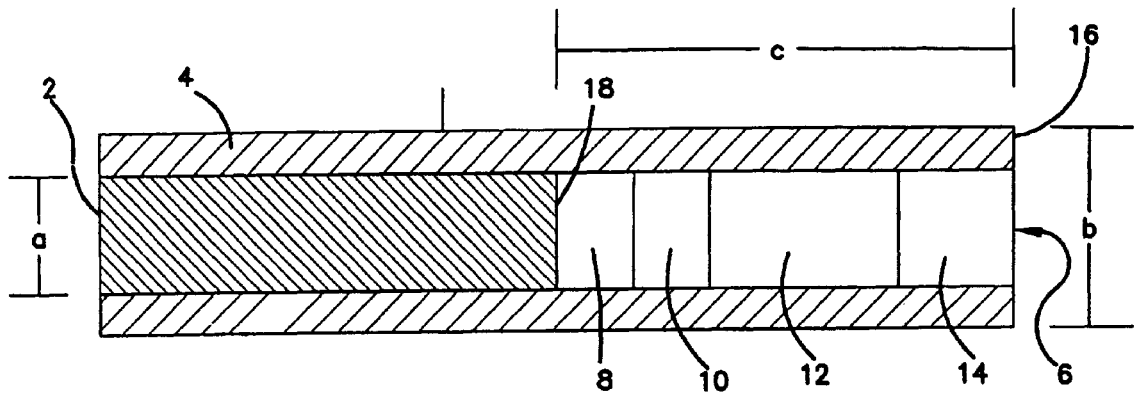

U.S. PATENT DOCUMENTS

| | | |
|---|---|---|
| 3,635,926 A | 1/1972 | Gresham et al. |
| 3,651,318 A | 3/1972 | Czekajewski |
| 3,653,841 A | 4/1972 | Klein |
| 3,698,386 A | 10/1972 | Fried |
| 3,719,564 A | 3/1973 | Lilly, Jr. et al. |
| 3,768,014 A | 10/1973 | Smith et al. |
| 3,775,182 A | 11/1973 | Patton et al. |
| 3,776,832 A | 12/1973 | Oswin et al. |
| 3,785,939 A | 1/1974 | Hsu |
| 3,837,339 A | 9/1974 | Aisenberg et al. |
| 3,851,018 A | 11/1974 | Kelly |
| 3,919,051 A | 11/1975 | Koch et al. |
| 3,926,760 A | 12/1975 | Allen et al. |
| 3,929,971 A | 12/1975 | Roy |
| 3,930,889 A | 1/1976 | Ruggiero et al. |
| 3,933,593 A | 1/1976 | Sternberg |
| 3,943,918 A | 3/1976 | Lewis |
| 3,964,974 A | 6/1976 | Banauch et al. |
| 3,966,580 A | 6/1976 | Janata et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,024,312 A | 5/1977 | Korpman |
| 4,032,729 A | 6/1977 | Koistinen |
| 4,036,749 A | 7/1977 | Anderson |
| 4,040,908 A | 8/1977 | Clark, Jr. |
| 4,055,175 A | 10/1977 | Clemens et al. |
| 4,059,406 A | 11/1977 | Fleet |
| 4,059,708 A | 11/1977 | Heiss, Jr. et al. |
| 4,073,713 A | 2/1978 | Newman |
| 4,076,596 A | 2/1978 | Connery et al. |
| 4,076,656 A | 2/1978 | White et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danniger et al. |
| 4,172,770 A | 10/1979 | Semersky et al. |
| 4,178,916 A | 12/1979 | McNamara |
| 4,193,982 A | 3/1980 | Avrameas et al. |
| 4,197,840 A | 4/1980 | Beck et al. |
| 4,206,755 A | 6/1980 | Klein |
| 4,215,703 A | 8/1980 | Wilson |
| 4,224,125 A | 9/1980 | Nakamura et al. |
| 4,240,438 A | 12/1980 | Updike et al. |
| 4,240,889 A | 12/1980 | Yoda et al. |
| 4,241,438 A | 12/1980 | Kern |
| 4,245,634 A | 1/1981 | Albisser et al. |
| 4,247,297 A | 1/1981 | Berti et al. |
| 4,255,500 A | 3/1981 | Hooke |
| 4,259,540 A | 3/1981 | Sabia |
| 4,271,449 A | 6/1981 | Grogan |
| 4,275,225 A | 6/1981 | Krespan |
| 4,318,784 A | 3/1982 | Higgins et al. |
| 4,324,257 A | 4/1982 | Albarda et al. |
| 4,327,725 A | 5/1982 | Cortese et al. |
| 4,331,869 A | 5/1982 | Rollo |
| 4,335,255 A | 6/1982 | Krespan |
| 4,340,458 A | 7/1982 | Lerner et al. |
| 4,344,438 A | 8/1982 | Schultz |
| 4,352,960 A | 10/1982 | Dormer et al. |
| 4,353,888 A | 10/1982 | Sefton |
| 4,356,074 A | 10/1982 | Johnson |
| 4,357,282 A | 11/1982 | Anderson et al. |
| 4,365,637 A | 12/1982 | Johnson |
| 4,366,033 A | 12/1982 | Richter et al. |
| 4,374,013 A | 2/1983 | Enfors |
| 4,375,399 A | 3/1983 | Havas et al. |
| 4,384,586 A | 5/1983 | Christiansen |
| 4,388,166 A | 6/1983 | Suzuki et al. |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,288 A | 10/1983 | Langer et al. |
| 4,407,959 A | 10/1983 | Tsuji et al. |
| 4,415,666 A | 11/1983 | D'Orazio et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,431,507 A | 2/1984 | Nankai et al. |
| 4,436,094 A | 3/1984 | Cerami |
| 4,440,175 A | 4/1984 | Wilkins |
| 4,443,218 A | 4/1984 | DeCant, Jr. et al. |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,467,811 A | 8/1984 | Clark, Jr. |
| 4,469,110 A | 9/1984 | Slama |
| 4,476,003 A | 10/1984 | Frank et al. |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,499,249 A | 2/1985 | Nakagawa et al. |
| 4,506,680 A | 3/1985 | Stokes |
| 4,512,348 A | 4/1985 | Uchigaki et al. |
| 4,522,690 A | 6/1985 | Venkatsetty |
| 4,524,114 A | 6/1985 | Samuels et al. |
| 4,526,661 A | 7/1985 | Steckhan et al. |
| 4,526,948 A | 7/1985 | Resnick |
| 4,527,240 A | 7/1985 | Kvitash |
| 4,530,696 A | 7/1985 | Bisera et al. |
| 4,534,356 A | 8/1985 | Papadakis |
| 4,538,616 A | 9/1985 | Rogoff et al. |
| 4,543,955 A | 10/1985 | Schroeppel |
| 4,544,869 A | 10/1985 | Pittaway |
| 4,545,382 A | 10/1985 | Higgins et al. |
| 4,552,840 A | 11/1985 | Riffer |
| 4,560,534 A | 12/1985 | Kung et al. |
| 4,561,443 A | 12/1985 | Hogrefe et al. |
| 4,569,589 A | 2/1986 | Neufeld |
| 4,571,292 A | 2/1986 | Liu et al. |
| 4,573,994 A | 3/1986 | Fischell et al. |
| 4,577,642 A | 3/1986 | Stokes |
| 4,581,336 A | 4/1986 | Malloy et al. |
| 4,595,011 A | 6/1986 | Phillips |
| 4,595,479 A | 6/1986 | Kimura et al. |
| 4,614,760 A | 9/1986 | Homan et al. |
| 4,619,754 A | 10/1986 | Niki et al. |
| 4,619,793 A * | 10/1986 | Lee ............................ 264/2.6 |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| RE32,361 E | 2/1987 | Duggan |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |

| | | | | | | |
|---|---|---|---|---|---|---|
| 4,658,463 A | 4/1987 | Sugita et al. | | 4,890,621 A | 1/1990 | Hakky |
| 4,663,824 A | 5/1987 | Kenmochi | | 4,894,137 A | 1/1990 | Takizawa et al. |
| 4,671,288 A | 6/1987 | Gough | | 4,896,142 A | 1/1990 | Aycox et al. |
| 4,674,652 A | 6/1987 | Aten et al. | | 4,897,162 A | 1/1990 | Lewandowski et al. |
| 4,679,562 A | 7/1987 | Luksha | | 4,897,173 A | 1/1990 | Nankai et al. |
| 4,680,268 A | 7/1987 | Clark, Jr. | | 4,897,457 A | 1/1990 | Nakamura et al. |
| 4,681,111 A | 7/1987 | Silvian | | 4,899,839 A | 2/1990 | Dessertine et al. |
| 4,682,602 A | 7/1987 | Prohaska | | 4,909,908 A | 3/1990 | Ross et al. |
| 4,684,537 A | 8/1987 | Graetzel et al. | | 4,911,794 A | 3/1990 | Parce et al. |
| 4,685,463 A | 8/1987 | Williams | | 4,917,800 A | 4/1990 | Lonsdale et al. |
| 4,686,624 A | 8/1987 | Blum et al. | | 4,919,141 A | 4/1990 | Zier et al. |
| 4,698,582 A | 10/1987 | Braun et al. | | 4,919,767 A | 4/1990 | Vadgama et al. |
| 4,703,756 A * | 11/1987 | Gough et al. ............... 600/347 | | 4,920,969 A | 5/1990 | Suzuki |
| 4,711,245 A | 12/1987 | Higgins et al. | | 4,920,977 A | 5/1990 | Haynes |
| 4,711,251 A | 12/1987 | Stokes | | 4,923,586 A | 5/1990 | Katayama et al. |
| 4,714,462 A | 12/1987 | DiDomenico | | 4,925,268 A | 5/1990 | Iyer et al. |
| 4,717,673 A | 1/1988 | Wrighton et al. | | 4,927,407 A | 5/1990 | Dorman |
| 4,718,893 A | 1/1988 | Dorman | | 4,927,516 A | 5/1990 | Yamaguchi et al. |
| 4,721,601 A | 1/1988 | Wrighton et al. | | 4,931,795 A | 6/1990 | Gord |
| 4,721,677 A | 1/1988 | Clark, Jr. | | 4,934,369 A | 6/1990 | Maxwell |
| 4,726,378 A | 2/1988 | Kaplan | | 4,935,105 A | 6/1990 | Churchouse |
| 4,726,716 A | 2/1988 | McGuire | | 4,935,345 A | 6/1990 | Guibeau et al. |
| 4,731,051 A | 3/1988 | Fischell | | 4,936,956 A | 6/1990 | Wrighton |
| 4,731,726 A | 3/1988 | Allen, III | | 4,938,860 A | 7/1990 | Wogoman |
| 4,747,828 A | 5/1988 | Tseo | | 4,942,127 A | 7/1990 | Wada et al. |
| 4,749,985 A | 6/1988 | Corsberg | | 4,944,299 A | 7/1990 | Silvian |
| 4,750,496 A | 6/1988 | Reinhardt | | 4,945,045 A | 7/1990 | Forrest et al. |
| 4,753,652 A | 6/1988 | Langer et al. | | 4,950,378 A | 8/1990 | Nagata |
| 4,757,022 A | 7/1988 | Shults et al. | | 4,953,552 A | 9/1990 | DeMarzo |
| 4,758,323 A | 7/1988 | Davis et al. | | 4,954,129 A | 9/1990 | Giuliani et al. |
| 4,759,371 A | 7/1988 | Franetzki | | 4,955,861 A | 9/1990 | Enegren et al. |
| 4,759,828 A | 7/1988 | Young et al. | | 4,957,115 A | 9/1990 | Selker |
| 4,764,416 A | 8/1988 | Ueyama et al. | | 4,958,632 A | 9/1990 | Duggan |
| 4,776,944 A | 10/1988 | Janata et al. | | 4,963,595 A | 10/1990 | Ward et al. |
| 4,779,618 A | 10/1988 | Mund et al. | | 4,968,400 A | 11/1990 | Shimomura et al. |
| 4,781,798 A | 11/1988 | Gough | | 4,969,468 A | 11/1990 | Byers et al. |
| 4,784,736 A | 11/1988 | Lonsdale et al. | | 4,970,145 A | 11/1990 | Bennetto et al. |
| 4,787,398 A | 11/1988 | Garcia et al. | | 4,974,929 A | 12/1990 | Curry |
| 4,795,707 A | 1/1989 | Niiyama et al. | | 4,979,509 A | 12/1990 | Hakky |
| 4,796,634 A | 1/1989 | Huntsman et al. | | 4,984,929 A | 1/1991 | Rock et al. |
| 4,803,243 A | 2/1989 | Fujimoto et al. | | 4,986,271 A * | 1/1991 | Wilkins ...................... 600/347 |
| 4,803,625 A | 2/1989 | Fu et al. | | 4,986,671 A | 1/1991 | Sun et al. |
| 4,803,726 A | 2/1989 | Levine et al. | | 4,990,845 A | 2/1991 | Gord |
| 4,805,624 A | 2/1989 | Yao et al. | | 4,991,582 A | 2/1991 | Byers et al. |
| 4,810,470 A | 3/1989 | Burkhardt et al. | | 4,994,068 A | 2/1991 | Hufnagle |
| 4,813,424 A | 3/1989 | Wilkins | | 4,994,167 A | 2/1991 | Shults et al. |
| 4,815,469 A | 3/1989 | Cohen et al. | | 4,995,402 A | 2/1991 | Smith et al. |
| 4,820,399 A | 4/1989 | Senda et al. | | 5,001,054 A | 3/1991 | Wagner |
| 4,822,337 A | 4/1989 | Newhouse et al. | | 5,002,572 A | 3/1991 | Picha |
| 4,830,959 A | 5/1989 | McNeil et al. | | 5,007,427 A | 4/1991 | Suzuki et al. |
| 4,832,797 A | 5/1989 | Vadgama et al. | | 5,007,929 A | 4/1991 | Quaid |
| 4,835,372 A | 5/1989 | Gombrich et al. | | 5,016,172 A | 5/1991 | Dessertine |
| RE32,947 E | 6/1989 | Dormer et al. | | 5,016,201 A | 5/1991 | Bryan et al. |
| 4,837,049 A | 6/1989 | Byers et al. | | 5,016,631 A | 5/1991 | Hogrefe et al. |
| 4,838,887 A | 6/1989 | Idriss | | 5,019,974 A | 5/1991 | Beckers |
| 4,840,893 A | 6/1989 | Hill et al. | | 5,030,333 A | 7/1991 | Clark, Jr. |
| RE32,974 E | 7/1989 | Porat et al. | | 5,034,112 A | 7/1991 | Murase et al. |
| 4,844,076 A | 7/1989 | Lesho et al. | | 5,034,192 A | 7/1991 | Wrighton et al. |
| 4,845,035 A | 7/1989 | Fanta et al. | | 5,035,860 A | 7/1991 | Kleingeld et al. |
| 4,848,351 A | 7/1989 | Finch | | 5,036,860 A | 8/1991 | Leigh et al. |
| 4,849,458 A | 7/1989 | Reed et al. | | 5,036,861 A | 8/1991 | Sembrowich et al. |
| 4,856,340 A | 8/1989 | Garrison | | 5,037,527 A | 8/1991 | Hayashi et al. |
| 4,857,713 A | 8/1989 | Brown | | 5,049,487 A | 9/1991 | Phillips et al. |
| 4,858,617 A | 8/1989 | Sanders | | 5,050,612 A | 9/1991 | Matsumura |
| 4,870,561 A | 9/1989 | Love et al. | | 5,055,171 A * | 10/1991 | Peck ...................... 204/290.05 |
| 4,871,351 A | 10/1989 | Feingold | | 5,058,592 A | 10/1991 | Whisler |
| 4,871,440 A | 10/1989 | Nagata et al. | | 5,059,654 A | 10/1991 | Hou et al. |
| 4,874,499 A | 10/1989 | Smith et al. | | 5,063,081 A | 11/1991 | Cozzette et al. |
| 4,874,500 A | 10/1989 | Madou et al. | | 5,067,491 A | 11/1991 | Taylor et al. |
| 4,889,744 A | 12/1989 | Quaid | | 5,068,536 A | 11/1991 | Rosenthal |
| 4,890,620 A | 1/1990 | Gough | | 5,070,535 A | 12/1991 | Hochmair et al. |

| | | | | | |
|---|---|---|---|---|---|
| 5,073,500 A | 12/1991 | Saito et al. | 5,251,126 A | 10/1993 | Kahn et al. |
| 5,074,977 A | 12/1991 | Cheung et al. | 5,257,971 A | 11/1993 | Lord et al. |
| 5,077,476 A | 12/1991 | Rosenthal | 5,257,980 A | 11/1993 | Van Antwerp et al. |
| 5,078,854 A | 1/1992 | Burgess et al. | 5,259,769 A | 11/1993 | Cruise et al. |
| 5,082,550 A | 1/1992 | Rishpon et al. | 5,261,401 A | 11/1993 | Baker et al. |
| 5,082,786 A | 1/1992 | Nakamoto | 5,262,035 A | 11/1993 | Gregg et al. |
| 5,084,828 A | 1/1992 | Kaufman et al. | 5,262,305 A | 11/1993 | Heller et al. |
| 5,088,981 A | 2/1992 | Howson et al. | 5,264,103 A | 11/1993 | Yoshioka et al. |
| 5,089,112 A | 2/1992 | Skotheim et al. | 5,264,104 A | 11/1993 | Gregg et al. |
| 5,094,951 A | 3/1992 | Rosenberg | 5,264,106 A | 11/1993 | McAleer et al. |
| 5,095,904 A | 3/1992 | Seligman et al. | 5,265,888 A | 11/1993 | Yamamoto et al. |
| 5,096,560 A | 3/1992 | Takai et al. | 5,266,179 A | 11/1993 | Nankai et al. |
| 5,096,836 A | 3/1992 | Macho et al. | 5,269,212 A | 12/1993 | Peters et al. |
| 5,097,834 A | 3/1992 | Skrabal | 5,271,736 A | 12/1993 | Picha |
| 5,101,814 A | 4/1992 | Palti | 5,271,815 A | 12/1993 | Wong |
| 5,108,564 A | 4/1992 | Szuminsky et al. | 5,272,060 A | 12/1993 | Hamamoto et al. |
| 5,109,850 A | 5/1992 | Blanco et al. | 5,275,159 A | 1/1994 | Griebel |
| 5,111,539 A | 5/1992 | Hiruta et al. | 5,276,610 A | 1/1994 | Maeda et al. |
| 5,111,818 A | 5/1992 | Suzuji et al. | 5,278,079 A | 1/1994 | Gubinski et al. |
| 5,114,678 A | 5/1992 | Crawford et al. | 5,279,294 A | 1/1994 | Anderson |
| 5,120,420 A | 6/1992 | Nankai et al. | 5,282,848 A | 2/1994 | Schmitt |
| 5,120,421 A | 6/1992 | Glass et al. | 5,282,950 A | 2/1994 | Dietze et al. |
| 5,126,034 A | 6/1992 | Carter et al. | 5,284,156 A | 2/1994 | Schramm et al. |
| 5,126,247 A | 6/1992 | Palmer et al. | 5,284,570 A | 2/1994 | Savage et al. |
| 5,130,009 A | 7/1992 | Marsoner et al. | 5,284,748 A | 2/1994 | Mroczkowski et al. |
| 5,131,441 A | 7/1992 | Simpson et al. | 5,285,513 A | 2/1994 | Kaufman et al. |
| 5,133,856 A | 7/1992 | Yamaguchi et al. | 5,285,792 A | 2/1994 | Sjoquist et al. |
| 5,134,391 A | 7/1992 | Okada | 5,286,362 A | 2/1994 | Hoenes et al. |
| 5,135,003 A | 8/1992 | Souma | 5,286,364 A | 2/1994 | Yacynych et al. |
| 5,139,023 A | 8/1992 | Stanley et al. | 5,288,636 A | 2/1994 | Pollmann et al. |
| 5,140,393 A | 8/1992 | Hijikihigawa et al. | 5,291,887 A | 3/1994 | Stanley et al. |
| 5,140,985 A | 8/1992 | Schroeder et al. | 5,293,546 A | 3/1994 | Tadros et al. |
| 5,141,868 A | 8/1992 | Shanks et al. | 5,299,571 A | 4/1994 | Mastrototaro |
| 5,147,725 A | 9/1992 | Pinchuk | 5,304,127 A | 4/1994 | Kawahara et al. |
| 5,153,827 A | 10/1992 | Coutre et al. | 5,304,468 A | 4/1994 | Phillips et al. |
| 5,161,532 A | 11/1992 | Joseph | 5,307,263 A | 4/1994 | Brown |
| 5,165,407 A * | 11/1992 | Wilson et al. ............... 600/345 | 5,309,919 A | 5/1994 | Snell et al. |
| 5,168,046 A | 12/1992 | Hamamoto et al. | 5,310,469 A | 5/1994 | Cunningham et al. |
| 5,171,689 A | 12/1992 | Kawaguri et al. | 5,310,885 A | 5/1994 | Maier et al. |
| 5,174,291 A | 12/1992 | Schoonen et al. | 5,312,361 A | 5/1994 | Zadini et al. |
| 5,176,644 A | 1/1993 | Srisathapat et al. | 5,314,450 A | 5/1994 | Thompson |
| 5,176,662 A | 1/1993 | Bartholomew et al. | 5,314,471 A | 5/1994 | Brauker et al. |
| 5,182,707 A | 1/1993 | Cooper et al. | 5,318,521 A | 6/1994 | Slettenmark |
| 5,184,359 A | 2/1993 | Tsukamura et al. | 5,320,098 A | 6/1994 | Davidson |
| 5,185,256 A | 2/1993 | Nankai et al. | 5,320,725 A | 6/1994 | Gregg et al. |
| 5,190,041 A | 3/1993 | Palti | 5,322,063 A | 6/1994 | Allen et al. |
| 5,192,415 A | 3/1993 | Yoshioka et al. | 5,324,303 A | 6/1994 | Strong et al. |
| 5,192,416 A | 3/1993 | Wang et al. | 5,324,316 A | 6/1994 | Schulman et al. |
| 5,193,539 A | 3/1993 | Schulman et al. | 5,326,356 A | 7/1994 | Della Valle et al. |
| 5,193,540 A | 3/1993 | Schulman et al. | 5,326,449 A | 7/1994 | Cunningham |
| 5,197,322 A | 3/1993 | Indravudh | 5,328,460 A | 7/1994 | Lord et al. |
| 5,198,367 A | 3/1993 | Aizawa et al. | 5,330,521 A | 7/1994 | Cohen |
| 5,198,771 A | 3/1993 | Fidler et al. | 5,330,634 A | 7/1994 | Wong et al. |
| 5,200,051 A | 4/1993 | Cozzette et al. | 5,331,966 A | 7/1994 | Bennett et al. |
| 5,202,261 A | 4/1993 | Musho et al. | 5,337,258 A | 8/1994 | Dennis |
| 5,205,920 A | 4/1993 | Oyama et al. | 5,337,747 A | 8/1994 | Neftei |
| 5,206,145 A | 4/1993 | Cattell | 5,340,722 A | 8/1994 | Wolfbeis et al. |
| 5,208,154 A | 5/1993 | Weaver et al. | 5,342,409 A | 8/1994 | Mullet |
| 5,209,229 A | 5/1993 | Gilli | 5,342,789 A | 8/1994 | Chick et al. |
| 5,215,887 A | 6/1993 | Saito | 5,343,869 A | 9/1994 | Pross et al. |
| 5,216,597 A | 6/1993 | Beckers | 5,344,454 A | 9/1994 | Clarke et al. |
| 5,217,442 A | 6/1993 | Davis | 5,348,788 A | 9/1994 | White |
| 5,217,595 A | 6/1993 | Smith et al. | 5,350,407 A | 9/1994 | McClure et al. |
| 5,227,042 A | 7/1993 | Zawodzinski et al. | 5,352,348 A | 10/1994 | Young et al. |
| 5,229,282 A | 7/1993 | Yoshioka et al. | 5,352,351 A | 10/1994 | White |
| 5,232,668 A | 8/1993 | Grant et al. | 5,354,319 A | 10/1994 | Wyborny et al. |
| 5,235,003 A | 8/1993 | Ward et al. | 5,356,348 A | 10/1994 | Bellio et al. |
| 5,243,983 A | 9/1993 | Tarr et al. | 5,356,786 A | 10/1994 | Heller et al. |
| 5,246,867 A | 9/1993 | Lakowicz et al. | 5,358,514 A | 10/1994 | Schulman et al. |
| 5,249,576 A | 10/1993 | Goldberger et al. | 5,364,797 A | 11/1994 | Olson et al. |
| 5,250,439 A | 10/1993 | Musho et al. | 5,366,609 A | 11/1994 | White et al. |

| | | | | | | |
|---|---|---|---|---|---|---|
| 5,368,028 A | 11/1994 | Palti | 5,514,253 A | 5/1996 | Davis et al. | |
| 5,368,562 A | 11/1994 | Blomquist et al. | 5,518,006 A | 5/1996 | Mawhirt et al. | |
| 5,370,622 A | 12/1994 | Livingston et al. | 5,520,787 A | 5/1996 | Hanagan et al. | |
| 5,371,687 A | 12/1994 | Holmes, II et al. | 5,522,865 A | 6/1996 | Schulman et al. | |
| 5,372,133 A | 12/1994 | Hogen Esch | 5,525,511 A | 6/1996 | D'Costa | |
| 5,372,719 A | 12/1994 | Afejan et al. | 5,526,120 A | 6/1996 | Jina et al. | |
| 5,375,604 A | 12/1994 | Kelly et al. | 5,527,307 A | 6/1996 | Srisathapat et al. | |
| 5,376,070 A | 12/1994 | Purvis et al. | 5,529,676 A | 6/1996 | Maley et al. | |
| 5,376,251 A | 12/1994 | Kaneko et al. | 5,531,878 A | 7/1996 | Vadgama et al. | |
| 5,377,258 A | 12/1994 | Bro | 5,538,007 A | 7/1996 | Gorman | |
| 5,378,628 A | 1/1995 | Gratzel et al. | 5,538,511 A | 7/1996 | Van Antwerp et al. | |
| 5,379,238 A | 1/1995 | Stark | 5,540,828 A | 7/1996 | Yacynych | |
| 5,380,422 A | 1/1995 | Negishi et al. | 5,545,152 A | 8/1996 | Funderburk et al. | |
| 5,380,536 A | 1/1995 | Hubbell et al. | 5,545,191 A | 8/1996 | Mann et al. | |
| 5,382,346 A | 1/1995 | Uenoyama et al. | 5,545,220 A | 8/1996 | Andrews et al. | |
| 5,384,028 A | 1/1995 | Ito | 5,545,223 A | 8/1996 | Neuenfeldt et al. | |
| 5,387,327 A | 2/1995 | Khan | 5,549,113 A | 8/1996 | Halleck et al. | |
| 5,390,671 A | 2/1995 | Lord et al. | 5,549,115 A | 8/1996 | Morgan et al. | |
| 5,391,250 A | 2/1995 | Cheney, II et al. | 5,549,675 A | 8/1996 | Neuenfeldt et al. | |
| 5,393,903 A | 2/1995 | Gratzel et al. | 5,552,027 A | 9/1996 | Birkle et al. | |
| 5,395,504 A | 3/1995 | Saurer et al. | 5,554,166 A | 9/1996 | Lange et al. | |
| 5,397,848 A | 3/1995 | Yang et al. | 5,556,524 A | 9/1996 | Albers | |
| 5,399,823 A | 3/1995 | McCusker | 5,560,357 A | 10/1996 | Faupei et al. | |
| 5,400,782 A | 3/1995 | Beaubiah | 5,562,713 A | 10/1996 | Silvian | |
| 5,408,999 A | 4/1995 | Singh et al. | 5,564,439 A | 10/1996 | Picha | |
| 5,410,471 A | 4/1995 | Alyfuku et al. | 5,565,085 A | 10/1996 | Ikeda et al. | |
| 5,410,474 A | 4/1995 | Fox | 5,567,302 A | 10/1996 | Song et al. | |
| 5,411,536 A | 5/1995 | Armstrong | 5,568,806 A | 10/1996 | Cheney, II et al. | |
| 5,411,647 A | 5/1995 | Johnson et al. | 5,569,186 A | 10/1996 | Lord et al. | |
| 5,413,690 A | 5/1995 | Kost et al. | 5,569,212 A | 10/1996 | Brown | |
| 5,422,246 A | 6/1995 | Koopal et al. | 5,569,462 A | 10/1996 | Martinson et al. | |
| 5,426,032 A | 6/1995 | Phillips | 5,571,395 A | 11/1996 | Park et al. | |
| 5,429,129 A | 7/1995 | Lovejoy et al. | 5,573,506 A | 11/1996 | Vasko | |
| 5,431,160 A | 7/1995 | Wilkins | 5,573,647 A | 11/1996 | Maley et al. | |
| 5,431,691 A | 7/1995 | Snell et al. | 5,575,895 A | 11/1996 | Ikeda et al. | |
| 5,433,710 A | 7/1995 | Van Antwerp et al. | 5,575,930 A | 11/1996 | Tietje-Girault et al. | |
| 5,437,973 A | 8/1995 | Vadgama et al. | 5,580,527 A | 12/1996 | Bell et al. | |
| 5,437,999 A | 8/1995 | Dieboid et al. | 5,580,794 A | 12/1996 | Allen | |
| 5,438,984 A | 8/1995 | Schoendorfer | 5,582,184 A | 12/1996 | Erickson et al. | |
| 5,445,611 A | 8/1995 | Eppstein et al. | 5,582,593 A | 12/1996 | Hultman | |
| 5,445,920 A | 8/1995 | Saito | 5,582,697 A | 12/1996 | Ikeda et al. | |
| 5,451,260 A | 9/1995 | Versteeg et al. | 5,582,698 A | 12/1996 | Flaherty et al. | |
| 5,452,173 A | 9/1995 | Brannon et al. | 5,584,813 A | 12/1996 | Livingston et al. | |
| 5,453,199 A | 9/1995 | Afejan et al. | 5,584,876 A | 12/1996 | Bruchman et al. | |
| 5,453,278 A | 9/1995 | Chan et al. | 5,586,553 A | 12/1996 | Halili et al. | |
| 5,456,692 A | 10/1995 | Smith, Jr. et al. | 5,587,273 A | 12/1996 | Yan et al. | |
| 5,456,940 A | 10/1995 | Funderburk | 5,589,326 A | 12/1996 | Deng et al. | |
| 5,458,140 A | 10/1995 | Eppstein et al. | 5,589,563 A | 12/1996 | Ward et al. | |
| 5,460,618 A | 10/1995 | Harreld | 5,590,651 A | 1/1997 | Shaffer et al. | |
| 5,462,064 A | 10/1995 | D'Angelo et al. | 5,593,440 A | 1/1997 | Brauker et al. | |
| 5,462,525 A | 10/1995 | Srisathapat et al. | 5,593,852 A * | 1/1997 | Heller et al. | 435/14 |
| 5,466,218 A | 11/1995 | Srisathapat et al. | 5,594,906 A | 1/1997 | Holmes, II et al. | |
| 5,469,846 A | 11/1995 | Khan | 5,596,150 A | 1/1997 | Arndy et al. | |
| 5,472,317 A | 12/1995 | Field et al. | 5,596,994 A | 1/1997 | Bro | |
| 5,476,460 A | 12/1995 | Montalvo | 5,601,435 A | 2/1997 | Quy | |
| 5,477,855 A | 12/1995 | Schindler et al. | 5,601,694 A | 2/1997 | Maley et al. | |
| 5,482,473 A | 1/1996 | Lord et al. | 5,605,152 A | 2/1997 | Slate et al. | |
| 5,484,404 A | 1/1996 | Schulman et al. | 5,607,565 A | 3/1997 | Azarnia et al. | |
| 5,487,751 A | 1/1996 | Radons et al. | 5,611,900 A | 3/1997 | Worden et al. | |
| 5,491,474 A | 2/1996 | Suni et al. | 5,615,671 A | 4/1997 | Schoonen et al. | |
| 5,494,562 A | 2/1996 | Maley et al. | 5,616,222 A | 4/1997 | Maley et al. | |
| 5,496,453 A | 3/1996 | Uenoyama et al. | 5,617,851 A | 4/1997 | Lipkovker | |
| 5,497,772 A | 3/1996 | Schulman et al. | 5,623,925 A | 4/1997 | Swenson et al. | |
| 5,501,665 A | 3/1996 | Jhuboo et al. | 5,624,537 A | 4/1997 | Turner et al. | |
| 5,501,956 A | 3/1996 | Wada et al. | 5,628,309 A | 5/1997 | Brown | |
| 5,505,709 A | 4/1996 | Funderburk | 5,628,310 A | 5/1997 | Rao et al. | |
| 5,505,713 A | 4/1996 | Van Antwerp et al. | 5,628,890 A | 5/1997 | Carter et al. | |
| 5,507,288 A | 4/1996 | Bocker et al. | 5,629,981 A | 5/1997 | Nerlikar | |
| 5,508,171 A | 4/1996 | Walling et al. | 5,637,095 A | 6/1997 | Nason et al. | |
| 5,509,410 A | 4/1996 | Hill et al. | 5,640,764 A | 6/1997 | Strojnik | |
| 5,514,103 A | 5/1996 | Srisathapat et al. | 5,640,954 A | 6/1997 | Pfeiffer et al. | |

| | | | | | | |
|---|---|---|---|---|---|---|
| 5,643,212 | A | 7/1997 | Coutre et al. | 5,791,344 A | 8/1998 | Schulman et al. |
| 5,647,853 | A | 7/1997 | Feldmann et al. | 5,792,117 A | 8/1998 | Brown |
| 5,650,062 | A | 7/1997 | Ikeda et al. | 5,795,774 A | 8/1998 | Matsumoto et al. |
| 5,651,767 | A | 7/1997 | Schulman et al. | 5,798,065 A | 8/1998 | Picha |
| 5,651,869 | A | 7/1997 | Yoshioka et al. | 5,800,387 A | 9/1998 | Duffy et al. |
| 5,653,735 | A | 8/1997 | Chen et al. | 5,800,420 A | 9/1998 | Gross et al. |
| 5,653,756 | A | 8/1997 | Clarke et al. | 5,800,529 A | 9/1998 | Brauker et al. |
| 5,653,863 | A | 8/1997 | Glenshaw et al. | 5,804,048 A | 9/1998 | Wong et al. |
| 5,658,250 | A | 8/1997 | Blomquist et al. | 5,807,315 A | 9/1998 | Van Antwerp et al. |
| 5,658,330 | A | 8/1997 | Carlisle et al. | 5,807,375 A | 9/1998 | Gross et al. |
| 5,660,163 | A | 8/1997 | Schulman et al. | 5,807,406 A | 9/1998 | Brauker et al. |
| 5,662,694 | A | 9/1997 | Lidman et al. | 5,811,487 A | 9/1998 | Schulz, Jr. et al. |
| 5,665,065 | A | 9/1997 | Colman et al. | 5,814,599 A | 9/1998 | Mitragotri et al. |
| 5,667,983 | A | 9/1997 | Abel et al. | 5,820,551 A | 10/1998 | Hill et al. |
| 5,670,031 | A | 9/1997 | Hintsche et al. | 5,820,570 A | 10/1998 | Erickson et al. |
| 5,678,571 | A | 10/1997 | Brown | 5,820,622 A | 10/1998 | Gross et al. |
| 5,679,690 | A | 10/1997 | Andre et al. | 5,822,715 A | 10/1998 | Worthington et al. |
| 5,680,858 | A | 10/1997 | Hansen et al. | 5,825,488 A | 10/1998 | Kohl et al. |
| 5,682,233 | A | 10/1997 | Brinda | 5,827,179 A | 10/1998 | Lichter et al. |
| 5,686,717 | A | 11/1997 | Knowles et al. | 5,827,183 A | 10/1998 | Kurnik et al. |
| 5,686,829 | A | 11/1997 | Girault | 5,827,184 A | 10/1998 | Netherly et al. |
| 5,695,473 | A | 12/1997 | Olsen | 5,828,943 A | 10/1998 | Brown |
| 5,695,623 | A | 12/1997 | Michel et al. | 5,830,341 A | 11/1998 | Gilmartin |
| 5,695,949 | A | 12/1997 | Galen et al. | 5,832,448 A | 11/1998 | Brown |
| 5,701,894 | A | 12/1997 | Cherry et al. | 5,833,603 A | 11/1998 | Kovacs et al. |
| 5,704,354 | A | 1/1998 | Priedel et al. | 5,834,224 A | 11/1998 | Ruger et al. |
| 5,704,922 | A | 1/1998 | Brown | 5,836,887 A | 11/1998 | Oka et al. |
| 5,706,807 | A | 1/1998 | Picha | 5,836,989 A | 11/1998 | Shelton |
| 5,707,502 | A | 1/1998 | McCaffrey et al. | 5,837,454 A | 11/1998 | Cozzette et al. |
| 5,708,247 | A | 1/1998 | McAleer et al. | 5,837,546 A | 11/1998 | Allen et al. |
| 5,710,630 | A | 1/1998 | Essenpreis et al. | 5,837,728 A | 11/1998 | Purcell |
| 5,711,001 | A | 1/1998 | Bussan et al. | 5,840,020 A | 11/1998 | Heinonen et al. |
| 5,711,297 | A | 1/1998 | Iliff et al. | 5,840,240 A | 11/1998 | Stenoien et al. |
| 5,711,861 | A | 1/1998 | Ward et al. | 5,842,983 A | 12/1998 | Abel et al. |
| 5,711,862 | A | 1/1998 | Sakoda et al. | 5,843,140 A | 12/1998 | Strojnik |
| 5,711,868 | A | 1/1998 | Maley et al. | 5,846,702 A | 12/1998 | Deng et al. |
| 5,713,888 | A | 2/1998 | Neuenfeldt et al. | 5,846,744 A | 12/1998 | Athey et al. |
| 5,714,123 | A | 2/1998 | Sohrab | 5,851,197 A | 12/1998 | Marano et al. |
| 5,718,234 | A | 2/1998 | Warden et al. | 5,854,078 A | 12/1998 | Asher et al. |
| 5,720,733 | A | 2/1998 | Brown | 5,854,189 A | 12/1998 | Kruse et al. |
| 5,720,862 | A | 2/1998 | Hamamoto et al. | 5,857,967 A | 1/1999 | Frid et al. |
| 5,721,783 | A | 2/1998 | Anderson | 5,857,983 A | 1/1999 | Douglas et al. |
| 5,722,397 | A | 3/1998 | Eppstein | 5,860,917 A | 1/1999 | Comanor et al. |
| 5,727,548 | A | 3/1998 | Hill et al. | 5,861,009 A | 1/1999 | Armstrong et al. |
| 5,730,124 | A | 3/1998 | Yamauchi | 5,861,019 A | 1/1999 | Sun et al. |
| 5,730,654 | A | 3/1998 | Brown | 5,862,803 A | 1/1999 | Besson et al. |
| 5,733,336 | A | 3/1998 | Neuenfeldt et al. | 5,871,465 A | 2/1999 | Vasko |
| 5,735,273 | A | 4/1998 | Kurnik et al. | 5,871,514 A | 2/1999 | Wiklund et al. |
| 5,735,285 | A | 4/1998 | Albert et al. | 5,872,713 A | 2/1999 | Douglas et al. |
| 5,741,211 | A | 4/1998 | Renirie et al. | 5,872,820 A | 2/1999 | Upadrasta |
| 5,741,330 | A | 4/1998 | Brauker et al. | 5,876,484 A | 3/1999 | Raskin et al. |
| 5,741,688 | A | 4/1998 | Oxenboll et al. | 5,879,163 A | 3/1999 | Brown et al. |
| 5,743,262 | A | 4/1998 | Lepper, Jr. et al. | 5,879,311 A | 3/1999 | Duchon et al. |
| 5,746,217 | A | 5/1998 | Erickson et al. | 5,879,373 A | 3/1999 | Roper et al. |
| 5,748,103 | A | 5/1998 | Flach et al. | 5,880,829 A | 3/1999 | Kauhaniemi et al. |
| 5,749,907 | A | 5/1998 | Mann | 5,882,494 A | 3/1999 | Van Antwerp |
| 5,750,926 | A | 5/1998 | Schulman et al. | 5,885,211 A | 3/1999 | Eppstein et al. |
| 5,756,632 | A | 5/1998 | Ward et al. | 5,885,245 A | 3/1999 | Lynch et al. |
| 5,770,028 | A | 6/1998 | Maley et al. | 5,887,133 A | 3/1999 | Brown et al. |
| 5,771,001 | A | 6/1998 | Cobb | 5,895,371 A | 4/1999 | Levitas et al. |
| 5,771,890 | A | 6/1998 | Tamada | 5,897,493 A | 4/1999 | Brown |
| 5,772,586 | A | 6/1998 | Heinonen et al. | 5,897,578 A | 4/1999 | Wiklund et al. |
| 5,777,060 | A | 7/1998 | Van Antwerp | 5,898,025 A | 4/1999 | Burg et al. |
| 5,779,665 | A | 7/1998 | Mastrototaro et al. | 5,899,855 A | 5/1999 | Brown |
| 5,782,814 | A | 7/1998 | Brown et al. | 5,899,931 A | 5/1999 | Deschamp et al. |
| 5,782,912 | A | 7/1998 | Brauker et al. | 5,904,708 A | 5/1999 | Goedeke |
| 5,785,681 | A | 7/1998 | Indravudh | 5,913,310 A | 6/1999 | Brown |
| 5,786,439 | A | 7/1998 | Van Antwerp et al. | 5,913,827 A | 6/1999 | Gorman |
| 5,786,584 | A | 7/1998 | Button et al. | 5,913,998 A | 6/1999 | Butler et al. |
| 5,787,900 | A | 8/1998 | Butler et al. | 5,914,026 A | 6/1999 | Blubaugh, Jr. et al. |
| 5,788,678 | A | 8/1998 | Van Antwerp | 5,916,445 A | 6/1999 | Hjerten et al. |

| Patent No. | Date | Inventor |
|---|---|---|
| 5,917,346 A | 6/1999 | Gord |
| 5,918,603 A | 7/1999 | Brown |
| 5,919,215 A | 7/1999 | Wiklund et al. |
| 5,925,021 A | 7/1999 | Castellano et al. |
| 5,928,130 A | 7/1999 | Schmidt |
| 5,931,791 A | 8/1999 | Saltzstein et al. |
| 5,931,814 A | 8/1999 | Alex et al. |
| 5,933,136 A | 8/1999 | Brown |
| 5,935,099 A | 8/1999 | Peterson et al. |
| 5,935,785 A | 8/1999 | Reber et al. |
| 5,940,801 A | 8/1999 | Brown |
| 5,942,979 A | 8/1999 | Luppino |
| 5,945,345 A | 8/1999 | Blatt et al. |
| 5,947,749 A | 9/1999 | Rathburn |
| 5,947,921 A | 9/1999 | Johnson et al. |
| 5,948,512 A | 9/1999 | Kubota et al. |
| 5,950,632 A | 9/1999 | Reber et al. |
| 5,951,300 A | 9/1999 | Brown |
| 5,951,492 A | 9/1999 | Douglas et al. |
| 5,951,521 A | 9/1999 | Mastrototaro et al. |
| 5,951,836 A | 9/1999 | McAleer et al. |
| 5,954,643 A | 9/1999 | Van Antwerp |
| 5,954,685 A | 9/1999 | Tierny |
| 5,954,700 A | 9/1999 | Kovelman |
| 5,956,501 A | 9/1999 | Brown |
| 5,957,854 A | 9/1999 | Besson et al. |
| 5,957,890 A | 9/1999 | Mann et al. |
| 5,957,903 A | 9/1999 | Mirzaee et al. |
| 5,957,958 A | 9/1999 | Schulman et al. |
| 5,959,050 A | 9/1999 | Mosbach et al. |
| 5,960,403 A | 9/1999 | Brown |
| 5,961,451 A | 10/1999 | Reber et al. |
| 5,964,804 A | 10/1999 | Brauker et al. |
| 5,964,993 A | 10/1999 | Blubaugh, Jr. et al. |
| 5,965,380 A | 10/1999 | Heller et al. |
| 5,968,839 A | 10/1999 | Blatt et al. |
| 5,971,922 A | 10/1999 | Arita et al. |
| 5,971,941 A | 10/1999 | Simons et al. |
| 5,974,124 A | 10/1999 | Schlueter, Jr. et al. |
| 5,976,085 A | 11/1999 | Kimball et al. |
| 5,977,476 A | 11/1999 | Guha et al. |
| 5,981,294 A | 11/1999 | Blatt et al. |
| 5,985,129 A | 11/1999 | Gough et al. |
| 5,987,352 A | 11/1999 | Klein et al. |
| 5,989,409 A | 11/1999 | Kurnik et al. |
| 5,994,476 A | 11/1999 | Shin et al. |
| 5,995,860 A | 11/1999 | Sun et al. |
| 5,997,476 A | 12/1999 | Brown |
| 5,999,848 A | 12/1999 | Gord et al. |
| 5,999,849 A | 12/1999 | Gord et al. |
| 6,001,067 A | 12/1999 | Shults et al. |
| 6,001,471 A | 12/1999 | Bries et al. |
| 6,002,954 A | 12/1999 | Van Antwerp et al. |
| 6,002,961 A | 12/1999 | Mitragotri et al. |
| 6,004,441 A | 12/1999 | Fujiwara et al. |
| 6,007,845 A | 12/1999 | Domb |
| 6,011,984 A | 1/2000 | Van Antwerp et al. |
| 6,013,113 A | 1/2000 | Mika |
| 6,014,577 A | 1/2000 | Henning et al. |
| 6,016,448 A | 1/2000 | Busacker et al. |
| 6,017,435 A | 1/2000 | Hassard et al. |
| 6,018,678 A | 1/2000 | Mitragotri et al. |
| 6,023,629 A | 2/2000 | Tamada |
| 6,024,699 A | 2/2000 | Surwit et al. |
| 6,026,320 A | 2/2000 | Carlson et al. |
| 6,027,459 A | 2/2000 | Shain et al. |
| 6,027,692 A | 2/2000 | Galen et al. |
| 6,032,059 A | 2/2000 | Henning et al. |
| 6,032,199 A | 2/2000 | Lim et al. |
| 6,033,866 A | 3/2000 | Guo et al. |
| 6,035,237 A | 3/2000 | Schulman et al. |
| 6,040,194 A | 3/2000 | Chick et al. |
| 6,041,253 A | 3/2000 | Kost et al. |
| 6,043,437 A | 3/2000 | Schulman et al. |
| 6,048,691 A | 4/2000 | Maracas |
| 6,049,727 A | 4/2000 | Crothall |
| 6,051,372 A | 4/2000 | Bayerl et al. |
| 6,056,718 A | 5/2000 | Funderburk et al. |
| 6,057,377 A | 5/2000 | Sasaki et al. |
| 6,059,946 A | 5/2000 | Yukawa et al. |
| 6,063,459 A | 5/2000 | Velte |
| 6,063,637 A | 5/2000 | Arnold et al. |
| 6,066,083 A | 5/2000 | Slater et al. |
| 6,066,243 A | 5/2000 | Anderson et al. |
| 6,066,448 A | 5/2000 | Wohlstadter et al. |
| 6,067,474 A | 5/2000 | Schulman et al. |
| 6,068,615 A | 5/2000 | Brown et al. |
| 6,071,249 A | 6/2000 | Cunningham et al. |
| 6,071,251 A | 6/2000 | Cunningham et al. |
| 6,071,294 A | 6/2000 | Simons et al. |
| 6,071,391 A | 6/2000 | Gotoh et al. |
| 6,071,406 A | 6/2000 | Tsou |
| 6,073,049 A | 6/2000 | Alt et al. |
| 6,081,735 A | 6/2000 | Diab et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,156 A | 7/2000 | Cunningham et al. |
| 6,093,167 A | 7/2000 | Houben et al. |
| 6,093,172 A | 7/2000 | Funderburk et al. |
| 6,097,831 A | 8/2000 | Wieck et al. |
| 6,099,484 A | 8/2000 | Douglas et al. |
| 6,101,478 A | 8/2000 | Brown |
| 6,103,033 A | 8/2000 | Say et al. |
| 6,103,533 A | 8/2000 | Hassard et al. |
| 6,106,780 A | 8/2000 | Douglas et al. |
| 6,107,083 A | 8/2000 | Collins et al. |
| 6,110,148 A | 8/2000 | Brown et al. |
| 6,110,152 A | 8/2000 | Kovelman |
| 6,113,578 A | 9/2000 | Brown |
| 6,115,634 A | 9/2000 | Donders et al. |
| 6,117,290 A | 9/2000 | Say et al. |
| 6,119,028 A | 9/2000 | Schulman et al. |
| 6,120,676 A | 9/2000 | Heller et al. |
| 6,121,009 A * | 9/2000 | Heller et al. .................. 435/14 |
| 6,122,351 A | 9/2000 | Schlueter, Jr. et al. |
| 6,122,536 A | 9/2000 | Sun et al. |
| 6,125,978 A | 10/2000 | Ando et al. |
| 6,134,461 A | 10/2000 | Say et al. |
| 6,134,504 A | 10/2000 | Douglas et al. |
| 6,135,978 A | 10/2000 | Houben et al. |
| 6,139,718 A | 10/2000 | Kurnik et al. |
| 6,141,573 A | 10/2000 | Kurnik et al. |
| 6,142,939 A | 11/2000 | Eppstein et al. |
| 6,142,972 A | 11/2000 | Cheikh |
| 6,143,164 A | 11/2000 | Heller et al. |
| 6,144,837 A | 11/2000 | Quy |
| 6,144,869 A | 11/2000 | Berner et al. |
| 6,144,922 A | 11/2000 | Douglas et al. |
| 6,148,094 A | 11/2000 | Kinsella |
| 6,150,128 A | 11/2000 | Uretsky |
| 6,151,586 A | 11/2000 | Brown |
| 6,153,062 A | 11/2000 | Saito et al. |
| 6,153,069 A | 11/2000 | Pottgen et al. |
| 6,154,675 A | 11/2000 | Juran et al. |
| 6,159,147 A | 12/2000 | Lichter et al. |
| 6,161,095 A | 12/2000 | Brown |
| 6,162,611 A | 12/2000 | Heller et al. |
| 6,162,639 A | 12/2000 | Douglas |
| 6,167,362 A | 12/2000 | Brown et al. |

| Patent | Date | Inventor |
|---|---|---|
| 6,167,614 B1 | 1/2001 | Tuttle et al. |
| 6,168,563 B1 | 1/2001 | Brown |
| 6,170,318 B1 | 1/2001 | Lewis |
| 6,175,752 B1 | 1/2001 | Say et al. |
| 6,180,416 B1 | 1/2001 | Kurnik et al. |
| 6,186,145 B1 | 2/2001 | Brown |
| 6,187,062 B1 | 2/2001 | Oweis et al. |
| 6,189,536 B1 | 2/2001 | Martinez et al. |
| 6,192,891 B1 | 2/2001 | Gravel et al. |
| 6,193,873 B1 | 2/2001 | Ohara et al. |
| 6,196,970 B1 | 3/2001 | Brown |
| 6,198,957 B1 | 3/2001 | Green |
| 6,200,265 B1 | 3/2001 | Walsh et al. |
| 6,200,772 B1 | 3/2001 | Vadgama et al. |
| 6,201,979 B1 | 3/2001 | Kurnik et al. |
| 6,201,980 B1 | 3/2001 | Darrow et al. |
| 6,201,993 B1 | 3/2001 | Kruse et al. |
| 6,206,841 B1 | 3/2001 | Cunningham et al. |
| 6,206,856 B1 | 3/2001 | Mahurkar |
| 6,207,400 B1 | 3/2001 | Kwon |
| 6,208,894 B1 | 3/2001 | Schulman et al. |
| 6,210,272 B1 | 4/2001 | Brown |
| 6,210,976 B1 | 4/2001 | Sabbadini |
| 6,212,416 B1 | 4/2001 | Ward et al. |
| 6,212,424 B1 | 4/2001 | Robinson |
| 6,214,185 B1 | 4/2001 | Offenbacher et al. |
| 6,219,565 B1 | 4/2001 | Cupp et al. |
| 6,219,574 B1 | 4/2001 | Cormier et al. |
| 6,223,083 B1 | 4/2001 | Rosar |
| 6,223,471 B1 | 5/2001 | Barber |
| 6,224,745 B1 | 5/2001 | Baltruschat |
| 6,230,059 B1 | 5/2001 | Duffin |
| 6,231,879 B1 | 5/2001 | Li et al. |
| 6,232,130 B1 | 5/2001 | Wolf |
| 6,232,370 B1 | 5/2001 | Kubota et al. |
| 6,232,783 B1 | 5/2001 | Merrill |
| 6,233,080 B1 | 5/2001 | Brenner et al. |
| 6,233,471 B1 | 5/2001 | Berner et al. |
| 6,233,539 B1 | 5/2001 | Brown |
| 6,239,925 B1 | 5/2001 | Ardrey et al. |
| 6,241,704 B1 | 6/2001 | Peterson et al. |
| 6,241,862 B1 | 6/2001 | McAleer et al. |
| 6,241,863 B1 | 6/2001 | Monbouquette |
| 6,246,330 B1 | 6/2001 | Nielsen |
| 6,246,992 B1 | 6/2001 | Brown |
| 6,248,065 B1 | 6/2001 | Brown |
| 6,248,067 B1 | 6/2001 | Causey, III et al. |
| 6,248,093 B1 | 6/2001 | Moberg |
| 6,251,260 B1 | 6/2001 | Heller et al. |
| 6,251,280 B1 | 6/2001 | Dai et al. |
| 6,252,032 B1 | 6/2001 | Van Antwerp et al. |
| 6,253,804 B1 | 7/2001 | Safabash |
| 6,254,586 B1 | 7/2001 | Mann et al. |
| 6,256,522 B1 | 7/2001 | Schultz |
| 6,256,643 B1 | 7/2001 | Cork et al. |
| 6,259,587 B1 | 7/2001 | Sheldon et al. |
| 6,259,937 B1 | 7/2001 | Schulman et al. |
| 6,260,022 B1 | 7/2001 | Brown |
| 6,264,825 B1 | 7/2001 | Blackburn et al. |
| 6,266,645 B1 | 7/2001 | Simpson |
| 6,267,724 B1 | 7/2001 | Taylor |
| 6,268,161 B1 | 7/2001 | Han et al. |
| 6,268,913 B1 | 7/2001 | Rising |
| 6,270,445 B1 | 8/2001 | Dean, Jr. et al. |
| 6,272,364 B1 | 8/2001 | Kurnik |
| 6,272,480 B1 | 8/2001 | Tresp et al. |
| 6,274,285 B1 | 8/2001 | Gries et al. |
| 6,274,686 B1 | 8/2001 | Mosbach |
| 6,275,717 B1 | 8/2001 | Gross et al. |
| 6,280,416 B1 | 8/2001 | Van Antwerp et al. |
| 6,280,587 B1 | 8/2001 | Matsumoto |
| 6,281,006 B1 | 8/2001 | Heller et al. |
| 6,283,943 B1 | 9/2001 | Dy et al. |
| 6,284,126 B1 | 9/2001 | Kurnik et al. |
| 6,285,897 B1 | 9/2001 | Kilcoyne et al. |
| 6,289,238 B1 | 9/2001 | Besson et al. |
| 6,293,925 B1 | 9/2001 | Safabash et al. |
| 6,294,281 B1 | 9/2001 | Heller |
| 6,295,463 B1 | 9/2001 | Stenzler |
| 6,295,506 B1 | 9/2001 | Heinonen et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,300,002 B1 | 10/2001 | Webb et al. |
| 6,301,499 B1 | 10/2001 | Carlson et al. |
| 6,304,766 B1 | 10/2001 | Colvin, Jr. et al. |
| 6,309,351 B1 | 10/2001 | Kurnik et al. |
| 6,309,384 B1 | 10/2001 | Harrington et al. |
| 6,309,526 B1 | 10/2001 | Fujiwara et al. |
| 6,309,884 B1 | 10/2001 | Cooper et al. |
| 6,310,110 B1 | 10/2001 | Markowitz et al. |
| 6,315,721 B2 | 11/2001 | Schulman et al. |
| 6,315,738 B1 | 11/2001 | Nishikawa et al. |
| 6,319,540 B1 | 11/2001 | Van Antwerp et al. |
| 6,319,566 B1 | 11/2001 | Polanyi et al. |
| 6,320,357 B1 | 11/2001 | Peters et al. |
| 6,324,428 B1 | 11/2001 | Weinberg et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 * | 12/2001 | Heller et al. .................. 435/14 |
| 6,329,929 B1 | 12/2001 | Weijand et al. |
| 6,330,426 B2 | 12/2001 | Brown et al. |
| 6,330,464 B1 | 12/2001 | Colvin, Jr. et al. |
| 6,331,518 B2 | 12/2001 | Hemm et al. |
| 6,334,778 B1 | 1/2002 | Brown |
| 6,336,900 B1 | 1/2002 | Alleckson et al. |
| 6,338,790 B1 | 1/2002 | Feldman et al. |
| 6,340,421 B1 | 1/2002 | Vachon et al. |
| 6,341,232 B1 | 1/2002 | Conn et al. |
| 6,343,225 B1 | 1/2002 | Clark, Jr. |
| 6,356,776 B1 | 3/2002 | Berner et al. |
| 6,358,237 B1 | 3/2002 | Paukovits et al. |
| 6,360,888 B1 | 3/2002 | McIvor et al. |
| 6,363,282 B1 | 3/2002 | Nichols et al. |
| 6,365,670 B1 | 4/2002 | Fry |
| 6,366,793 B1 | 4/2002 | Bell et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,370,410 B2 | 4/2002 | Kurnik et al. |
| 6,379,301 B1 | 4/2002 | Worthington et al. |
| 6,379,317 B1 | 4/2002 | Kintzig et al. |
| 6,383,767 B1 | 5/2002 | Polak |
| 6,387,048 B1 | 5/2002 | Schulman et al. |
| 6,391,643 B1 | 5/2002 | Chen et al. |
| 6,393,318 B1 | 5/2002 | Conn et al. |
| 6,398,562 B1 | 6/2002 | Butler et al. |
| 6,398,727 B1 | 6/2002 | Bui et al. |
| 6,402,689 B1 | 6/2002 | Scarantino et al. |
| 6,402,691 B1 | 6/2002 | Peddicord et al. |
| 6,405,066 B1 | 6/2002 | Essenpreis et al. |
| 6,406,066 B1 | 6/2002 | Uegene |
| 6,406,426 B1 | 6/2002 | Reuss et al. |
| 6,409,674 B1 | 6/2002 | Brockway et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,424,867 B1 | 7/2002 | Snell et al. |
| 6,427,088 B1 | 7/2002 | Bowman, IV et al. |

| | | | | | | | |
|---|---|---|---|---|---|---|---|
| 6,434,409 | B1 | 8/2002 | Pfeiffer et al. | 6,560,471 | B1 | 5/2003 | Heller et al. |
| 6,438,414 | B1 | 8/2002 | Conn et al. | 6,561,978 | B1 | 5/2003 | Conn et al. |
| 6,440,068 | B1 | 8/2002 | Brown et al. | 6,562,001 | B2 | 5/2003 | Lebel et al. |
| 6,442,433 | B1 | 8/2002 | Linberg | 6,564,105 | B2 | 5/2003 | Starkweather et al. |
| 6,442,637 | B1 | 8/2002 | Hawkins et al. | 6,565,509 | B1 | 5/2003 | Say et al. |
| 6,443,942 | B2 | 9/2002 | Van Antwerp et al. | 6,569,521 | B1 | 5/2003 | Sheridan et al. |
| 6,447,448 | B1 | 9/2002 | Ishikawa et al. | 6,571,128 | B2 | 5/2003 | Lebel et al. |
| 6,447,542 | B1 | 9/2002 | Weadock | 6,571,200 | B1 | 5/2003 | Mault |
| 6,454,710 | B1 | 9/2002 | Ballerstadt et al. | 6,572,545 | B2 | 6/2003 | Knobbe et al. |
| 6,459,917 | B1 | 10/2002 | Gowda et al. | 6,574,490 | B2 | 6/2003 | Abbink et al. |
| 6,461,496 | B1 | 10/2002 | Feldman et al. | 6,575,905 | B2 | 6/2003 | Knobbe et al. |
| 6,462,162 | B2 | 10/2002 | Van Antwerp et al. | 6,576,101 | B1 | 6/2003 | Heller et al. |
| 6,464,687 | B1 | 10/2002 | Ishikawa et al. | 6,576,117 | B1 | 6/2003 | Iketaki et al. |
| 6,464,848 | B1 | 10/2002 | Matsumoto | 6,577,899 | B2 | 6/2003 | Lebel et al. |
| 6,466,810 | B1 | 10/2002 | Ward et al. | 6,579,498 | B1 | 6/2003 | Eglise |
| 6,468,222 | B1 | 10/2002 | Mault et al. | 6,579,690 | B1 | 6/2003 | Bonnecaze et al. |
| 6,469,526 | B1 | 10/2002 | Franklin | 6,584,335 | B1 | 6/2003 | Haar et al. |
| 6,471,645 | B1 | 10/2002 | Warkentin et al. | 6,585,644 | B2 | 7/2003 | Lebel et al. |
| 6,471,689 | B1 | 10/2002 | Joseph et al. | 6,585,675 | B1 | 7/2003 | O'Mahony et al. |
| 6,472,122 | B1 | 10/2002 | Schulman et al. | 6,585,763 | B1 | 7/2003 | Keilman et al. |
| 6,475,180 | B2 | 11/2002 | Peterson et al. | 6,587,705 | B1 | 7/2003 | Kim et al. |
| 6,475,750 | B1 | 11/2002 | Han et al. | 6,588,644 | B2 | 7/2003 | Simon |
| 6,477,392 | B1 | 11/2002 | Honigs et al. | 6,589,205 | B1 | 7/2003 | Meadows |
| 6,477,395 | B2 | 11/2002 | Schulman et al. | 6,589,229 | B1 | 7/2003 | Connelly et al. |
| 6,478,736 | B1 | 11/2002 | Mault | 6,591,125 | B1 | 7/2003 | Buse et al. |
| 6,480,730 | B2 | 11/2002 | Darrow et al. | 6,591,126 | B2 | 7/2003 | Roeper et al. |
| 6,481,440 | B2 | 11/2002 | Gielen et al. | 6,594,514 | B2 | 7/2003 | Berner et al. |
| 6,482,158 | B2 | 11/2002 | Mault | 6,595,919 | B2 | 7/2003 | Berner et al. |
| 6,482,604 | B2 | 11/2002 | Kwon | 6,595,929 | B2 | 7/2003 | Stivoric et al. |
| 6,484,045 | B1 | 11/2002 | Holker et al. | 6,602,678 | B2 | 8/2003 | Kwon et al. |
| 6,484,046 | B1 | 11/2002 | Say et al. | 6,602,909 | B1 | 8/2003 | Jarowski |
| 6,485,138 | B1 | 11/2002 | Kubota et al. | 6,605,072 | B2 | 8/2003 | Struys et al. |
| 6,485,465 | B2 | 11/2002 | Moberg et al. | 6,605,200 | B1 | 8/2003 | Mao et al. |
| 6,494,830 | B1 | 12/2002 | Wessel | 6,605,201 | B1 | 8/2003 | Mao et al. |
| 6,496,728 | B2 | 12/2002 | Li et al. | 6,607,509 | B2 | 8/2003 | Bobroff et al. |
| 6,498,043 | B1 | 12/2002 | Schulman et al. | 6,607,658 | B1 | 8/2003 | Heller et al. |
| 6,498,941 | B1 | 12/2002 | Jackson | 6,610,012 | B2 | 8/2003 | Mault |
| 6,505,059 | B1 | 1/2003 | Kollias et al. | 6,612,306 | B1 | 9/2003 | Mault |
| 6,512,939 | B1 | 1/2003 | Colvin et al. | 6,612,984 | B1 | 9/2003 | Kerr |
| 6,513,532 | B2 | 2/2003 | Mault et al. | 6,613,379 | B2 | 9/2003 | Ward et al. |
| 6,514,718 | B2 | 2/2003 | Heller et al. | 6,615,078 | B1 | 9/2003 | Burson et al. |
| 6,515,593 | B1 | 2/2003 | Stark et al. | 6,616,819 | B1 | 9/2003 | Liamos et al. |
| 6,520,326 | B2 | 2/2003 | McIvor et al. | 6,618,603 | B2 | 9/2003 | Varalli et al. |
| 6,520,997 | B1 | 2/2003 | Pekkarinen et al. | 6,618,934 | B1 | 9/2003 | Feldman et al. |
| 6,526,298 | B1 | 2/2003 | Khalil et al. | 6,620,106 | B2 | 9/2003 | Mault |
| 6,527,729 | B1 | 3/2003 | Turcott | 6,627,058 | B1 | 9/2003 | Chan |
| 6,528,584 | B2 | 3/2003 | Kennedy et al. | 6,629,776 | B2 | 10/2003 | Bell et al. |
| 6,529,755 | B2 | 3/2003 | Kurnik et al. | 6,629,934 | B2 | 10/2003 | Mault et al. |
| 6,529,772 | B2 | 3/2003 | Carlson et al. | 6,633,772 | B2 | 10/2003 | Ford et al. |
| 6,530,915 | B1 | 3/2003 | Eppstein et al. | 6,635,014 | B2 | 10/2003 | Starkweather et al. |
| 6,534,322 | B1 | 3/2003 | Sabbadini | 6,635,167 | B2 | 10/2003 | Batman et al. |
| 6,534,323 | B1 | 3/2003 | Sabbadini | 6,641,533 | B2 | 11/2003 | Causey, III et al. |
| 6,535,753 | B1 | 3/2003 | Raskas | 6,642,015 | B2 | 11/2003 | Vachon et al. |
| 6,537,243 | B1 | 3/2003 | Henning et al. | 6,644,321 | B1 | 11/2003 | Behm |
| 6,537,318 | B1 | 3/2003 | Ita et al. | 6,645,142 | B2 | 11/2003 | Braig et al. |
| 6,540,675 | B2 | 4/2003 | Aceti et al. | 6,645,181 | B1 | 11/2003 | Lavi et al. |
| 6,541,107 | B1 | 4/2003 | Zhong et al. | 6,648,821 | B2 | 11/2003 | Lebel et al. |
| 6,544,212 | B2 | 4/2003 | Galley et al. | 6,653,091 | B1 | 11/2003 | Dunn et al. |
| 6,545,085 | B2 | 4/2003 | Kilgour et al. | 6,654,625 | B1 | 11/2003 | Say et al. |
| 6,546,268 | B1 | 4/2003 | Ishikawa et al. | 6,659,948 | B2 | 12/2003 | Lebel et al. |
| 6,546,269 | B1 | 4/2003 | Kurnik | 6,668,196 | B1 | 12/2003 | Villegas et al. |
| 6,547,839 | B2 | 4/2003 | Zhang et al. | 6,671,554 | B2 | 12/2003 | Gibson et al. |
| 6,549,796 | B2 | 4/2003 | Sohrab | 6,673,596 | B1 | 1/2004 | Sayler et al. |
| 6,551,276 | B1 | 4/2003 | Mann et al. | 6,673,625 | B2 | 1/2004 | Satcher, Jr. et al. |
| 6,551,494 | B1 | 4/2003 | Heller et al. | 6,682,938 | B1 | 1/2004 | Satcher, Jr. et al. |
| 6,551,496 | B1 | 4/2003 | Moles et al. | 6,683,040 | B2 | 1/2004 | Bragulla et al. |
| 6,553,244 | B2 | 4/2003 | Lesho et al. | 6,683,535 | B1 | 1/2004 | Utke |
| 6,554,798 | B1 | 4/2003 | Mann et al. | 6,687,522 | B2 | 2/2004 | Tamada |
| 6,558,320 | B1 | 5/2003 | Causey, III et al. | 6,687,546 | B2 | 2/2004 | Lebel et al. |
| 6,558,321 | B1 | 5/2003 | Burd et al. | 6,689,056 | B1 | 2/2004 | Kilcoyne et al. |
| 6,558,351 | B1 | 5/2003 | Steil et al. | 6,689,091 | B2 | 2/2004 | Bui et al. |

| | | |
|---|---|---|
| 6,689,265 B2 | 2/2004 | Heller et al. |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,699,218 B2 | 3/2004 | Flaherty et al. |
| 6,699,383 B2 | 3/2004 | Lemire et al. |
| 6,702,857 B2 | 3/2004 | Brauker et al. |
| 6,704,587 B1 | 3/2004 | Kumar et al. |
| 6,705,833 B2 | 3/2004 | Tam et al. |
| 6,708,049 B1 | 3/2004 | Berson et al. |
| 6,711,423 B2 | 3/2004 | Colvin, Jr. |
| 6,721,587 B2 | 4/2004 | Gough |
| 6,723,046 B2 | 4/2004 | Lichtenstein et al. |
| 6,728,560 B2 | 4/2004 | Kollias et al. |
| 6,730,200 B1 | 5/2004 | Stewert et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,736,777 B2 | 5/2004 | Kim et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,773,565 B2 | 8/2004 | Kunimoto et al. |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,793,802 B2 | 9/2004 | Lee et al. |
| 6,794,195 B2 | 9/2004 | Colvin, Jr. |
| 6,799,149 B2 | 9/2004 | Hartlaub |
| 6,800,451 B2 | 10/2004 | Daniloff et al. |
| 6,801,041 B2 | 10/2004 | Karinka et al. |
| 6,801,420 B2 | 10/2004 | Talbot et al. |
| 6,802,957 B2 | 10/2004 | Jung et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,516 B2 | 11/2004 | Ujhelyi et al. |
| 6,813,519 B2 | 11/2004 | Lebel et al. |
| 6,815,186 B2 | 11/2004 | Clark, Jr. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,500 B1 | 2/2005 | Hoss et al. |
| 6,852,694 B2 | 2/2005 | Van Antwerp et al. |
| 6,853,854 B1 | 2/2005 | Proniewicz et al. |
| 6,855,115 B2 | 2/2005 | Fonseca et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,872,200 B2 | 3/2005 | Mann et al. |
| 6,873,268 B2 | 3/2005 | Lebel et al. |
| 6,875,386 B1 | 4/2005 | Ward et al. |
| 6,879,849 B2 | 4/2005 | Begic |
| 6,881,551 B2 | 4/2005 | Heller et al. |
| 6,882,940 B2 | 4/2005 | Potts et al. |
| 6,885,883 B2 | 4/2005 | Parris et al. |
| 6,891,317 B2 | 5/2005 | Pei et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,899,683 B2 | 5/2005 | Mault et al. |
| 6,899,684 B2 | 5/2005 | Mault et al. |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |
| 6,922,578 B2 | 7/2005 | Eppstein et al. |
| 6,922,584 B2 | 7/2005 | Wang et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,927,246 B2 | 8/2005 | Noronha et al. |
| 6,931,327 B2 | 8/2005 | Goode, Jr. et al. |
| 6,932,084 B2 | 8/2005 | Estes et al. |
| 6,932,894 B2 | 8/2005 | Mao et al. |
| 6,936,006 B2 | 8/2005 | Sabra |
| 6,936,029 B2 | 8/2005 | Mann et al. |
| 6,940,590 B2 | 9/2005 | Colvin, Jr. et al. |
| 6,941,163 B2 | 9/2005 | Ford et al. |
| 6,946,996 B2 | 9/2005 | Koyama |
| 6,950,708 B2 | 9/2005 | Bowman, IV et al. |
| 6,952,603 B2 | 10/2005 | Gerber et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,965,791 B1 | 11/2005 | Hitchcock et al. |
| 6,968,294 B2 | 11/2005 | Gutta et al. |
| 6,968,375 B1 | 11/2005 | Brown |
| 6,973,706 B2 | 12/2005 | Say et al. |
| 6,974,437 B2 | 12/2005 | Lebel et al. |
| 6,978,182 B2 | 12/2005 | Mazar et al. |
| 6,979,326 B2 | 12/2005 | Mann et al. |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,016,721 B2 | 3/2006 | Lee et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,029,444 B2 | 4/2006 | Shin et al. |
| 7,039,810 B1 | 5/2006 | Nichols |
| 7,041,468 B2 | 5/2006 | Drucker et al. |
| 7,049,277 B2 | 5/2006 | Bagulla et al. |

| | | | | | | |
|---|---|---|---|---|---|---|
| 7,052,472 | B1 | 5/2006 | Miller et al. | 2002/0026937 A1 | 3/2002 | Mault |
| 7,052,483 | B2 | 5/2006 | Wojcik | 2002/0027164 A1 | 3/2002 | Mault et al. |
| 7,056,302 | B2 | 6/2006 | Douglas | 2002/0028995 A1 | 3/2002 | Mault |
| 7,070,580 | B2 | 7/2006 | Nielsen | 2002/0040208 A1 | 4/2002 | Flaherty et al. |
| 7,072,718 | B2 | 7/2006 | VonArx et al. | 2002/0042090 A1 | 4/2002 | Heller et al. |
| 7,072,802 | B2 | 7/2006 | Hartlaub | 2002/0042561 A1 | 4/2002 | Schulman et al. |
| 7,074,307 | B2 | 7/2006 | Simpson et al. | 2002/0045808 A1 | 4/2002 | Ford et al. |
| 7,081,195 | B2 | 7/2006 | Simpson et al. | 2002/0047867 A1 | 4/2002 | Mault et al. |
| 7,082,334 | B2 | 7/2006 | Boute et al. | 2002/0053637 A1 | 5/2002 | Conn et al. |
| 7,098,803 | B2 | 8/2006 | Mann et al. | 2002/0062069 A1 | 5/2002 | Mault |
| 7,108,778 | B2 | 9/2006 | Simpson et al. | 2002/0063060 A1 | 5/2002 | Gascoyne et al. |
| 7,109,878 | B2 | 9/2006 | Mann et al. | 2002/0065453 A1 | 5/2002 | Lesho et al. |
| 7,110,803 | B2 | 9/2006 | Shults et al. | 2002/0068858 A1 | 6/2002 | Braig et al. |
| 7,113,821 | B1 | 9/2006 | Sun et al. | 2002/0068860 A1 | 6/2002 | Clark, Jr. |
| 7,115,884 | B1 | 10/2006 | Walt et al. | 2002/0072858 A1 | 6/2002 | Cheng |
| 7,133,710 | B2 | 11/2006 | Acosta et al. | 2002/0077765 A1 | 6/2002 | Mault |
| 7,134,999 | B2 | 11/2006 | Brauker et al. | 2002/0077766 A1 | 6/2002 | Mault |
| 7,136,689 | B2 | 11/2006 | Shults et al. | 2002/0081559 A1 | 6/2002 | Brown et al. |
| 7,137,964 | B2 | 11/2006 | Flaherty | 2002/0083461 A1 | 6/2002 | Hutcheson et al. |
| 7,150,975 | B2 | 12/2006 | Tamada et al. | 2002/0087056 A1 | 7/2002 | Accti et al. |
| 7,163,511 | B2 | 1/2007 | Conn et al. | 2002/0091312 A1 | 7/2002 | Berner et al. |
| 7,166,074 | B2 | 1/2007 | Reghabi et al. | 2002/0099282 A1 | 7/2002 | Knobbe et al. |
| 7,171,274 | B2 | 1/2007 | Starkweather et al. | 2002/0099997 A1 | 7/2002 | Piret |
| 7,177,690 | B2 | 2/2007 | Woods et al. | 2002/0103425 A1 | 8/2002 | Mault |
| 7,183,068 | B2 | 2/2007 | Burson et al. | 2002/0107433 A1 | 8/2002 | Mault |
| 7,183,102 | B2 | 2/2007 | Monfre et al. | 2002/0107476 A1 | 8/2002 | Mann et al. |
| 7,187,528 | B2 | 3/2007 | Talbot et al. | 2002/0109600 A1 | 8/2002 | Mault et al. |
| 7,189,341 | B2 | 3/2007 | Li et al. | 2002/0111547 A1 | 8/2002 | Knobbe et al. |
| 7,190,988 | B2 | 3/2007 | Say et al. | 2002/0119711 A1 | 8/2002 | Van Antwerp et al. |
| 7,192,450 | B2 | 3/2007 | Brauker et al. | 2002/0124017 A1 | 9/2002 | Mault |
| 7,198,606 | B2 | 4/2007 | Boecker et al. | 2002/0128594 A1 | 9/2002 | Das et al. |
| 7,203,549 | B2 | 4/2007 | Schommer et al. | 2002/0130042 A1 | 9/2002 | Moerman et al. |
| 7,207,974 | B2 | 4/2007 | Safabash et al. | 2002/0133378 A1 | 9/2002 | Mault et al. |
| 7,226,978 | B2 | 6/2007 | Tapsak et al. | 2002/0151796 A1 | 10/2002 | Koulik |
| 7,228,163 | B2 | 6/2007 | Ackerman | 2002/0151816 A1 | 10/2002 | Rich et al. |
| 7,233,817 | B2 | 6/2007 | Yen | 2002/0155615 A1 | 10/2002 | Novikov et al. |
| 7,248,929 | B2 | 7/2007 | Meadows et al. | 2002/0161286 A1 | 10/2002 | Gerber et al. |
| 7,261,691 | B1 | 8/2007 | Asomani | 2002/0161288 A1 | 10/2002 | Shin et al. |
| 7,267,665 | B2 | 9/2007 | Steil et al. | 2002/0177764 A1 | 11/2002 | Sohrab |
| 7,276,029 | B2 | 10/2007 | Goode, Jr. et al. | 2002/0182241 A1 | 12/2002 | Boerenstein et al. |
| 7,295,867 | B2 | 11/2007 | Berner et al. | 2002/0193885 A1 | 12/2002 | Legeay et al. |
| 7,310,544 | B2 | 12/2007 | Brister et al. | 2002/0198513 A1 | 12/2002 | Lebel et al. |
| 2001/0011224 | A1 | 8/2001 | Brown | 2003/0004457 A1 | 1/2003 | Andersson |
| 2001/0016310 | A1 | 8/2001 | Brown et al. | 2003/0006669 A1 | 1/2003 | Pei et al. |
| 2001/0016682 | A1 | 8/2001 | Berner et al. | 2003/0023171 A1 | 1/2003 | Sato et al. |
| 2001/0016683 | A1 | 8/2001 | Darrow et al. | 2003/0023182 A1 | 1/2003 | Mault et al. |
| 2001/0020124 | A1 | 9/2001 | Tamada | 2003/0023317 A1 | 1/2003 | Brauker et al. |
| 2001/0029340 | A1 | 10/2001 | Mault et al. | 2003/0028089 A1 | 2/2003 | Galley et al. |
| 2001/0032278 | A1 | 10/2001 | Brown et al. | 2003/0028120 A1 | 2/2003 | Mault et al. |
| 2001/0037060 | A1 | 11/2001 | Thompson et al. | 2003/0032077 A1 | 2/2003 | Itoh et al. |
| 2001/0037069 | A1 | 11/2001 | Carlson et al. | 2003/0032867 A1 | 2/2003 | Crothall et al. |
| 2001/0039504 | A1 | 11/2001 | Linberg et al. | 2003/0032868 A1 | 2/2003 | Graskov et al. |
| 2001/0041830 | A1 | 11/2001 | Varalli et al. | 2003/0032874 A1 | 2/2003 | Rhodes et al. |
| 2001/0044581 | A1 | 11/2001 | Mault | 2003/0040683 A1 | 2/2003 | Rule et al. |
| 2001/0044588 | A1 | 11/2001 | Mault | 2003/0042137 A1 | 3/2003 | Mao et al. |
| 2001/0047125 | A1 | 11/2001 | Quy | 2003/0050537 A1 | 3/2003 | Wessel |
| 2001/0049096 | A1 | 12/2001 | Brown | 2003/0050546 A1 | 3/2003 | Desai et al. |
| 2001/0049470 | A1 | 12/2001 | Mault et al. | 2003/0059631 A1 | 3/2003 | Al-Lamee |
| 2002/0002326 | A1 | 1/2002 | Causey, III et al. | 2003/0065254 A1 | 4/2003 | Schulman et al. |
| 2002/0002328 | A1 | 1/2002 | Tamada | 2003/0065257 A1 | 4/2003 | Mault et al. |
| 2002/0004640 | A1 | 1/2002 | Conn et al. | 2003/0065273 A1 | 4/2003 | Mault et al. |
| 2002/0009810 | A1 | 1/2002 | O'Connor et al. | 2003/0065274 A1 | 4/2003 | Mault et al. |
| 2002/0010414 | A1 | 1/2002 | Coston et al. | 2003/0065275 A1 | 4/2003 | Mault et al. |
| 2002/0016530 | A1 | 2/2002 | Brown | 2003/0065308 A1 | 4/2003 | Lebel et al. |
| 2002/0019022 | A1 | 2/2002 | Dunn et al. | 2003/0076082 A1 | 4/2003 | Morgan et al. |
| 2002/0019330 | A1 | 2/2002 | Murray et al. | 2003/0078481 A1 | 4/2003 | McIvor et al. |
| 2002/0019586 | A1 | 2/2002 | Teller et al. | 2003/0078560 A1 | 4/2003 | Miller et al. |
| 2002/0019748 | A1 | 2/2002 | Brown | 2003/0097082 A1 | 5/2003 | Purdy et al. |
| 2002/0022883 | A1 | 2/2002 | Burg | 2003/0100040 A1 | 5/2003 | Bonnecaze et al. |
| 2002/0023852 | A1 | 2/2002 | McIvor et al. | 2003/0100821 A1 | 5/2003 | Heller et al. |
| 2002/0026111 | A1 | 2/2002 | Ackerman | 2003/0105407 A1 | 6/2003 | Pearce et al. |

| Pub. No. | Date | Inventor |
|---|---|---|
| 2003/0108976 A1 | 6/2003 | Braig et al. |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0168338 A1 | 9/2003 | Gao et al. |
| 2003/0175806 A1 | 9/2003 | Rule et al. |
| 2003/0176183 A1 | 9/2003 | Drucker et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0188427 A1 | 10/2003 | Say et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199744 A1 | 10/2003 | Buse et al. |
| 2003/0199791 A1 | 10/2003 | Boecker et al. |
| 2003/0199903 A1 | 10/2003 | Boecker et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0211625 A1 | 11/2003 | Cohan |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0225437 A1 | 12/2003 | Ferguson |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015134 A1 | 1/2004 | Lavi et al. |
| 2004/0018486 A1 | 1/2004 | Dunn et al. |
| 2004/0030285 A1 | 2/2004 | Lavi et al. |
| 2004/0030294 A1 | 2/2004 | Mahurkar |
| 2004/0039256 A1 | 2/2004 | Kawatahara et al. |
| 2004/0039406 A1 | 2/2004 | Jessen |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0068230 A1 | 4/2004 | Estes et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0074785 A1 | 4/2004 | Holker |
| 2004/0078219 A1 | 4/2004 | Kaylor |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0108226 A1 | 6/2004 | Polychronakos et al. |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0138588 A1 | 7/2004 | Saikley et al. |
| 2004/0153585 A1 | 8/2004 | Kawatahara et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0172284 A1 | 9/2004 | Sullivan et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Von Arx et al. |
| 2004/0263354 A1 | 12/2004 | Mann et al. |
| 2005/0003470 A1 | 1/2005 | Nelson et al. |
| 2005/0010087 A1 | 1/2005 | Banet et al. |
| 2005/0010269 A1 | 1/2005 | Lebel et al. |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0049473 A1 | 3/2005 | Desai et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0112169 A1 | 5/2005 | Brauker et al. |
| 2005/0113657 A1 | 5/2005 | Alarcon et al. |
| 2005/0113658 A1 | 5/2005 | Jacobson et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0131346 A1 | 6/2005 | Douglas |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Kieth et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |

| | | | | | | |
|---|---|---|---|---|---|---|
| 2005/0203707 A1 | 9/2005 | Tsutsui et al. | | 2007/0016381 A1 | 1/2007 | Kamath et al. |
| 2005/0214892 A1 | 9/2005 | Kovatchev et al. | | 2007/0017805 A1 | 1/2007 | Hodges et al. |
| 2005/0215871 A1 | 9/2005 | Feldman et al. | | 2007/0027381 A1 | 2/2007 | Stafford |
| 2005/0215872 A1 | 9/2005 | Berner et al. | | 2007/0027384 A1 | 2/2007 | Brister et al. |
| 2005/0239154 A1 | 10/2005 | Feldman et al. | | 2007/0027385 A1 | 2/2007 | Brister et al. |
| 2005/0239156 A1 | 10/2005 | Drucker et al. | | 2007/0032706 A1 | 2/2007 | Kamath et al. |
| 2005/0242479 A1 | 11/2005 | Petisce et al. | | 2007/0032717 A1 | 2/2007 | Brister et al. |
| 2005/0245795 A1 | 11/2005 | Goode, Jr. et al. | | 2007/0032718 A1 | 2/2007 | Shults et al. |
| 2005/0245799 A1 | 11/2005 | Brauker et al. | | 2007/0045902 A1 | 3/2007 | Brauker et al. |
| 2005/0251083 A1 | 11/2005 | Carr-Brendel et al. | | 2007/0060814 A1 | 3/2007 | Stafford |
| 2005/0261563 A1 | 11/2005 | Zhou et al. | | 2007/0066873 A1 | 3/2007 | Kamath et al. |
| 2005/0261660 A1 | 11/2005 | Choi | | 2007/0078320 A1 | 4/2007 | Stafford |
| 2005/0267780 A1 | 12/2005 | Ray et al. | | 2007/0078321 A1 | 4/2007 | Mazza et al. |
| 2005/0271546 A1 | 12/2005 | Gerber et al. | | 2007/0093704 A1 | 4/2007 | Brister et al. |
| 2005/0271547 A1 | 12/2005 | Gerber et al. | | 2007/0106135 A1 | 5/2007 | Sloan et al. |
| 2005/0272640 A1 | 12/2005 | Doyle, III et al. | | 2007/0149873 A1 | 6/2007 | Say et al. |
| 2005/0272985 A1 | 12/2005 | Kotulla et al. | | 2007/0149874 A1 | 6/2007 | Say et al. |
| 2005/0277164 A1 | 12/2005 | Drucker et al. | | 2007/0151869 A1 | 7/2007 | Heller et al. |
| 2005/0287620 A1 | 12/2005 | Heller et al. | | 2007/0161879 A1 | 7/2007 | Say et al. |
| 2006/0001538 A1 | 1/2006 | Kraft et al. | | 2007/0161880 A1 | 7/2007 | Say et al. |
| 2006/0001550 A1 | 1/2006 | Mann et al. | | 2007/0163880 A1 | 7/2007 | Woo et al. |
| 2006/0001551 A1 | 1/2006 | Kraft et al. | | 2007/0179370 A1 | 8/2007 | Say et al. |
| 2006/0003398 A1 | 1/2006 | Heller et al. | | 2007/0179372 A1 | 8/2007 | Say et al. |
| 2006/0004271 A1 | 1/2006 | Peyser et al. | | 2007/0191699 A1 | 8/2007 | Say et al. |
| 2006/0007017 A1 | 1/2006 | Mann et al. | | 2007/0191700 A1 | 8/2007 | Say et al. |
| 2006/0015020 A1 | 1/2006 | Neale et al. | | 2007/0197889 A1 | 8/2007 | Brister et al. |
| 2006/0015024 A1 | 1/2006 | Brister et al. | | 2007/0197890 A1 | 8/2007 | Boock et al. |
| 2006/0016700 A1 | 1/2006 | Brister et al. | | 2007/0203408 A1 | 8/2007 | Say et al. |
| 2006/0019327 A1 | 1/2006 | Brister et al. | | 2007/0203410 A1 | 8/2007 | Say et al. |
| 2006/0020186 A1 | 1/2006 | Brister et al. | | 2007/0203411 A1 | 8/2007 | Say et al. |
| 2006/0020187 A1 | 1/2006 | Brister et al. | | 2007/0203966 A1 | 8/2007 | Brauker et al. |
| 2006/0020188 A1 | 1/2006 | Kamath et al. | | 2007/0208244 A1 | 9/2007 | Brauker et al. |
| 2006/0020189 A1 | 1/2006 | Brister et al. | | 2007/0208245 A1 | 9/2007 | Brauker et al. |
| 2006/0020190 A1 | 1/2006 | Kamath et al. | | 2007/0208246 A1 | 9/2007 | Brauker et al. |
| 2006/0020191 A1 | 1/2006 | Brister et al. | | 2007/0208247 A1 | 9/2007 | Say et al. |
| 2006/0020192 A1 | 1/2006 | Brister et al. | | 2007/0213610 A1 | 9/2007 | Say et al. |
| 2006/0025663 A1 | 2/2006 | Talbot et al. | | 2007/0215491 A1 | 9/2007 | Heller et al. |
| 2006/0031094 A1 | 2/2006 | Cohen et al. | | 2007/0218097 A1 | 9/2007 | Heller et al. |
| 2006/0036139 A1 | 2/2006 | Brister et al. | | 2007/0235331 A1 | 10/2007 | Simpson et al. |
| 2006/0036140 A1 | 2/2006 | Brister et al. | | 2007/0244380 A1 | 10/2007 | Say et al. |
| 2006/0036141 A1 | 2/2006 | Kamath et al. | | 2007/0249919 A1 | 10/2007 | Say et al. |
| 2006/0036142 A1 | 2/2006 | Brister et al. | | 2007/0249920 A1 | 10/2007 | Say et al. |
| 2006/0036143 A1 | 2/2006 | Brister et al. | | 2007/0249922 A1 | 10/2007 | Peyser et al. |
| 2006/0036144 A1 | 2/2006 | Brister et al. | | 2008/0167543 A1 | 7/2008 | Say et al. |
| 2006/0036145 A1 | 2/2006 | Brister et al. | | 2008/0214914 A1 | 9/2008 | Say et al. |
| 2006/0036187 A1 | 2/2006 | Vos et al. | | | | |
| 2006/0040402 A1 | 2/2006 | Brauker et al. | | | FOREIGN PATENT DOCUMENTS | |
| 2006/0052679 A1 | 3/2006 | Kotulla et al. | | | | |
| 2006/0058602 A1 | 3/2006 | Kwiatkowski et al. | | EP | 0125139 | 11/1984 |
| 2006/0063218 A1 | 3/2006 | Bartkowiak et al. | | EP | 0127958 | 12/1984 |
| 2006/0068208 A1 | 3/2006 | Tapsak et al. | | EP | 0136362 | 4/1985 |
| 2006/0074564 A1 | 4/2006 | Bartowiak et al. | | EP | 0170375 | 2/1986 |
| 2006/0086624 A1 | 4/2006 | Tapsak et al. | | EP | 0177743 | 4/1986 |
| 2006/0155180 A1 | 7/2006 | Brister et al. | | EP | 0184909 | 6/1986 |
| 2006/0173444 A1 | 8/2006 | Choy et al. | | EP | 0206218 | 12/1986 |
| 2006/0189856 A1 | 8/2006 | Petisce et al. | | EP | 0230472 | 8/1987 |
| 2006/0189863 A1 | 8/2006 | Peyser et al. | | EP | 0241309 | 10/1987 |
| 2006/0195029 A1 | 8/2006 | Shults et al. | | EP | 0245073 | 11/1987 |
| 2006/0198864 A1 | 9/2006 | Shults et al. | | EP | 0255291 | 2/1988 |
| 2006/0200019 A1 | 9/2006 | Petisce et al. | | EP | 0278647 | 8/1988 |
| 2006/0200020 A1 | 9/2006 | Brister et al. | | EP | 0 320 109 | 6/1989 |
| 2006/0200022 A1 | 9/2006 | Brauker et al. | | EP | 0 353 328 | 2/1990 |
| 2006/0211921 A1 | 9/2006 | Brauker et al. | | EP | 0359831 | 3/1990 |
| 2006/0222566 A1 | 10/2006 | Brauker et al. | | EP | 0368209 | 5/1990 |
| 2006/0224108 A1 | 10/2006 | Brauker et al. | | EP | 0368290 | 5/1990 |
| 2006/0235285 A1 | 10/2006 | Brister et al. | | EP | 0390390 | 10/1990 |
| 2006/0247985 A1 | 11/2006 | Liamos et al. | | EP | 0 390 390 | 10/1990 |
| 2006/0258761 A1 | 11/2006 | Boock et al. | | EP | 0 396 788 | 11/1990 |
| 2006/0258929 A1 | 11/2006 | Goode, Jr. et al. | | EP | 0400918 | 12/1990 |
| 2006/0270922 A1 | 11/2006 | Brauker et al. | | EP | 0453283 | 10/1991 |
| 2006/0270923 A1 | 11/2006 | Brauker et al. | | EP | 0512122 | 11/1992 |
| | | | | EP | 0535898 | 4/1993 |

| | | | | | |
|---|---|---|---|---|---|
| EP | 0539625 | 5/1993 | WO | WO-97/41421 | 11/1997 |
| EP | 0561966 | 10/1994 | WO | WO-97/42882 | 11/1997 |
| EP | 0776628 | 6/1997 | WO | WO-97/42883 | 11/1997 |
| EP | 0800082 | 10/1997 | WO | WO-97/42886 | 11/1997 |
| EP | 0817809 | 1/1998 | WO | WO-97/42888 | 11/1997 |
| EP | 0838230 | 4/1998 | WO | WO-97/43962 | 11/1997 |
| EP | 0880936 | 12/1998 | WO | WO-97/46868 | 12/1997 |
| EP | 0885932 | 12/1998 | WO | WO-98/09167 | 3/1998 |
| EP | 0967788 | 12/1999 | WO | WO-98/24358 | 6/1998 |
| EP | 0970655 | 1/2000 | WO | WO-98/24366 | 6/1998 |
| EP | 1034734 | 9/2000 | WO | WO-98/52045 | 11/1998 |
| EP | 1 048 264 | 11/2000 | WO | WO-98/52293 | 11/1998 |
| EP | 1077634 | 2/2001 | WO | WO-99/05966 | 2/1999 |
| EP | 1078258 | 2/2001 | WO | WO-99/32883 | 7/1999 |
| GB | 1394171 | 5/1975 | WO | WO-99/48419 | 9/1999 |
| GB | 1442303 | 7/1976 | WO | WO-99/56613 | 11/1999 |
| GB | 1579690 | 11/1980 | WO | WO 99/56613 | 11/1999 |
| GB | 1599241 | 9/1981 | WO | WO-99/58051 | 11/1999 |
| GB | 2073891 | 10/1981 | WO | WO-99/58973 | 11/1999 |
| GB | 2 149 918 | 6/1985 | WO | WO-00/13580 | 3/2000 |
| GB | 2154003 | 8/1985 | WO | WO-00/18294 | 4/2000 |
| GB | 2194892 | 3/1988 | WO | WO-00/19887 | 4/2000 |
| GB | 2204408 | 11/1988 | WO | WO-00/20626 | 4/2000 |
| GB | 2225637 | 6/1990 | WO | WO-00/32098 | 6/2000 |
| GB | 2254436 | 10/1992 | WO | WO-00/33065 | 6/2000 |
| JP | 55-010581 | 1/1980 | WO | WO 00/49940 | 8/2000 |
| JP | 55-010583 | 1/1980 | WO | WO 00/59370 | 10/2000 |
| JP | 55-010584 | 1/1980 | WO | WO-00/59373 | 10/2000 |
| JP | 56-163447 | 12/1981 | WO | WO-00/62664 | 10/2000 |
| JP | 62-083849 | 4/1987 | WO | WO-00/62665 | 10/2000 |
| JP | 63-139246 | 6/1988 | WO | WO-00/78210 | 12/2000 |
| JP | 6-190050 | 7/1994 | WO | WO-00/78992 | 12/2000 |
| JP | 8-154903 | 6/1996 | WO | WO-01/12158 | 2/2001 |
| JP | 2002-189015 | 7/2002 | WO | WO-01/20019 | 3/2001 |
| WO | WO-85/05119 | 11/1985 | WO | WO-01/20334 | 3/2001 |
| WO | WO-86/00513 | 1/1986 | WO | WO-01/24038 | 4/2001 |
| WO | WO-87/00513 | 1/1987 | WO | WO-01/33216 | 5/2001 |
| WO | WO-87/06040 | 10/1987 | WO | WO-01/43660 | 6/2001 |
| WO | WO-89/02246 | 3/1989 | WO | WO-01/52727 | 7/2001 |
| WO | WO-89/05119 | 6/1989 | WO | WO-01/52935 | 7/2001 |
| WO | WO-89/08713 | 9/1989 | WO | WO-01/54753 | 8/2001 |
| WO | WO-90/00367 | 1/1990 | WO | WO-01/57238 | 8/2001 |
| WO | WO-90/00738 | 1/1990 | WO | WO-01/57239 | 8/2001 |
| WO | WO-90/05300 | 5/1990 | WO | WO-01/58348 | 8/2001 |
| WO | WO-90/05910 | 5/1990 | WO | WO-01/67009 | 9/2001 |
| WO | WO-90/13021 | 11/1990 | WO | WO-01/68901 | 9/2001 |
| WO | WO-91/01680 | 2/1991 | WO | WO-01/69222 | 9/2001 |
| WO | WO-91/04704 | 4/1991 | WO | WO-01/88524 | 11/2001 |
| WO | WO-91/15993 | 10/1991 | WO | WO-01/88534 | 11/2001 |
| WO | WO-92/07525 | 5/1992 | WO | WO-02/16905 | 2/2002 |
| WO | WO-92/10584 | 6/1992 | WO | WO-02/17210 | 2/2002 |
| WO | WO-92/13271 | 8/1992 | WO | WO-02/24065 | 3/2002 |
| WO | WO-93/19701 | 10/1993 | WO | WO-02/058537 | 8/2002 |
| WO | WO-94/20602 | 9/1994 | WO | WO 02/058537 A2 | 8/2002 |
| WO | WO-94/22367 | 10/1994 | WO | WO-02/078512 | 10/2002 |
| WO | WO-94/27140 | 11/1994 | WO | WO-02/082989 | 10/2002 |
| WO | WO-95/06240 | 3/1995 | WO | WO-03/072269 | 9/2003 |
| WO | WO-95/07109 | 3/1995 | WO | WO-03/076893 | 9/2003 |
| WO | WO-96/01611 | 1/1996 | WO | WO-03/082091 | 10/2003 |
| WO | WO-96/07908 | 3/1996 | WO | WO-03/101862 | 12/2003 |
| WO | WO 96/14026 | 5/1996 | WO | WO-2004/061420 | 7/2004 |
| WO | WO 96/25089 | 8/1996 | WO | WO-2005/089103 | 9/2005 |
| WO | WO-96/30431 | 10/1996 | WO | WO-2006/119084 | 11/2006 |
| WO | WO-96/32076 | 10/1996 | WO | WO-2007/002189 | 1/2007 |
| WO | WO 96/35370 | 11/1996 | WO | WO-2007/016399 | 2/2007 |
| WO | WO-96/35370 | 11/1996 | WO | WO-2007/027381 | 3/2007 |
| WO | WO-96/36296 | 11/1996 | WO | WO-2007/027788 | 3/2007 |
| WO | WO 97/01986 | 1/1997 | WO | WO 2007/051139 | 5/2007 |
| WO | WO-97/02847 | 1/1997 | WO | WO-2007/053832 | 5/2007 |
| WO | WO-97/19344 | 5/1997 | WO | WO-2007/056638 | 5/2007 |
| WO | WO-97/20207 | 6/1997 | WO | WO-2007/120363 | 10/2007 |

OTHER PUBLICATIONS

Grant & Hackh's Chemical Dictionary, pp. 88, 89, 389, 390, and 398, 1987.*
Boedeker. web page of Bodedeker.com, Polyethylene Specifications, pp. 1–2, 2005.*
Shichiri et al., Diab. Nutr. Metab., 2:309–313, 1989.*
Sakaida et al. Sensors and Actuators B, 13–14: 319–322 (May–Jun. 1993).*
Sakakida et al. (II). Artif. Organs Today, 2(2) :145–158 (1992).*
Irish Patent Application No. 970443, filed Jun. 16, 1997.
Kaplan, 2004 "Wiley Electrical And Electronics Engineering Dictionary," John Wiley & Sons, Hoboken, New Jersey: p. 141–142, 548–549.
McKean, et al., 1988, "A Telemetry–Instrumentation System For Chronically Implanted Glucose And Oxygen Sensors," *IEE Transactions on Biomedical Engineering*, vol. 35, No. 7: p. 526–532.
Merriam–Webster's Medical Desk Dictionary, 2005, Merriam–Webster, Incorporated, Springfield, Massachusetts, U.S.A.: p. 843.
Merriam–Webster Unabridged Medical Dictionary, Definition: Protocol, http://unabridged.merriam–webster.com/cgi–bin/medical?va=protocol, Dec. 12, 2005.
Pishko, et al., 1991, "Amperometric Glucose Microelectrodes Prepared Through Immobilization Of Glucose Oxidase In Redox Hydrogels," *Analytical Chemistry*, vol. 63, No. 20: p. 2268–2272.
Schichiri, et al., 1985, "Needle–Type Glucose Sensor For Wearable Artificial Endocrine Pancreas," *Implantable Sensors for Closed–Loop Prosthetic Systems*, Chapter 15: p. 197–210.
Schichiri, et al., 1986, "Telemetry Glucose Monitoring Device With Needle–Type Glucose Sensor: A Useful Tool For Blood Glucose Monitoring In Diabetic Individuals," *Diabetes Care*, vol. 9, No. 3: p. 298–301.
Shults, et al., 1994, "A Telemetry–Instrumentation System for Monitoring Multiple Subcutaneously Implanted Glucose Sensors," *IEE Transactions On Biomedical Engineering*, vol. 14, No. 10: p. 937–942.
Updike, et al., 1997, "Principles Of Long–Term Fully Implanted Sensors With Emphasis On Radiotelmetric Monitoring Of Blood Glucose From Inside A Subcutaneous Foreign Body Capsule (FBC)," *Biosensors In The Body: Continuous In Vivo Monitoring*, Chapter 4: p. 117–137
Velho, et al., 1989, "Strategies For Calibrating A Subcutaneous Glucose Sensor," *Biomed.Biochim. Acia*, vol. 28, No. 11/12: p. 957–964.
Wilson, et al., 1992, "Progress Toward The Development Of An Implantable Sensor For Glucose," *Clinical Chemistry*, vol. 38, No. 9: p. 1613–1617.
Wiley Electrical and Electronics Engineering Dictionary, John Wiley & Sons, Inc. (2004), pp. 141, 142, 548, 549.
Pickup et al., "Responses and calibration of amperometric glucose sensors implanted in the subcutaneous tissue of man", Acta Diabetol. 30:143–148 (1993).
Aussedat et al., "A User–Friendly Method for Calibrating a Subcutaneous Glucose Sensor–Based Hypoglycaeemic Alarm," Biosensors & Bioelectronics, vol. 12, No. .11, pp. 1061–1071 (1997).
Petrou, et al., 2003, "Microdevice with Integrated Dialysis Probe and Biosensor Array for Multi–Analyte Monitoring Continuous," *Biosensors & Bioelectronics*, vol. 18: p. 613–619.
Poscia, et al., 2003, "A Microdialysis Technique for Continuous Subcutaneous Glucose Monitoring in Diabetic Patients (Part 1)," *Biosensors & Bioelectronics*, vol. 18: p. 891–898.
Varalli, et al., 2003, "A Microdialysis Technique for Continuous Subcutaneous Glucose Monitoring in Diabetic Patients (Part 2)," *Biosensors & Bioelectronics*, vol. 18: p. 899–905.
GJ Kemp, "Theoretical Aspects of One–Point Calibration," *Clinical Chemistry*, 30/7 1163–1167 (1984).
M. Sakakida et al., Development of Ferrocene–Mediated Needle–Type Glucose Sensor as a Measure of True Subcutaneous Tissue Glucose Concentrations, *Artif. Organs Today*, 2(1992) 145–148.
Takamura et al., Drug Release From Poly(Vinyl Alcohol) Gel Prepared By Freeze–Thaw Procedure, *J Controlled Release*, 20 (1992) 21–28.
Graham, "Poly(ethylene Oxide) and Related Hydrogels," *Hydrogels in Medicine and Pharmacy*, Chapter 4, CRC Press, 1987.
George S. Wilson et al., "Progress Toward the Development of an Implantable Sensor for Glucose," *Clinical Chemistry*, vol. 38, No. 9, 1992, pp. 1613–1617.
Mauras et al., "Lack of accuracy of continuous glucose sensors in healthy, nondiabetic children: results of the Diabetes Research in Children Network (DirecNet) accuracy study," *J Pediatr.* Jun. 2004;144(6):770–5.
Diabetes Research in Children Network (DirecNet) Study Group. "Accuracy of the GlucoWatch G2 Biographer and the continuous glucose monitoring system during hypoglycemia: experience of the Diabetes Research in Children Network," *Diabetes Care.* Mar. 2004; 27(3):722–6.
Sacks, ed., "Guidelines and Recommendations for Laboratory Analysis in the Diagnosis and Management of Diabetes Mellitus," (2002) in "Lab. Med. Practice Guidelines," vol. 13, pub. by Nat. Acad. Clin. Biochem.
Scheller et al., "Second Generation Biosensors," *Biosens Bioelectron.* 1991;6(3):245–53.
von Woedtke et al., "In Situ Calibration of Implanted Electrochemical Glucose Sensors," *Biomed Biochim Acta*, 48 (1989) 11/12, pp. 943–952.
Skoog & West, "Fundamentals of Analytical Chemistry," Holt, Rinehart & Winston, Inc. New York (1966), p. 55.
Armour et al., "Application of Chronic Intravascular Blood Glucose Sensor in Dogs," Diabetes, vol. 39, Dec. 1990, pp. 1519–1526.
McKean et al., "A Telemetry–Instrumentation System for Chronically Implanted Glucose and Oxygen Sensors," IEEE Transactions on Biomedical Engineering, vol. 35, No. 7, Jul. 1988.
Shichiri et al., "Wearable Artificial Endocrine Pancreas with Needle–Type Glucose Sensor," The Lancet, 1129–1131 (1982).
Shichiri et al. "In Vivo Characterisitics of Needle–Type Glucose Sensor—Measurements of Subcutaneous Glucose Concentrations in Human Volunteers," Horm. Metab. Res. Suppl., 20:17–20 (1988).
Shichiri et al., "Telemetry Glucose Monitoring Device With Needle–Type Glucose Sensor: A Useful Tool for Blood Glucose Monitoring in Diabetic Individuals," Diabetes Care, vol. 9, No. 3, May–Jun. 1986, pp. 298–301.

Shults et al., "A Telemetry–Instrumentation System for Monitoring Multiple Subcutaneously Implanted Glucose Sensors," IEEE Transactions on Biomedical Engineering, vol. 41, No. 10, Oct. 1994.

Thompson et al., "In Vivo Probes: Problems and Perspectives," Clinical Biochemistry, vol. 19, Oct. 1986, pp. 255–261.

Updike et al., Principles of Long–term Fully Implanted Sensors with Emphasis on Radiotelemetric Monitoring of Blood Glucose from inside a Subcutaneous Foreign Body Capsule (FBC), ed. Fraser, "Biosensors in the Body," 1997.

Velho et al., "Strategies for Calibrating a Subcutaneous Glucose Sensor," Biomed Biochim. Acta., 48 (1989) 11/12, 957–964.

Bindra et al., "Design and in Vitro Studies of a Needle–Type Glucose Sensor for Subcutaneous Monitoring," Anal. Chem., 1991, vol. 63, pp. 1692–1696.

Hamilton Needle Gauge Index, www.hamiltoncompany.com, undated.

Godsland et al., "Maximizing the Success Rate of Minimal Model Insulin Sensitivity Measurement in Humans: The Importance of Basal Glucose Levels," Clinical Science, (2001) 101, 1–9.

Shichiri et al., "Glycaemic Control in Pancreatectomized Dogs with a Wearable Artificial Endocrine Pancreas," Diabetologia (1983) 24: 179–184.

Shichiri et al., "Needle–Type Glucose Sensor for Wearable Artificial Endocrine Pancreas," Ch. 15, Implantable Sensors for Closed–Loop Prosthetic Systems, Futura Publishing, 1985, pp. 197–210.

Yang et al., "A comparison of physical properties and fuel cell performance fo Nafion and zirconium phosphate/Nafion composite membranes," Journal of Membrane Science 237 (2004) 145–161.

Salehi et al., "Telemetry–Instrumentation System for Long–Term Implantable Glucose and Oxygen Sensors," Analytical Letters, NY, US, vol. 29, No. 13, 1996, pp. 2289–2308.

Shichiri et al., "The Development of Wearable–Type Artificial Endocrine Pancreas and its Usefulness in Glycaemic Control of Human Diabetes Mellitus," Biomed. Biochim Acta 43(5), 561–568, 1984.

Brooks S. et al., "Development of an On–line Glucose Sensor for Fermentation Monitoring," (1987/88) Biosensors 3:45–56.

Pickup J. et al., "Implantable Glucose Sensors: Choosing the Appropriate Sensing Strategy," (1987/88) Biosensors 3:335–346.

Shaw GW et al., "In vitro testing of a simply constructed, highly stable glucose sensor suitable for implantation in diabetic patients," (1991) Biosensors & Bioelectronics 6:401–406.

Request of Ex Parte Reexamination of U.S. Patent No. 6,284,478 filed on behalf of DexCom, Inc., May 25, 2007, and all references cited therein.

Abel, P. U., et al., "Biosensors for In Vivo Glucose Measurement: Can We Cross the Experimental Stage", Biosensors and Bioelectronics, vol. 17, 2002, pp. 1059–1070.

Abruna, H. D., et al., "Rectifying Interfaces Using Two–Layer Films of Electrochemically Polymerized Vinylpyridine and Vinylbipyridine Complexes of Ruthenium and Iron on Electrodes", Journal of the American Chemical Society, vol. 103, No. 1, 1981, pp. 1–5.

Albery, W. J., et al., "Amperometric Enzyme Electrodes Part II: Conducting Salts as Electrode Materials for the Oxidation of Glucose Oxidase", Journal of ElectroAnalytical Chemistry, vol. 194, 1985, pp. 223–235.

Albery, W. J., et al., "Amperometric Enzyme Electrodes", Philosophical Transactions of The Royal Society of London, vol. 316, 1987, pp. 107–119.

Alcock, S. J., et al., "Continuous Analyte Monitoring to Aid Clinical Practice", IEEE Engineering in Medicine and Biology Magazine, 1994, pp. 319–325.

Anderson, L. B., et al., "Thin–Layer Electrochemistry: Steady–State Methods of Studying Rate Processes", Journal of ElectroAnalytical Chemistry, vol. 10, 1965, pp. 295–305.

Asberg, P., et al., "Hydrogels of a Conducting Conjugated Polymer as 3–D Enzyme Electrode", Biosensors & Bioelectronics, vol. 19, 2003, pp. 199–207.

Atanasov, P., et al., "Biosensor for Continuous Glucose Monitoring", Biotechnology and Bioengineering, vol. 43, 1994, pp. 262–266.

Atanasov, P., et al., "Implantation of a Refillable Glucose Monitoring–Telemetry Device", Biosensors & Bioelectronics, vol. 12, No. 7, 1997, pp. 669–680.

Aussedat, B., et al., "A User–Friendly Method for Calibrating a Subcutaneous Glucose Sensor–Based Hypoglycaemic Alarm", Biosensors & Bioelectronics, vol. 12, No. 11, 1997, pp. 1061–1071.

Baker, D. A., et al., "Dynamic Concentration Challenges for Biosensor Characterization", Biosensors & Bioelectronics, vol. 8, 1993, pp. 433–441.

Baker, D. A., et al., "Dynamic Delay and Maximal Dynamic Error in Continuous Biosensors", Analytical Chemistry, vol. 68, No. 8, 1996, pp. 1292–1297.

Bani Amer, M. M., "An Accurate Amperometric Glucose Sensor Based Glucometer with Eliminated Cross–Sensitivity", Journal of Medical Engineering & Technology, vol. 26, No. 5, 2002, pp. 208–213.

Bard, A. J., et al., Electrochemical Methods, 1980, pp. 173–175.

Bartlett, P. N., et al., "Covalent Binding of Electron Relays to Glucose Oxidase", Journal of the Chemical Society, Chemical Communications, 1987, pp. 1603–1604.

Bartlett, P. N., et al., "Modification of Glucose Oxidase by Tetrathiafulvalene", Journal of the Chemical Society, Chemical Communications, 1990, pp. 1135–1136.

Bartlett, P. N., et al., "Strategies for the Development of Amperometric Enzyme Electrodes", Biosensors, vol. 3, 1987/88, pp. 359–379.

Beach, R. D., et al., "Subminiature Implantable Potentiostat and Modified Commercial Telemetry Device for Remote Glucose Monitoring", IEEE Transactions on Instrumentation and Measurement, vol. 28, No. 6, 1999, pp. 1239–1245.

Beech, W. A., "AX.25 Link Access Protocol for Amateur packet Radio", Tucson Amateur Packet Radio Corporation, 1998, pp. 1–133.

Bennion, N., et al., "Alternate Site Glucose Testing: A Crossover Design", Diabetes Technology & Therapeutics, vol. 4, No. 1, 2002, pp. 25–33.

Bindra, D. S., et al., "Design and in Vitro Studies of a Needle–type Glucose Sensor for Subcutaneous Monitoring", Analytical Chemistry, vol. 63, No. 17, 1991, pp. 1692–1696.

Bindra, D. S., et al., "Pulsed Amperometric Detection of Glucose in Biological Fluids at a Surface–Modified Gold Electrode,", *Analytical Chemistry*, vol. 61, No. 72, 1989, pp. 2566–2570.

Bisenberger, M., et al., "A Triple–Step Potential Waveform at Enzyme Multisensors with Thick–Film Gold Electrodes for Detection of Glucose and Sucrose", *Sensors and Actuators B*, vol. 28, 1995, pp. 181–189.

Bland, J. M., et al., "A Note on the Use of the Intraclass Correlation Coefficient in the Evaluation of Agreement Between Two Methods of Measurement", *Computers in Biology and Medicine*, vol. 20, No. 5, 1990, pp. 337–340.

Bland, J. M., et al., "Statistical Methods for Assessing Agreement Between Two Methods of Clinical Measurement", *The Lancet*, 1986, pp. 307–310.

Blank, T. B., et al., "Clinical Results From a Non–Invasive Blood Glucose Monitor", *Optical Diagnostics and Sensing of Biological Fluids and Glucose and Cholesterol Monitoring II, Proceedings of SPIE*, vol. 4624, 2002, pp. 1–10.

Bobbioni–Harsch, E., et al., "Lifespan of Subcutaneous Glucose Sensors and Their Performances During Dynamic Glycaemia Changes in Rats", *Journal of Biomedical Engineering*, vol. 15, 1993, pp. 457–463.

Bode, B. W., "Clinical Utility of the Continuous Glucose Monitoring System", *Diabetes Technology & Therapeutics*, vol. 2, Sup. 1, 2000, pp. S35–S41.

Bode, B. W., et al., "Continuous Glucose Monitoring Used to Adjust Diabetes Therapy Improves Glycosylated Hemoglobin: A Pilot Study", *Diabetes Research and Clinical Practice*, vol. 46, 1999, pp. 183–190.

Bode, B. W., et al., "Using the Continuous Glucose Monitoring System to Improve the Management of Type I Diabetes", *Diabetes Technology & Therapeutics*, vol. 2, Sup. 1, 2000, pp. S43–S48.

Boedeker Plastics, Inc., "Polyethylene Specifications", *Web Page of Boedeker.com*, 2007, pp. 1–3.

Bolinder, J., et al., "Microdialysis Measurement of the Absolute Glucose Concentration in Subcutaneous Adipose Tissue Allowing Glucose Monitoring in Diabetic Patients", *Diabetologia*, vol. 35, 1992, pp. 1177–1180.

Bolinder, J., et al., "Self–Monitoring of Blood Glucose in Type I Diabetic Patients: Comparison with Continuous Microdialysis Measurements of Glucose in Subcutaneous Adipose Tissue During Ordinary Life Conditions", *Diabetes Care*, vol. 20, No. 1, 1997, pp. 64–70.

Bott, A. W., "A Comparison of Cyclic Voltammetry and Cyclic Staircase Voltammetry", *Current Separations*, vol. 16, No. 1, 1997, pp. 23–26.

Bott, A. W., "Electrochemical Methods for the Determination of Glucose", *Current Separations*, vol. 17, No. 1, 1998, pp. 25–31.

Bowman, L., et al., "The Packaging of Implantable Integrated Sensors", *IEEE Transactions on Biomedical Engineering*, vol. 33, No. 2, 1986, pp. 248–255.

Brandt, J., et al., "Covalent Attachment of Proteins to Polysaccharide Carriers by Means of Benzoquinone", *Biochimica et Biophysica Acta*, vol. 386, 1975, pp. 196–202.

Brauker, J., et al., "Sustained Expression of High Levels of Human Factor IX from Human Cells Implanted Within an Immunoisolation Device into Athymic Rodents", *Human Gene Therapy*, vol. 9, No. 6, 1998, pp. 879–888.

Bremer, T. M., et al., "Benchmark Data from the Literature for Evaluation of New Glucose Sensing Technologies", *Diabetes Technology & Therapeutics*, vol. 3, No. 3, 2001, pp. 409–418.

Bremer, T., et al., "Is Blood Glucose Predictable from Previous Values?", *Diabetes*, vol. 48, 1999, pp. 445–451.

Brownlee, M., et al., "A Glucose–Controlled Insulin–Delivery System: Semisynthetic Insulin Bound to Lectin", *Science*, vol. 206, 1979, 1190–1191.

Cai, Q., et al., "A Wireless, Remove Query Glucose Biosensor Based on a pH–Sensitive Polymer", *Analytical Chemistry*, vol. 76, No. 14, 2004, pp. 4038–4043.

Cass, A. E., et al., "Ferricinum Ion As An Electron Acceptor for Oxido–Reductases", *Journal of ElectroAnalytical Chemistry*, vol. 190, 1985, pp. 117–127.

Cass, A. E., et al., "Ferrocene–Medicated Enzyme Electrode for Amperometric Determination of Glucose", *Analytical Chemistry*, vol. 56, No. 4, 1984, pp. 667–671.

Castner, J. F., et al., "Mass Transport and Reaction Kinetic Parameters Determined Electrochemically for Immobilized Glucose Oxidase", *Biochemistry*, vol. 23, No. 10, 1984, 2203–2210.

Chen, J. C., et al., "A Comparison of MAC Protocols for Wireless Local Networks Based on battery Power Consumption", *IEEE*, 1998, pp. 150–157.

Chen, T., et al., "Defining the Period of Recovery of the Glucose Concentration After Its Local Pertubation by the Implantation of a Miniature Sensor", *Clinical Chemistry and Laboratory Medicine*, vol. 40, No. 8, 2002, pp. 486–489.

Chia, C. W., et al., "Glucose Sensors: Toward Closed Loop Insulin Delivery", *Endocrinology and Metabolism Clinics of North America*, vol. 33, 2004, pp. 175–195.

Choleau, C., et al., "Calibration of a Subcutaneous Amperometric Glucose Sensor Implanted for 7 Days in Diabetic Patients Part 2: Superiority of the One–Point Calibration Method", *Biosensors and Bioelectronics*, vol. 17, 2002, pp. 647–654.

Choleau, C., et al., "Calibration of a Subcutaneous Amperometric Glucose Sensor Part 1: Effect of Measurement Uncertainties on the Determination of Sensor Sensitivity and Background Current", *Biosensors and Bioelectronics*, vol. 17, 2002, pp. 641–646.

Claremont, D. J., et al., "Biosensors for Continuous In Vivo Glucose Monitoring", *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127–133.

Clark Jr., L. C., et al., "Electrode Systems for Continuous Monitoring in Cardiovascular Surgery", *Annals New York Academy of Sciences*, 1962, pp. 29–45.

Clark Jr., L. C., et al., "Long–term Stability of Electroenzymatic Glucose Sensors Implanted in Mice", *American Society of Artificial Internal Organs Transactions*, vol. XXXIV, 1988, pp. 259–265.

Clarke, W. L., et al., "Evaluating Clinical Accuracy of Systems for Self–Monitoring of Blood Glucose", *Diabetes Care*, vol. 10, No. 5, 1987, pp. 622–628.

Complaint, "*Abbott Diabetes Care, Inc. v. Dexcom, Inc.*", filed Aug. 11, 2005.

Complaint, Amended, "*Abbott Diabetes Care, Inc. v. Dexcom, Inc.*", filed Jun. 27, 2006.

Cox, D. J., et al., "Accuracy of Perceiving Blood Glucose in IDDM", *Diabetes Care,* vol. 8, No. 6, 1985, pp. 529–536.

Csoregi, E., et al., "Amperometric Microbiosensors for Detection of Hydrogen Peroxide and Glucose Based on Peroxidase–Modified Carbon Fibers", *Electroanalysis,* vol. 6, 1994, pp. 925–933.

Csoregi, E., et al., "Design and Optimization of a Selective Subcutaneously Implantable Glucose Electrode Based on 'Wired' Glucose Oxidase", *Analytical Chemistry,* vol. 67, No. 7, 1995, pp. 1240–1244.

Csoregi, E., et al., "Design, Characterization, and One–Point in Vivo Calibration of a Subcutaneously Implanted Glucose Electrode", *Analytical Chemistry,* vol. 66, No. 19, 1994, pp. 3131–3138.

Csoregi, E., et al., "On–Line Glucose Monitoring by Using Microdialysis Sampling and Amperometric Detection Based on 'Wired' Glucose Oxidase in Carbon Paste", *Mikrochimica Acta,* vol. 121, 1995, pp. 31–40.

D'Arrigo, G., et al., "Porous–Si Based Bio Reactors for Glucose Monitoring and Drugs Production", *Proceedings of SPIE: Microfluids, BioMEMS, and Medical Microsystems,* vol. 4982, 2003, pp. 178–184.

Davis, G., "Electrochemical Techniques for the Development of Amperometric Biosensors", *Biosensors,* vol. 1, 1985, pp. 161–178.

Degani, Y., et al., "Direct Electrical Communication Between Chemically Modified Enzymes and Metal Electrodes. I. Electron Transfer from Glucose Oxidase to Metal Electrodes via Electron Relays, Bound Covalently to the Enzyme", *The Journal of Physical Chemistry,* vol. 91, No. 6, 1987, pp. 1285–1289.

Degani, Y., et al., "Direct Electrical Communication Between Chemically Modified Enzymes and Metal Electrodes. 2. Methods for Bonding Electron–Transfer Relays to Glucose Oxidase and D–Amino–Acid Oxidase", *Journal of the American Chemical Society,* vol. 110, No. 8, 1988, pp. 2615–2620.

Degani, Y., et al., "Electrical Communication Between Redox Centers of Glucose Oxidase and Electrodes via Electrostatically and Covalently Bound Redox Polymers", *Journal of the American Chemical Society,* vol. 111, 1989, pp. 2357–2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society,* vol. 103, 1981, pp. 4727–4737.

Dicks, J. M., et al., "Ferrocene Modified Polypyrrole with Immobilised Glucose Oxidase and its Application in Amperometric Glucose Microbiosensors", *Annales de Biologie Clinique,* vol. 47, 1989, pp. 607–619.

Dixon, B. M., et al., "Characterization In Vitro and In Vivo of the Oxygen Dependence of an Enzyme/Polymer Biosensors for Monitoring Brain Glucose", *Journal of Neuroscience methods,* vol. 119, 2002, pp. 135–142.

Ellis, C. D., et al., "Selectivity and Directed Charge Transfer through an Electroactive Metallopolymer Film", *Journal of the American Chemical Society,* vol. 103, No. 25, 1981, pp. 7480–7483.

El–Sa'ad, L., et al., "Moisture Absorption by Epoxy Resins: The Reverse Thermal Effect", *Journal of Materials Science,* vol. 25, No. 8, 1990, pp. 3577–3582.

Engstrom, R. C., "Electrochemical Pretreatment of Glassy Carbon Electrodes", *Analytical Chemistry,* vol. 54, No. 13, 1982, pp. 2310–2314.

Engstrom, R. C., et al., "Characterization of Electrochemically Pretreated Glassy Carbon Electrodes", *Analytical Chemistry,* vol. 56, No. 2, 1984, pp. 136–141.

Ernst, H., et al., "Reliable Glucose Monitoring Through the Use of Microsystem Technology", *Analytical and Bioanalytical Chemistry,* vol. 373, 2002, pp. 758–761.

Fare, T. L., et al., "Functional Characterization of a Conducting Polymer–Based Immunoassay System", *Biosensors & Bioelectronics,* vol. 13, No. 3–4, 1998, pp. 459–470.

Feldman, B., et al., "A Continuous Glucose Sensor Based on Wired Enzyme™ Technology—Results from a 3–D Trial in Patients with Type 1 Diabetes", *Diabetes Technology & Therapeutics,* vol. 5, No. 5, 2003, pp. 769–779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet.*

Feldman, B., et al., "Electron Transfer Kinetics at Redox Polymer/Solution Interfaces Using Microelectrodes and Twin Electrode Thin Layer Cells", *Journal of ElectroAnalytical Chemistry,* vol. 194, 1985, pp. 63–81.

Fischer, H., et al., "Intramolecular Electron Transfer Medicated by 4,4'–Bypyridine and Related Bridging Groups", *Journal of the American Chemical Society,* vol. 98, No. 18, 1976, pp. 5512–5517.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1,* vol. 82, 1986, pp. 1259–1264.

Foulds, N. C., et al., "Immobilization of Glucose Oxidase in Ferrocene–Modified Pyrrole Polymers", *Analytical Chemistry,* vol. 60, No. 22, 1988, pp. 2473–2478.

Frew, J. E., et al., "Electron–Transfer Biosensors", *Philosophical Transactions of The Royal Society of London,* vol. 316, 1987, pp. 95–106.

Frohnauer, M. K., et al., "Graphical Human Insulin Time–Activity Profiles Using Standardized Definitions", *Diabetes Technology & Therapeutics,* vol. 3, No. 3, 2001, pp. 419–429.

Frost, M. C., et al., "Implantable Chemical Sensors for Real–Time Clinical Monitoring: Progress and Challenges", *Current Opinion in Chemical Biology,* vol. 6, 2002, pp. 633–641.

Garg, S. K., et al., "Correlation of Fingerstick Blood Glucose Measurements with GlucoWatch Biographer Glucose Results in Young Subjects with Type 1 Diabetes", *Diabetes Care,* vol. 22, No. 10, 1999, pp. 1708–1714.

Garg, S. K., et al., "Improved Glucose Excursions Using an Implantable Real–Time Continuous Glucose Sensor in Adults with Type 1 Diabetes", *Diabetes Care,* vol. 27, No. 3, 2004, pp. 734–738.

Geller, R. L., et al., "Use of an Immunoisolation Device for Cell Transplantation and Tumor Immunotherapy", *Annals of the New York Academy of Sciences,* vol. 831, 1997, pp. 438–451.

Gerritsen, M., "Problems Associated with Subcutaneously Implanted Glucose Sensors", *Diabetes Care,* vol. 23, No. 2, 2000, pp. 143–145.

Gerritsen, M., et al., "Influence of Inflammatory Cells and Serum on the Performance of Implantable Glucose Sensors", *Journal of Biomedical materials Research*, vol. 54, 2001, pp. 69–75.

Gerritsen, M., et al., "Performance of Subcutaneously Implanted glucose Sensors for Continuous Monitoring", *The Netherlands Journal of Medicine*, vol. 54, 1999, pp. 167–179.

Gilligan, B. J., et al., "Evaluation of a Subcutaneous Glucose Sensor Out to 3 Months in a Dog Model", *Diabetes Care*, vol. 17, No. 8, 1994, pp. 882–887.

Gilligan, B. J., et al., "Feasibility of Continuous Long–Term Glucose Monitoring from a Subcutaneous Glucose Sensor in Humans", *Diabetes Technology & Therapeutics*, vol. 6, No. 3, 2004, pp. 378–386.

Gorton, L., et al., "Selective Detection in Flow Analysis Based on the Combination of Immobilized Enzymes and Chemically Modified Electrodes", *Analytica Chimica Acta*, vol. 250, 1991, pp. 203–248.

Gough, D. A., et al., "Immobilized Glucose Oxidase in Implantable Glucose Sensor Technology", *Diabetes Technology & Therapeutics*, vol. 2, No. 3, 2000, pp. 377–380.

Grant, R., et al., *Grant & Hackh's Chemical Dictionary*, 1987, pp. 88, 89, 389, 390, 398.

Gregg, B. A., et al., "Cross–Linked Redox Gels Containing Glucose Oxidase for Amperometric Biosensor Applications", *Analytical Chemistry*, vol. 62, No. 3, 1990, pp. 258–263.

Gregg, B. A., et al., "Redox Polymer Films Containing Enzymes. 1. A Redox–Conducting Epoxy Cement: Synthesis, Characterization, and Electrocatalytic Oxidation of Hydroquinone", *Journal of Physical Chemistry*, vol. 95, No. 15, 1991, 5970–5975.

Gross, T. M., et al., "Efficacy and Reliability of the Continuous Glucose Monitoring System", *Diabetes Technology & Therapeutics*, vol. 2, Sup. 1, 2000, pp. S19–S26.

Gross, T. M., et al., "Performance Evaluation of the MiniMed© Continuous Glucose Monitoring System During Patient Home Use", *Diabetes Technology & Therapeutics*, vol. 2, No. 1, 2000, pp. 49–56.

Hale, P. D., et al., "A New Class of Amperometric Biosensor Incorporating a Polymeric Electron–Transfer Mediator", *Journal of the American Chemical Society*, vol. 111, No. 9, 1989, pp. 3482–3484.

Hall, S. B., et al., "Electrochemical Oxidation of Hydrogen Peroxide at Platinum Electrodes: Part 1: An Absorption–Controlled Mechanism", *Electrochimica Acta*, vol. 43, No. 5–6, 1998, pp. 579–588.

Hall, S. B., et al., "Electrochemical Oxidation of Hydrogen Peroxide at Platinum Electrodes: Part II: Effect of Potential", *Electrochimica Acta*, vol. 43, No. 14–15, 1998, pp. 2015–2024.

Hall, S. B., et al., "Electrochemical Oxidation of Hydrogen Peroxide at Platinum Electrodes: Part III: Effect of Temperature", *Electrochimica Acta*, vol. 44, 1999, pp. 2455–2462.

Hall, S. B., et al., "Electrochemical Oxidation of Hydrogen Peroxide at Platinum Electrodes: Part IV: Phosphate Buffer Dependence", *Electrochimica Acta*, vol. 44, 1999, pp. 4573–4582.

Hall, S. B., et al., "Electrochemical Oxidation of Hydrogen Peroxide at Platinum Electrodes: Part V: Inhibition By Chloride", *Electrochimica Acta*, vol. 45, 2000, pp. 3573–3579.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002–2007.

Hawkridge, F. M., et al., "Indirect Coulometric Titration of Biological Electron Transport Components", *Analytical Chemistry*, vol. 45, No. 7, 1973, pp. 1021–1027.

Heise, T., et al., "Hypoglycemia Warning Signal and Glucose Sensors: Requirements and Concepts", *Diabetes Technology & Therapeutics*, vol. 5, No. 4, 2003, pp. 563–571.

Heller, A., "Electrical Connection Enzyme Redox Centers to Electrodes", *Journal of Physical Chemistry*, vol. 96, No. 9, 1990, pp. 3579–3587.

Heller, A., "Electrical Wiring of Redox Enzymes", *Accounts of Chemical Research* vol. 23, No. 5, 1990, 128–134.

Heller, A., "Implanted Electrochemical Glucose Sensors for the Management of Diabetes", *Annual Review of Biomedical Engineering*, vol. 1, 1999, pp. 153–175.

Heller, A., "Plugging Metal Connectors into Enzymes", *Nature Biotechnology*, vol. 21, No. 6, 2003, pp. 631–632.

Heller, A., et al., "Amperometric Biosensors Based on Three–Dimensional Hydrogel–Forming Epoxy Networks", *Sensors and Actuators B*, vol. 13–14, 1993, pp. 180–183.

Hitchman, M. L., "Measurement of Dissolved Oxygen: Chapter 3: Principles of Voltammetry", *Chemical Analysis*, vol. 49, 1978, pp. 34–123.

Hrapovic, S., et al., "Picoamperometric Detection of Glucose at Ultrasmall Platinum–Based Biosensors: Preparation and Characterization", *Analytical Chemistry*, vol. 75, No. 14, 2003, pp. 3308–3315.

Huang, C. J., et al., "Electrochemical Generation of Oxygen", *Electrochemistry Research Laboratory*, 1972, pp. 1–115.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098–1101.

Ianniello, R. M., et al., "Immobilized Enzyme Chemically Modified Electrode as an Amperometric Sensor", *Analytical Chemistry*, vol. 53, No. 13, 1981, pp. 2090–2095.

Ikeda, T., et al., "Glucose Oxidase–Immobilized Benzoquinone–Carbon Paste Electrode as a Glucose Sensor", *Agricultural and Biological Chemistry*, vol. 49, No. 2, 1985, pp. 541–543.

Ikeda, T., et al., "Kinetics of Outer–Sphere Electron Transfers Between Metal Complexes in Solutions and Polymeric Films on Modified Electrodes", *Journal of the American Chemical Society*, vol. 103, No. 25, 1981, pp. 7422–7425.

Ishikawa, M., et al., "Initial Evaluation of a 290–µm Diameter Subcutaneous Glucose Sensor: Glucose Monitoring with a Biocompatible, Flexible–Wire, Enzyme–Based Amperometric Microsensor in Diabetic and Nondiabetic Humans", *Journal of Diabetes and Its Complications*, vol. 12, 1998, pp. 295–301.

Jablecki, M., et al., "Simulations of the Frequency Response of Implantable Glucose Sensors", *Analytical Chemistry*, vol. 72, No. 8, 2000, pp. 1853–1859.

Jaremko, J., et al., "Advances Toward the Implantable Artificial Pancreas for Treatment of Diabetes", *Diabetes Care*, vol. 21, No. 3, 1998, pp. 444–450.

Jensen, M. B., et al., "Fast Wave Forms for Pulsed Electrochemical Detection of Glucose by Incorporation of Reductive Desorption of Oxidation Products", *Analytical Chemistry*, vol. 69, No. 9, 1997, pp. 1776–1781.

Jeutter, D. C., "A Transcutaneous Implanted Battery Recharging and Biotelemeter Power Switching System", *IEEE Transactions on Biomedical Engineering*, vol. 29, No. 5, 1982, pp. 314–321.

Johnson, J. M., et al., "Potential–Dependent Enzymatic Activity in an Enzyme Thin–Layer Cell", *Analytical Chemistry*, vol. 54, No. 8, 1982, pp. 1377–1383.

Johnson, K. W., "Reproducible Electrodeposition of Biomolecules for the Fabrication of Miniature Electroenzymatic Biosensors", *Sensors and Actuators B*, vol. 5, 1991, pp. 85–89.

Johnson, P. C., "Peripheral Circulation", *John Wiley & Sons*, 1978, pp. 198.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355–368.

Josowicz, M., et al., "Electrochemical Pretreatment of Thin Film Platinum Electrodes", *Journal of the Electrochemical Society*, vol. 135, No. 1, 1988, pp. 112–115.

Jovanovic, L., "The Role of Continuous Glucose Monitoring in Gestational Diabetes Mellitus", *Diabetes Technology & Therapeutics*, vol. 2, Sup. 1, 2000, pp. S67–S71.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", *Diabetes Care*, vol. 24, No. 7, 2001, pp. 1303–1304.

Kang, S. K., et al., "In Vitro and Short–Term In Vivo Characteristics of a Kel–F Thin Film Modified Glucose Sensor", *Analytical Sciences*, vol. 19, 2003, pp. 1481–1486.

Kaplan, S. M., "Wiley Electrical and Electronics Engineering Dictionary", *IEEE Press*, 2004, pp. 141, 142, 548, 549.

Kargol, M., et al., "Studies on the Structural Properties of Porous Membranes: Measurement of Linear Dimensions of Solutes", *Biophysical Chemistry*, vol. 91, 2001, pp. 263–271.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617–3618.

Katakis, I., et al., "L–α–Glycerophosphate and L–Lactate Electrodes Based on the Electrochemical 'Wiring' of Oxidases", *Analytical Chemistry*, vol. 64, No. 9, 1992, pp. 1008–1013.

Kaufman, F. R., "Role of the Continuous Glucose Monitoring System in Pediatric Patients", *Diabetes Technology & Therapeutics*, vol. 2, Sup. 1, 1000, pp. S49–S52.

Kenausis, G., et al., "'Wiring' of Glucose Oxidase and Lactate Oxidase Within a Hydrogel Made with Poly(vinyl pyridine) complexed with $[Os(4,4'-dimethoxy-2,2'-bipyridine)_2Cl]^{+/2+}$", *Journal of the Chemical Society, Faraday Transactions*, vol. 92, No. 20, 1996, pp. 4131–4136.

Kerner, W., "Implantable Glucose Sensors: Present Status and Future Developments", *Experimental and Clinical Endocrinology & Diabetes*, vol. 109, Supplement 2, 2001, pp. S341–S346.

Koschinsky, T., et al., "New Approach to Technical and Clinical Evaluation of Devices for Self–Monitoring of Blood Glucose", *Diabetes Care*, vol. 11, No. 9, 1988, pp. 619–629.

Koschinsky, T., et al., "Sensors for Glucose Monitoring: Technical and Clinical Aspects" *Diabetes Metabolism Research and Reviews*, vol. 17, 2001, pp. 113–123.

Koudelka, M., et al., "In Vivo Behaviour of Hypodermically Implanted Microfabricated Glucose Sensors", *Biosensors & Bioelectronics*, vol. 6, 1991, pp. 31–36.

Kovatchev, B. P., et al., "Evaluating the Accuracy of Continuous Glucose–Monitoring Sensors", *Diabetes Care*, vol. 27, No. 8, 2004, pp. 1922–1928.

Kraver, K. L., et al., "A Mixed–Signal Sensor Interface Microinstrument", *Sensors and Actuators A*, vol. 91, 2001, pp. 266–277.

Krouwer, J. S., "Setting Performance Goals and Evaluating Total Analytical error for Diagnostic Assays", *Clinical Chemistry*, vol. 48, No. 6, 2002, pp. 919–927.

Kruger, D., et al., "Psychological Motivation and Patient Education: A Role for Continuous Glucose Monitoring", *Diabetes Technology & Therapeutics*, vol. 2, Sup. 1, 2000, pp. S93–S97.

Kulys, J., et al., "Mediatorless Peroxidase Electrode and Preparation of Bienzyme Sensors", *Bioelectrochemistry and Bioenergetics*, vol. 24, 1990, pp. 305–311.

Kurnik, R. T., et al., "Application of the Mixtures of Experts Algorithm for Signal Processing in a Noninvasive Glucose Monitoring System" *Sensors and Actuators B*, vol. 60, 1990, pp. 19–26.

Lacourse, W. R., et al., "Optimization of Waveforms for Pulsed Amperometric Detection of Carbohydrates Based on Pulsed Voltammetry", *Analytical Chemistry*, vol. 65, No. 1, 1993, pp. 50–55.

Lager, W., et al., "Implantable Electrocatalytic Glucose Sensor", *Hormone Metabolic Research*, vol. 26, 1994, pp. 526–530.

Lee, E., et al., "Effects of Pore Size, Void Volume, and Pore Connectivity on Tissue Responses to Porous Silicone Implants", *Transactions on the Twenty–Fifth Annual Meeting of the Society for Biomaterials*, vol. 22, 1999, pp. 171.

Lerner, H., et al., "An Implantable Electrochemical Glucose Sensor", *Annals of the New York Academy of Sciences*, vol. 428, 1984, pp. 263–278.

Leypoldt, J. K., et al., "Model of a Two–Substrate Enzyme Electrode for Glucose", *Analytical Chemistry*, vol. 56, No. 14, 1984, pp. 2896–2904.

Lindner, E., et al., "Flexible (Kapton–Based) Microsensor Arrays of High Stability for Cardiovascular Applications", *Journal of the Chemical Society, Faraday Transactions*, vol. 89, No. 2, 1993, pp. 361–367.

Liu, W., et al., "A Neuro–Stimulus Chip with Telemetry Unit for Retinal Prosthetic Device", *IEEE Journal of Solid–State Circuits*, vol. 35, No. 10, 2000, pp. 1487–1497.

Lortz, J., et al., "What is Bluetooth? We Explain The Newest Short–Range Connectivity Technology", *Smart Computing Learning Series, Wireless Computing*, vol. 8, Issue 5, 2002, pp. 72–74.

Luong, J. H. T., et al., "Solubilization of Multiwall Carbon Nanotubes by 3–Aminopropyltriehoxysilane Towards the Fabrication of Electrochemical Biosensors with Promoted Electron Transfer". *Electroanalysis*, vol. 16, No. 1–2, 2004, pp. 132–139.

Lynch, S. M., et al., "Estimation–Based Model Predictive Control of Blood Glucose in Type I Diabetics: A Simulation Study", *Proceedings of the IEEE 27th Annual Northeast Bioengineering Conference*, 2001, pp. 79–80.

Lynn, P. A., "Recursive Digital Filters for Biological Signals", *Medical and Biological Engineering*, vol. 9, 1971, pp. 37–43.

Maidan, R., et al., "Elimination of Electrooxidizable Interferant–Produced Currents in Amperometric Biosensors", *Analytical Chemistry*, vol. 64, No. 23, 1992, pp. 2889–2896.

Makale, M. T., et al., "Tissue Window Chamber System for Validation of Implanted Oxygen Sensors", *American Journal of Physiology: Heart and Circulatory Physiology*, vol. 284, 2003, pp. H2288–H2294.

Malin, S. F., et al., "Noninvasive Prediction of Glucose by Near–Infrared Diffuse Reflectance Spectoscopy", *Clinical Chemistry*, vol. 45, No. 9, 1999, pp. 1651–1658.

Mancy, K. H., et al., "A Galvanic Cell Oxygen Analyzer", *Journal of Electroanalytical Chemistry*, vol. 4, 1962, pp. 65–92.

Maran, A., et al., "Continuous Glucose Monitoring in Diabetic Patients", *Diabetes Care*, vol. 25, No. 2, 2002, pp. 347–352.

March, W. F., "Dealing with the Delay", *Diabetes Technology & Therapeutics*, vol. 4, No. 1, 2002, pp. 49–50.

Martin, R. F., "General Deming Regression for Estimating Systematic Bias and Its Confidence Interval in Method–Comparison Studies", *Clinical Chemistry*, vol. 46, No. 1, 2000, pp. 100–104.

Mastrototaro, J. J., "The MiniMed Continuous Glucose Monitoring System", *Diabetes Technology & Therapeutics*, vol. 2, Sup. 1, 2000, pp. S13–S18.

Mastrototaro, J. J., et al., "An Electroenzymatic Glucose Sensor Fabricated on a Flexible Substrate", *Sensors and Actuators B*, vol. 5, 1991, pp. 139–144.

Mastrototaro, J. J., et al., "Reproducibility of the Continuous Glucose Monitoring System Matches Previous Reports and the Intended Use of the Product" and "Response to Mastrototaro and Gross", *Diabetes Care*, vol. 26, No. 1, 2003, pp. 256–257.

McCartney, L. J., et al., "Near–Infrared Fluorescence Lifetime Assay for Serum Glucose Based on Allophycocyanin–Labeled Concanavalin A", *Analytical Biochemistry*, vol. 292, 2001, pp. 216–221.

McGarraugh, G., et al., "Glucose Measurements Using Blood Extracted from the Forearm and the Finger", *TheraSense, Inc.*, 16 pages.

McGarraugh, G., et al., "Physiological Influences on Off–Finger Glucose Testing", *Diabetes Technology & Therapeutics*, vol. 3, No. 3, 2001, pp. 367–376.

McGrath, M. J., et al., "The Use of Differential Measurements with a Glucose Biosensor for Interference Compensation During Glucose Determinations by Flow Injection Analysis", *Biosensors & Bioelectronics*, vol. 10, 1995, pp. 937–943.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25–29.

Memoli, A., et al., "A Comparison Between Different Immobilized Glucoseoxidase–Based Electrodes", *Journal of Pharmaceutical and Biomedical Analysis*, vol. 29, 2002, pp. 1045–1052.

Metzger, M., et al., "Reproducibility of Glucose Measurements Using the Glucose Sensor", *Diabetes Care*, vol. 25, No. 6, 2002, pp. 1185–1191.

Miller, K. M., et al., "Generation of IL1–like Activity in Response to Biomedical Polymer Implants: A Comparison of In Vitro and In Vivo Models", *Journal of Biomedical Materials Research*, vol. 23, 1989, pp. 1007–1026.

Miller, K. M., et al., "Human Monocyte/Macrophage Activation and Interleukin 1 Generation by Biomedical Polymers", *Journal of Biomedical Materials Research*, vol. 22, 1988, pp. 713–731.

Miller, K. M., et al., "In Vitro Stimulation of Fibroblast Activity by Factors Generated from Human Monocytes Activated by Biomedical Polymers", *Journal of Biomedical Materials Research*, vol. 23, 1989, pp. 911–930.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60–68.

Moatti–Sirat, D., et al., "Evaluating In Vitro and In Vivo the Interference of Ascorbate and Acetaminophen on Glucose Detection by a Needle–Type Glucose Sensor", *Biosensors & Bioelectronics*, vol. 7, 1992, pp. 345–352.

Moatti–Sirat, D., et al., "Reduction of Acetaminophen Interference in Glucose Sensors by a Composite Nafion Membrane: Demonstration in Rats and Man", *Diabetologia*, vol. 37, 1994, pp. 610–616.

Moatti–Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224–330.

Monsod, T. P., et al., "Do Sensor Glucose Levels Accurately Predict Plasma Glucose Concentrations During Hypoglycemia and Hyperinsulinemia?", *Diabetes Care*, vol. 25, No. 5, 2002, pp. 889–893.

Moussy, F., et al., "A Miniaturized Nafion–Based Glucose Sensor: In Vitro and In Vivo Evaluation in Dogs", *The International Journal of Artificial Organs*, vol. 17, No. 2, 1994, pp. 88–94.

Mowery, K. A., et al., "Preparation and Characterization of Hydrophobic Polymeric Films that are Thromboresistant via Nitric Oxide Release", *Biomaterials*, vol. 21, 2000, pp. 9–21.

Nagy, G., et al., "A New Type of Enzyme Electrode: The Ascorbic Acid Eliminator Electrode", *Life Sciences*, vol. 31, No. 23, 1982, pp. 2611–2616.

Nakamura, S., et al., "Effect of Periodate Oxidation on the Structure and Properties of Glucose Oxidase", *Biochimica et Biophysica Acta*, vol. 445, 1976, pp. 294–308.

Nam, Y. S., et al., "A Novel Fabrication Method of Macroporous Biodegradable Polymer Scaffolds Using Gas Foaming Salt as a Porogen Additive", *Journal of Biomedical Materials Research*, vol. 53, 2000, pp. 1–7.

Nappholz, T. A., "Programmers for Implants: A Need for Radical Change", *18th Annual International Conference of the IEEE Engineering in Medicine and Biology Society, Amsterdam*, 1996, pp. 1274–1275.

Narasimham, K., et al., "p–Benzoquinone Activation of Metal Oxide Electrodes for Attachment of Enzymes", *Enzyme and Microbial Technology*, vol. 7, 1985, pp. 283–286.

Neuburger, G. G., et al., "Pulsed Amperometric Detection of Carbohydrates at Gold Electrodes with a Two–Step Potential Waveform", *Analytical Chemistry*, vol. 59, No. 1, 1987, pp. 150–154.

Ohara, T. J., "Osmium Bipyridyl Redox Polymers Used in Enzyme Electrodes", *Platinum Metals Review*, vol. 39, No. 2, 1995, pp. 54–62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451–2457.

Ohara, T. J., et al., "Glucose Electrodes Based on Cross–Linked $[Os(bpy)_2Cl]^{+/2+}$ Complexed Poly(1–Vinylimidazole) Films", *Analytical Chemistry*, vol. 65, No. 23, 1993, pp. 3512–3517.

Okuda, J., et al., "Mutarotase Effect on Micro Determinations of D–Glucose and Its Anomers with β–D–Glucose Oxidase", *Analytical Biochemistry*, vol. 43, 1971, pp. 312–315.

Olievier, C. N., et al., "In Vivo Measurement of Carbon Dioxide Tension with a Miniature Electrodes", *Pflugers Archiv; European Journal of Physiology*, vol. 373, 1978, pp. 269–272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487–494.

Palleschi, G., et al., "A Study of Interferences in Glucose Measurements in Blood by Hydrogen Peroxide Based Glucose Probes", *Analytical Biochemistry*, vol. 159, 1986, pp. 114–121.

Palmisano, F., et al., "Simultaneous Monitoring of Glucose and Lactate by an Interference and Cross–Talk Free Dual Electrode Amperometric Biosensor Based on Electropolymerized Thin Films", *Biosensors & Bioelectronics*, vol. 15, 2000, pp. 531–539.

Pankratov, I., et al., "Sol–Gel Derived Renewable–Surface Biosensors", *Journal of ElectroAnalytical Chemistry*, vol. 393, 1995, pp. 35–41.

Panteleon, A. E., et al., "The Role of the Independent Variable to Glucose Sensor Calibration", *Diabetes Technology & Therapeutics*, vol. 5, No. 3, 2003, pp. 401–410.

Parker, R. S., et al., "A Model–Based Algorithm for Blood Glucose Control in Type I Diabetic Patients", *IEEE Transactions on Biomedical Engineering*, vol. 46, No. 2, 1999, pp. 148–157.

Patel, H., et al., "Amperometric Glucose Sensors Based on Ferrocene Containing Polymeric Electron Transfer Systems—A Preliminary Report", *Biosensors and Bioelectronics*, vol. 18, 2003, pp. 1073–1076.

Pathak, C., et al., "Rapid Photopolymerization of Immunoprotective Gels in Contact with Cells and Tissue", *Journal of the American Chemical Society*, vol. 114, No. 21, 1992, pp. 8311–8312.

Pichert, J. W., et al., "Issues for the Coming Age of Continuous Glucose Monitoring", *The Diabetic Educator*, vol. 26, No. 6, 2000, pp. 969–980.

Pickup, J. C., et al., "Responses and Calibration of Amperometric Glucose Sensors Implanted in the Subcutaneous Tissue of Man", *Acta Diabetologica*, vol. 30, 1993, pp. 143–148.

Pickup, J., "Developing Glucose Sensors for In Vivo Use", *Tibtech*, vol. 11, 1993, pp. 285–291.

Pickup, J., et al., "In Vivo Molecular Sensing in Diabetes Mellitus: An Implantable Glucose Sensor with Direct Electron Transfer", *Diabetologia*, vol. 32, 1989, pp. 213–217.

Pickup, J., et al., "Potentially–Implantable, Amperometric Glucose Sensors with Mediated Electron Transfer: Improving the Operating Stability", *Biosensors*, vol. 4, 1989, pp. 109–119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268–2272.

Pitzer, K. R., et al., "Detection of Hypoglycemia with the GlucoWatch Biographer", *Diabetes Care*, vol. 24, No. 5, 200, pp. 881–885.

Poirier, J. Y., et al., "Clinical and Statistical Evaluation of Self–Monitoring Blood Glucose Meters", *Diabetes Care*, vol. 21, No. 11, 1998, pp. 1919–1924.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetologia*, vol. 36, 1993, pp. 658–663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587–592.

Poitout, V., et al., "In Vitro and In Vivo Evaluation in Dogs of a Miniaturized Glucose Sensor", *ASAIO Transactions*, vol. 37, No. 3, 1991, pp. M298–M300.

Pollak, A., et al., "Enzyme Immobilization by Condensation Copolymerization into Cross–Linked Polyacrylamide Gels", *Journal of the American Chemical Society*, vol. 102, No. 20, 1980, pp. 6324–6336.

Postlethwaite, T. A., et al., "Interdigitated Array Electrode as an Alternative to the Rotated Ring–Disk Electrode for Determination of the Reaction Products of Dioxygen Reduction", *Analytical Chemistry*, vol. 68, No. 17, 1996, pp. 2951–2958.

Quinn, C. A. P., et al., "Biocompatible, Glucose–Permeable Hydrogel for In Situ Coating of Implantable Biosensors", *Biomaterials*, vol. 18, No. 24, 1997, pp. 1665–1670.

Quinn, C. P., et al., "Kinetics of Glucose Delivery to Subcutaneous Tissue in Rats Measured with 0.3–mm Amperometric Microsensors", *The American Physiological Society*, 1995, E155–E161.

Ratner, B. D., "Reducing Capsular Thickness and Enhancing Angeiogenesis Around Implant Drug Release Systems", *Journal of Controlled Release*, vol. 78, 2002, pp. 211–218.

Reach, G., "Which Threshold to Detect Hypoglycemia?", *Diabetes Care*, vol. 24, No. 5, 2001, pp. 803–804.

Reach, G., et al., "A Method of Evaluating In Vivo the Functional Characteristics of Glucose Sensors", *Biosensors 2*, 1986, pp. 211–220.

Reach, G., et al., "Can Continuous Glucose Monitoring Be Used for the Treatment of Diabetes?", *Analytical Chemistry*, vol. 64, No. 6, 1992, pp. 381–386.

Reach, G., et al., "Letters to the Editor: Re: Diabetes Technology & Therapeutics, 2000;2:49–56", *Diabetes Technology & Therapeutics*, vol. 3, No. 1, 2001, pp. 129–131.

Rebrin, K., et al., "Automated Feedback Control of Subcutaneous Glucose Concentration in Diabetic Dogs", *Diabetologia*, vol. 32, 1989, pp. 573–576.

Rebrin, K., et al., "Subcutaneous Glucose Predicts Plasma Glucose Independent of Insulin: Implications for Continuous Monitoring", *The American Physiological Society*, 1999, pp. E561–E571.

Rhodes, R. K., et al., "Prediction of Pocket–Portable and Implantable Glucose Enzyme Electrode Performance from Combined Species Permeability and Digital Simulation Analysis", *Analytical Chemistry*, vol. 66, No. 9, 1994, pp. 1520–1529.

Rinken, T., et al., "Calibration of Glucose Biosensors By Using Pre–Study State Kinetic Data", *Biosensors & Bioelectronics*, vol. 13, 1998, pp. 801–807.

Roe, J. N., et al., "Bloodless Glucose Measurements", *Critical Review in Therapeutic Drug Carrier Systems*, vol. 15, Issue 3, 1998, pp. 199–241.

Sakakida, M., et al., "Ferrocene–Mediated Needle–Type Glucose Sensor Covered with Newly Designed Biocompatible Membrane", *Sensors and Actuators B*, vol. 13–14, 1993, pp. 319–322.

Salehi, C., et al., "A Telemetry–Instrumentation System for Long–Term Implantable Glucose and Oxygen Sensors", *Analytical Letters*, vol. 29, No. 13, 1996, pp. 2289–2308.

Samuels, G. J., et al., "An Electrode–Supported Oxidation Catalyst Based on Ruthenium (IV). pH 'Encapsulation' in a Polymer Film", *Journal of the American Chemical Society*, vol. 103, No. 2, 1981, pp. 307–312.

Sansen, W., et al., "A Smart Sensor for the Voltammetric Measurement of Oxygen or Glucose Concentrations", *Sensors and Actuators B1*, 1990, pp. 298–302.

Sansen, W., et al., "Chapter 12: Glucose Sensor with Telemetry System", *Implantable Sensors for Closed–Loop Prosthetic Systems*, 1985, pp. 167–175.

Sasso, S. V., et al., "Electropolymerized 1,2–Diaminobenzene as a Means to Prevent Interferences and Fouling and to Stabilize Immobilized Enzyme in Electrochemical Biosensors", *Analytical Chemistry*, vol. 62, No. 11, 1990, pp. 1111–1117.

Scheller, F., et al., "Enzyme Electrodes and Their Application", *Philosophical Transactions of The Royal Society of London B*, vol. 316, 1987, pp. 85–94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97–109.

Schmidt, F. J., et al., "Glucose Concentration in Subcutaneous Extracellular Space", *Diabetes Care*, vol. 16, No. 5, 1993, pp. 695–700.

Schmidtke, D. W., et al., "Accuracy of the One–Point In Vivo Calibration of 'Wired' Glucose Oxidase Electrodes Implanted in Jugular Veins of Rats in Periods of Rapid Rise and Decline of the Glucose Concentration", *Analytical Chemistry*, vol. 70, No. 10, 1998, pp. 2149–2155.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294–299.

Schoemaker, M., et al., "The SCHM1 System: Subcutaneous Continuous Glucose Monitoring Based on Microdialysis Technique", *Diabetes Technology & Therapeutics*, vol. 5, No. 4, 2003, pp. 599–608.

Schwarz, M., et al., "Micro Implantable Visual Prostheses", *1st Annual International IEEE–EMBS Special Topic Conference on Microtechnologies in Medicine & Biology, Lyon, France*, 2000, pp. 461–465.

Selam, J. L., "Management of Diabetes with Glucose Sensors and Implantable Insulin Pumps: From the Dream of the 60s to the Realities of the 90s", *American Society for Artificial Internal Organs Journal*, 1997, pp. 137–142.

Service, R. F., "Can Sensors Make a Home in the Body?", *Science*, vol. 297, 2002, pp. 962–963.

Sieminski, A. L., et al., "Biomaterial–Microvasculature Interactions", *Biomaterials*, vol. 21, 2000, pp. 2233–2241.

Sittampalam, G., et al., "Surface–Modified Electrochemical Detector for Liquid Chromatography", *Analytical Chemistry*, vol. 55, No. 9, 1983, pp. 1608–1610.

Skyler, J. S., "The Economic Burden of Diabetes and the Benefits of Improved Glycemic Control: The Potential Role of a Continuous Glucose Monitoring System", *Diabetes Technology & Therapeutics*, vol. 2, Sup. 1, 2000, pp. S7–S12.

Soegijoko, S., et al., "External Artificial Pancreas: A New Control Unit Using Microprocessor", *Hormone and Metabolic Research Supplement Series*, vol. 12, 1982, pp. 165–169.

Sokolov, S., et al., "Metrological Opportunities of the Dynamic Mode of Operating an Enzyme Amperometric Biosensor", *Medical Engineering and Physics*, vol. 17, No. 6, 1995, pp. 471–476.

Sproule, B. A., et al., "Fuzzy Pharmacology: Theory and Applications", *Trends in Pharmacological Sciences*, vol. 23, No. 9, 2002, pp. 412–417.

Sprules, S. D., et al., "Evaluation of a New Disposable Screen–Printed Sensor Strip for the Measurement of NADH and its Modification to Produce a Lactate Biosensor Employing Microliter Volumes", *Electroanalysis*, vol. 8, No. 6, 1996, pp. 539–543.

Sriyudthsak, M., et al., "Enzyme–Epoxy Membrane Based Glucose Analyzing System and Medical Applications", *Biosensors & Bioelectronics*, vol. 11, No. 8, 1996, pp. 735–742.

Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27–31.

Sternberg, F., et al., "Calibration Problems of Subcutaneous Glucosensors when Applied 'In–Situ' in Man", *Hormone and Metabolic Research*, vol. 26, 1994, pp. 523–526.

Sternberg, F., et al., "Does Fall In Tissue Glucose Precede Fall In Blood Glucose?" *Diabetologia*, vol. 29, 1996, pp. 609–612.

Sternberg, R., et al., "Covalent Enzyme Coupling on Cellulose Acetate Membranes for Glucose Sensor Development", *Analytical Chemistry*, vol. 60, No. 24, 1988, pp. 2781–2786.

Sternberg, R., et al., "Study and Development of Multilayer Needle–Type Enzyme–Based Glucose Microsensors", *Biosensors*, vol. 4, 1988, pp. 27–40.

Street, J. O., et al., "A Note on Computing Robust Regression Estimates Via Interactively Reweighted Least Squares", *The American Statistician*, vol. 42, No. 2, 1988, pp. 152–154.

Suaning, G. J., et al., "CMOS Neurostimulation ASIC with 100 Channels, Scaleable Output, and Bidirectional Radio–Frequency Telemetry" *IEEE Transactions on Biomedical Engineering*, vol. 48, No. 2, 2001, pp. 248–260.

Suekane, M., "Immobilization of Glucose Isomerase", *Zettschrift fur Allgemeine Mikrobiologie,* vol. 22, No. 8, 1982, pp. 565–576.

Tajima, S., et al., "Simultaneous Determination of Glucose and 1,5–Anydroglucitol", *Chemical Abstracts,* vol. 111, No. 25, 1989, pp. 394.

Tamura, T., et al., "Preliminary Study of Continuous Glucose Monitoring with a Microdialysis Technique and a Null Method—a Numerical Analysis", *Frontiers Medical and Biological Engineering,* vol. 10, No. 2, 2000, pp. 147–156.

Tanenberg, R. J., et al., "Continuous Glucose Monitoring System: A New Approach to the Diagnosis of Diabetic Gastroparesis", *Diabetes Technology & Therapeutics,* vol. 2, Sup. 1, 2000, pp. S73–S80.

Tang, L., et al., "Fibrin(ogen) Mediates Acute Inflammatory Responses to Biomaterials", *Journal of Experimental Medicine,* vol. 178, 1993, pp. 2147–2156.

Tang, L., et al., "Inflammatory Responses to Biomaterials", *American Journal of Clinical Pathology,* vol. 103, No. 4, 1995, pp. 466–471.

Tang, L., et al., "Mast Cells Mediate Acute Inflammatory Responses to Implanted Biomaterials", *Proceedings of the National Academy of Sciences USA,* vol. 95, 1998, pp. 8841–8846.

Tang, L., et al., "Molecular Determinants of Acute Inflammatory Responses to Biomaterials", *Journal of Clinical Investigation,* vol. 97, No. 5, 1996, pp. 1329–1334.

Tang, Z., et al., "Data Transmission from an Implantable Biotelemeter by Load–Shift Keying Using Circuit Configuration Modulator", *IEEE Transactions on Biomedical Engineering,* vol. 47, No. 5, 1995, pp. 524–528.

Tarasevich, M. R., "Bioelectrocatalysis", *Comprehensive Treatise of Electrochemistry,* vol. 10, 1985, pp. 231–295.

Tatsuma, T., et al., "Enzyme Monolayer– and Bilayer–Modified Tin Oxide Electrodes for the Determination of Hydrogen Peroxide and Glucose", *Analytical Chemistry,* vol. 61, No. 21, 1989, pp. 2352–2355.

Taylor, C., et al., "'Wiring' of Glucose Oxidase Within a Hydrogel Made with Polyvinyl Imidazole Complexed with $[(Os–4,4'–dimethoxy–2,2'–bipyridine)Cl]^{+/2+}$", *Journal of ElectroAnalytical Chemistry,* vol. 396, 1995, pp. 511–515.

Thome–Duret, V., et al., "Continuous Glucose Monitoring in the Free–Moving Rat", *Metabolism,* vol. 47, No. 7, 1998, pp. 799–803.

Thome–Duret, V., et al., "Modification of the Sensitivity of Glucose Sensor Implanted into Subcutaneous Tissue", *Diabetes & Metabolism,* vol. 22, No. 3, 1996, pp. 174–178.

Tibell, A., et al., "Survival of Macroencapsulated Allogeneic Parathyroid Tissue One Year After Transplantation in Nonimmunosuppressed Humans", *Cell Transplantation,* vol. 10, No. 7, 2001, pp. 591–599.

Tierney, M. J., "The GlucoWatch© Biographer: A Frequent, Automatic and Noninvasive Glucose Monitor", *Annals of Medicine,* vol. 32, 2000, pp. 632–641.

Tierney, M. J., et al., "Effect of Acetaminophen on the Accuracy of Glucose Measurements Obtained with the GlucoWatch Biographer", *Diabetes Technology & Therapeutics,* vol. 2, No. 2, 2000, pp. 199–207.

Tilbury, J. B., et al., "Receiver Operating Characteristic Analysis for Intelligent Medical Systems—A New Approach for Finding Confidence Intervals", *IEEE Transactions on Biomedical Engineering,* vol. 47, No. 7, 2000, pp. 952–963.

Trajanoski, Z., et al., "Neural Predictive Controller for Insulin Delivery Using the Subcutaneous Route", *IEEE Transactions on Biomedical Engineering,* vol. 45, No. 9, 1998, pp. 1122–1134.

Trecroci, D., "A Glimpse Into the Future: Continuous Monitoring of Glucose with a Microfiber", *Diabetes Interview,* 2002, pp. 42–43.

Trojanowicz, M., et al., "Enzyme Entrapped Polypyrrole Modified Electrode for Flow–Injection Determination of Glucose", *Biosensors & Bioelectronics,* vol. 5, 1990, pp. 149–156.

Turner, A., et al., "Diabetes Mellitus: Biosensors for Research and Management", *Biosensors,* vol. 1, 1985, pp. 85–115.

Turner, R. F., et al., "A Biocompatible Enzyme Electrode for Continuous in vivo Glucose Monitoring in Whole Blood", *Sensors and Actuators B,* vol. 1, 1990, pp. 561–564.

Tuzhi, P., et al., "Constant Potential Pretreatment of Carbon Fiber Electrodes for In Vivo Electrochemistry", *Analytical Letters,* vol. 24, No. 6, 1991, pp. 935–945.

U.S. Department of Health and Human Services, "Off–The–Shelf–Software Use in Medical Devices", *Guidance for Industry, FDA Reviewers and Compliance on,* 1999, pp. 1–26.

Umana, M., "Protein–Modified Electrochemically Active Biomaterial Surface", *U.S. Army Research Office, Analytical and Chemical Sciences Research Triangle Institute,* 1988, pp. 1–9.

Updike, S. J., et al., "A Subcutaneous Glucose Sensor with Improved Longevity, Dynamic Range, and Stability of Calibration", *Diabetes Care,* vol. 23, No. 2, 2000, pp. 208–214.

Updike, S. J., et al., "Continuous Glucose Monitor Based on an Immobilized Enzyme Electrode Detector", *The Journal of Laboratory and Clinical Medicine,* vol. 93, No. 4, 1979, pp. 518–527.

Updike, S. J., et al., "Enzymatic Glucose Sensors: Improved Long–Term Performance In Vitro and In Vivo", *American Society for Artificial Internal Organs Journal,* 1994, pp. 157–163.

Updike, S. J., et al., "Implanting the Glucose Enzyme Electrode: Problems, Progress, and Alternative Solutions", *Diabetes Care,* vol. 5, No. 3, 1982, pp. 207–212.

Updike, S. J., et al., "The Enzyme Electrode", *Nature,* vol. 214, 1967, pp. 986–988.

Urban, G., et al., "Miniaturized Thin–Film Biosensors Using Covalently Immobilized Glucose Oxidase", *Biosensors & Bioelectronics,* vol. 6, 1991, pp. 555–562.

Valdes, T. I., et al., "In Vitro and In Vivo Degradation of Glucose Oxidase Enzyme Used for an Implantable Glucose Biosensor", *Diabetes Technology & Therapeutics,* vol. 2, No. 3, 2000, pp. 367–376.

Velho, G., et al., "In Vitro and In Vivo Stability of Electrode Potentials in Needle–Type Glucose Sensors", *Diabetes,* vol. 38, No. 2, 1989, pp. 164–171.

Von Woedtke, T., et al., "In Situ Calibration of Implanted Electrochemical Glucose Sensors", *Biomedica Biochimica Acta,* vol. 48, 1989, pp. 943–952.

Vreeke, M. S., et al., "Hydrogen Peroxide Electrodes Based on Electrical Connection of Redox Centers of Various Peroxidases to Electrodes through a Three–Dimensional Electron–Relaying Polymer Network", *Diagnostic Biosensors Polymers,* Chapter 15, 1993, pp. 180–193.

Vreeke, M., et al., "Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network", *Analytical Chemistry*, vol. 64, No. 24, 1992, pp. 3084–3090.

Wade Jr., L. G., "Chapter 17: Reactions of Aromtic Compounds", *Organic Chemistry, Sixth Edition,* 2006, pp. 762–763.

Wagner, J. G., et al., "Continuous Amperometric Monitoring of Glucose in a Brittle Diabetic Chimpanzee with a Miniature Subcutaneous Electrode", *Proceedings of the National Academy of Sciences USA,* 1998, pp. 6379–6382.

Wang, D. L., et al., "Miniaturized Flexible Amperometric Lactate Probe", *Analytical Chemistry*, vol. 65, No. 8, 1993, pp. 1069–1973.

Wang, J., et al., "Activation of Glassy Carbon Electrodes by Alternating Current Electrochemical Treatment", *Analytica Chimica Acta*, vol. 167, 1985, pp. 325–334.

Wang, J., et al., "Amperometric Biosensing of Organic Peroxides with Peroxidase–Modified Electrodes", *Analytica Chimica Acta*, vol. 254, 1991, pp. 81–88.

Wang, J., et al., "Highly Selective Membrane–Free Mediator–Free Glucose Biosensor", *Analytical Chemistry*, vol. 66, No. 21, 1994, pp. 3600–3606.

Wang, J., et al., "Screen–Printable Sol–Gel Enzyme–Containing Carbon Inks", *Analytical Chemistry*, vol. 68, No. 15, 1996, pp. 2705–2708.

Wang, J., et al., "Sol–Gel Derived Metal–Dispersed Carbon Composite Amperometric Biosensors", *Electroanalysis*, vol. 9, No. 1, 1997, pp. 52–55.

Wang, X., et al., "Improved Ruggedness for Membrane–Based Amperometric Sensors Using a Pulsed Amperometric Method", *Analytical Chemistry*, vol. 69, No. 21, 1997, pp. 4482–4489.

Ward, W. K., et al., "A New Amperometric Glucose Microsensor: In Vitro and Short–Term In Vivo Evaluation", *Biosensors & Bioelectronics*, vol. 17, 2002, pp. 181–189.

Ward, W. K., et al., "Assessment of Chronically Implanted Subcutaneous Glucose Sensors in Dogs: The Effect of Surrounding Fluid Masses", *American Society for Artificial Internal Organs Journal,* 1999, pp. 555–561.

Ward, W. K., et al., "Rise in Background Current Over Time in a Subcutaneous Glucose Sensor in the Rabbit: Relevance to Calibration and Accuracy", *Biosensors & Bioelectronics*, vol. 15, 2000, pp. 53–61.

Ward, W. K., et al., "Understanding Spontaneous Output Fluctuations of an Amperometric Glucose Sensor: Effect of Inhalation Anesthesia and Use of a Nonenzyme Containing Electrode", *American Society for Artificial Internal Organs Journal,* 2000, pp. 540–546.

Wientjes, K. J. C., *Development of a Glucose Sensor for Diabetic Patients,* 2000, pp. vii–xiii.

Wilkins, E., et al., "Glucose Monitoring: State of the Art and Future Possibilities", *Medical Engineering and Physics*, vol. 18, No. 4, 1995, pp. 273–288.

Wilkins, E., et al., "Integrated Implantable Device for Long–Term Glucose Monitoring", *Biosensors & Bioelectronics*, vol. 10, 1995, pp. 485–494.

Williams, D. L., et al., "Electrochemical–Enzymatic Analysis of Blood Glucose and Lactate", *Analytical Chemistry*, vol. 42, No. 1, 1970, pp. 118–121.

Wilson, G. S., et al., "Enzyme–Based Biosensors for In Vivo Measurements", *Chemical Reviews*, vol. 100, No. 7, 2000, pp. 2693–2704.

Wilson, G. S., et al., "Progress Toward the Development of an Implantable Sensor for Glucose", *Clinical Chemistry*, vol. 38, No. 9, 1992, pp. 1613–1617.

Wood, W. D., et al., "Hermetic Sealing with Epoxy", *Mechanical Engineering,* 1990, pp. 46–48.

Wu, H., et al., "In Situ electrochemical Oxygen Generation with an Immunoisolation Device", *Annals of the new York Academy of Sciences, vol. 875,* 1999, pp. 105–125.

Yabuki, S., et al., "Electro–Conductive Enzyme Membrane", *Journal of the Chemical Society, Chemical Communications,* 1989, pp. 945–946.

Yang, L., et al., "Determinaton of Oxidase Enzyme Substrates Using Cross–Flow Thin–Layer Amperometry", *Electroanalysis*, vol. 8, No. 8–9, 1996, pp. 716–721.

Yang, Q., et al., "Development of Needle–Type Glucose Sensor with High Selectivity", *Sensors and Actuators B*, vol. 46, 1998, pp. 249–256.

Yao, S. J., et al., "The Interference of Ascorbate and Urea in Low–Potential Electrochemical Glucose Sensing", *Proceedings of the Twelfth Annual International Conference of the IEEE Engineering in Medicine and Biology Society*, vol. 12, Part 2, 1990, pp. 487–489.

Yao, T., "A Chemically–Modified Enzyme Membrane Electrode as an Amperometric Glucose Sensor", *Analytica Chimica Acta*, vol. 148, 1983, pp. 27–33.

Ye, L., et al., "High Current Density 'Wired' Quinoprotein Glucose Dehydrogenase Electrode", *Analytical Chemistry*, vol. 65, No. 3, 1993, pp. 238–241.

Yildiz, A., et al., "Evaluation of an Improved Thin–Layer Electrode", *Analytical Chemistry*, vol. 40, No. 7, 1968, pp. 1018–1024.

Zamzow, K., et al., "New Wearable Continuous Blood Glucose Monitor (BGM) and Artificial Pancreas (AP)", *Diabetes*, vol. 39, 1990, pp. 5A–20.

Zavalkoff, S. R., et al., "Evaluation of Conventional Blood Glucose Monitoring as an Indicator of Integrated Glucose Values Using a Continuous Subcutaneous Sensor", *Diabetes Care*, vol. 25, No. 9, 2002, pp. 1603–1606.

Zhang, Y., et al., "Application of Cell Culture Toxicity Tests to the Development of Implantable Biosensors", *Biosensors & Bioelectronics*, vol. 6, 1991, pp. 653–661.

Zhang, Y., et al., "Elimination of the Acetaminophen Interference in an Implantable Glucose Sensor", *Analytical Chemistry*, vol. 66, No. 7, 1994, pp. 1183–1188.

Zhu, J., et al., "Planar Amperometric Glucose Sensor Based on Glucose Oxidase Immobilized by Chitosan Film on Prussian Blue Layer", *Sensors*, vol. 2, 2002, pp. 127–136.

Brooks et al., Biosensors (1987/88) 3:45–56.

Cass et al., Anal. Chem. (1984) 56:667–671.

Pickup et al., Biosensors (1987/88) 3:335–346.

Pickup et al., Diabetologia (1989) 32:213–217.

Pishko et al., Anal. Chem. (1991) 63:2268–2272.

Sakakida et al., Sensors and Actuators B (1993) 13–14:319–322.

Shaw et al., Biosensors & Bioelectronics (1991) 6:401–406.

Shichiri et al., Diab. Nutr. Metab. (1989) 2:309–313.

Sternberg et al., Biosensors (1988) 4:27–40.

Turner and Pickup, Biosensors (1985) 85–115.

Wilson et al., Clin. Chem. (1992) 38/9:1613–1617.

\* cited by examiner

United States Patent

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5–8, 38, 45 and 46 are cancelled.

Claims 1, 4, 9, 39–44, 47, 52, 64 and 69 are determined to be patentable as amended.

Claims 2, 3, 10–37, 48–51, 53–63, 65–68 and 70–74, dependent on an amended claim, are determined to be patentable.

New claims 75–101 are added and determined to be patentable.

1. An electrochemical sensor *for measuring an analyte in an animal* comprising:
   one or more non-corroding metal or carbon electrodes *adapted for at least partial subcutaneous implantation in an animal*;
   a sensing layer comprising an enzyme coupled to each electrode; and
   a biocompatible layer comprising a biocompatible hydrogel chemically bound to the sensing layer of each electrode,
   *wherein all subcutaneous layers overlying each electrode permits at least some analyte diffusion therethrough, and*
   *wherein the electrochemical sensor is configured to have an in vivo glucose sensitivity of from about 10 pA/mg/dL to about 250 pA/mg/dL which does not change by more than about ±5% for 72 hours of operation at 37° C.*

4. An analyte measurement system comprising: [an]
   *two or more* electrochemical [sensor] *sensors, each sensor* including two or more non-corroding metal or carbon electrodes *including a working electrode*, each *working* electrode adapted for subcutaneous implantation in an animal, and a non-leachable analyte-responsive enzyme disposed on each of the *working* electrodes; and
   a device for comparing signals generated at the two or more *working* electrodes.

9. An electrochemical sensor for measuring an analyte in an animal, comprising:
   one or more analyte responsive electrodes, at least one of said analyte-responsive electrode adapted for subcutaneous implantation in an animal, each of the analyte responsive electrodes comprising
   a non-corroding metal or carbon electrode, and
   a sensing layer covering at least a portion of each non-corroding metal or carbon electrode, comprising a redox enzyme and a redox compound,
   wherein the redox enzyme and redox compound are non-leachable by fluids in the body of the animal at a pH of between about 6.5 and about 7.8; *and*
   *one or more alarms, each alarm responsive to a signal generated by the one or more non-corroding metal or carbon electrodes corresponding to an analyte level,*
   *wherein at least one of the alarms is configured to activate if a signal generated at the electrode indicates impending hypoglycemia or impending hyperglycemia.*

39. The electrochemical sensor of claim [38]*9*, wherein one or more of the alarms is configured to activate if a signal generated at one of the electrodes coupled to the alarm is outside a predetermined range.

40. The electrochemical sensor of claim [38]*9*, wherein at least one of the alarms is configured to activate if a signal generated at the electrode indicates a blood glucose concentration above a predetermined concentration.

41. The electrochemical sensor of claim [38]*9*, wherein at least one of the alarms is configured to activate if a signal generated at the electrode indicates an increase in glucose concentration with time over a predetermined rate.

42. The electrochemical sensor of claim [38]*9*, wherein at least one of the alarms is configured to activate if a signal generated at the electrode indicates a changing glucose concentration that accelerates over time above a predetermined acceleration.

43. The electrochemical sensor of claim [38]*9*, wherein at least one of the alarms is configured to activate if a signal generated at the electrode indicates a blood glucose concentration below a predetermined concentration.

44. The electrochemical sensor of claim [38]*9*, wherein at least one of the alarms is configured to activate if a signal generated at the electrode indicates a decrease in glucose concentration with time over a predetermined rate.

47. The electrochemical sensor of claim [38]*9*, wherein the sensor of the system comprises two or more non-corroding metal or carbon electrodes and one or more alarms each coupled to two or more of the non-corroding metal or carbon electrodes.

52. A method of calibrating an electrochemical sensor *at least partially implanted in an animal*, comprising the steps of:
   withdrawing a single calibration sample from an animal;
   assaying an analyte concentration of the single calibration sample; [and]
   correlating the assayed analyte concentration to a signal generated by one or more implanted working electrodes of an electrochemical sensor *to calibrate the electrochemical sensor*, each working electrode having an analyte-responsive enzyme disposed thereon; *and*
   *allowing a predetermined period of time after implantation of the sensor before the signal generated by the sensor is used as an indicator of analyte concentration to the user.*

64. A method for the analysis of a bioanalyte, comprising:
   providing an analyte measurement system comprising two or more subcutaneously implantable *working* electrodes, *the system configured to have a glucose sensivity of from about 10 pA/mg/dL to about 250 pA/mg/dL*;
   subcutaneously implanting two or more *working* electrodes in the body of an animal;
   obtaining readings from each of the electrodes at substantially one point in time;
   comparing two or more of the readings from the electrodes; and accepting those readings which do not vary by more than a predetermined degree.

69. The method of claim 64, wherein the sensor is capable of calibration by a method of calibrating an electrochemical sensor, comprising the steps of:

withdrawing a single calibration sample from an animal;

assaying an analyte concentration of the single calibration sample; and correlating the assayed analyte concentration to a signal generated by one or more implanted working electrodes of [an] *the* electrochemical sensor *implanted in the animal to calibrate the sensor*, each working electrode having an analyte-responsive enzyme disposed thereon.

75. The electrochemical sensor of claim 1, further comprising one or more alarms, each alarm responsive to a signal generated by the one or more non-corroding metal or carbon electrodes corresponding to an analyte level.

76. The electrochemical sensor of claim 75, wherein one or more of the alarms is configured to activate if a signal generated at one of the electrodes coupled to the alarm is outside a predetermined range.

77. The electrochemical sensor of claim 75, wherein at least one of the alarms is configured to activate if a signal generated at the electrode indicates a glucose concentration above a predetermined concentration.

78. The electrochemical sensor of claim 75, wherein at least one of the alarms is configured to activate if a signal generated at the electrode indicates an increase in glucose concentration with time over a predetermined rate.

79. The electrochemical sensor of claim 75, wherein at least one of the alarms is configured to activate if a signal generated at the electrode indicates a changing glucose concentration that accelerates over time above a predetermined acceleration.

80. The electrochemical sensor of claim 75, wherein at least one of the alarms is configured to activate if a signal generated at the electrode indicates a glucose concentration below a predetermined concentration.

81. The electrochemical sensor of claim 75, wherein at least one of the alarms is configured to activate if a signal generated at the electrode indicates a decrease in glucose concentration with time over a predetermined rate.

82. The electrochemical sensor of claim 1, wherein the sensing layer is formed in situ on the electrode.

83. The electrochemical sensor of claim 1, wherein, wherein the electrochemical sensor is for calibration using a single calibration sample.

84. The electrochemical sensor of claim 1, wherein the electrochemical sensor comprises a wire.

85. The electrochemical sensor of claim 1, wherein the analyte responsive electrode defines a recessed portion.

86. The electrochemical sensor of claim 85, wherein the sensing layer is at least partially disposed in the recessed portion.

87. The analyte measurement system of claim 4, further comprising one or more alarms, each alarm responsive to a signal generated by the one or more non-corroding metal or carbon electrodes corresponding to an analyte level.

88. The electrochemical sensor of claim 87, wherein one or more of the alarms is configured to activate if a signal generated at one of the electrodes coupled to the alarm is outside a predetermined range.

89. The analyte measurement system of claim 4, wherein the electrochemical sensor is for calibration using a single calibration sample.

90. The analyte measurement system of claim 4, wherein the electrochemical sensor comprise a wire.

91. The analyte measurement system of claim 4, wherein at least one of the non-corroding metal or carbon electrode defines a recessed portion.

92. The electrochemical sensor of claim 91, wherein the non-leachable analyte-responsive enzyme is at least partially disposed in the recessed portion.

93. The electrochemical sensor of claim 9, wherein the electrochemical sensor comprises a wire.

94. The electrochemical sensor of claim 9, wherein the analyte responsive electrode defines a recessed portion.

95. The electrochemical sensor of claim 94, wherein the sensing layer is at least partially disposed in the recessed portion.

96. The method of claim 52, wherein the sensor is an electrochemical sensor for measuring an analyte in an animal, comprising: one or more analyte responsive electrodes, at least one of said analyte-responsive electrodes adapted for subcutaneous implantation in an animal, each of the analyte responsive electrodes comprising a non-corroding metal or carbon electrode, and a sensing layer, the sensing layer formed in situ on the electrode.

97. The method of claim 52, wherein the sensor is an electrochemical sensor for measuring an analyte in an animal, the electrochemical sensor comprising a wire.

98. An electrochemical sensor for measuring an analyte in an animal comprising:

one or more non-corroding metal or carbon electrodes adapted for at least partial subcutaneous implantation in an animal;

a sensing layer comprising an enzyme coupled to each electrode; and a substantially homogeneous biocompatible layer comprising a bicompatible hydrogel chemically bound to the sensing layer of each electrode, wherein all subcutaneous layers overlying each electrode comprise material which permits at least some analyte diffusion therethrough.

99. An electrochemical sensor for measuring an analyte in an animal comprising:

one or more non-corroding metal or carbon electrodes adapted for at least partial subcutaneous implantation in an animal having a width of no more than about 0.25 mm;

a sensing layer comprising an enzyme coupled to each electrode; and a biocompatible layer comprising a biocompatible hydrogel chemically bound to the sensing layer of each electrode, wherein all subcutaneous layers overlying each electrode comprise material which permits at least some analyte diffusion therethrough.

100. An electrochemical sensor for measuring an analyte in an animal comprising:

one or more non-corroding metal or carbon electrodes adapted for at least partial subcutaneous implantation in an animal;

a sensing layer comprising an enzyme coupled to each electrode; and a biocompatible layer comprising a biocompatible hydrogel chemically bound to the sensing layer of each electrode, wherein all subcutaneous layers overlying each electrode comprise material which permits at least some analyte diffusion therethrough; and wherein the portion of the sensor that is adapted for subcutaneous implantation has a width of no more than about 0.29 mm.

101. An analyte measurement system comprising:

an electrochemical sensor including two or more non-corroding metal or carbon working electrodes, each working electrode adapted for subcutaneous implantation in an animal, and a non-leachable analyte-responsive enzyme disposed on each of the working electrodes;

a device for comparing signals generated at the two or more working electrodes, wherein the system is configured to have a glucose sensitivity of from about 10 pA/mg/dL to about 250 pA/mg/dL.

* * * * *

(12) EX PARTE REEXAMINATION CERTIFICATE (9648th)
United States Patent
Heller et al.

(10) Number: US 6,284,478 C2
(45) Certificate Issued: May 13, 2013

(54) SUBCUTANEOUS GLUCOSE ELECTRODE

(75) Inventors: Adam Heller, Austin, TX (US); Michael V. Pishko, Austin, TX (US)

(73) Assignee: Therasense, Inc., Alameda, CA (US)

Reexamination Request:
No. 90/009,472, Sep. 3, 2009

Reexamination Certificate for:
Patent No.: 6,284,478
Issued: Sep. 4, 2001
Appl. No.: 08/767,110
Filed: Dec. 4, 1996

Reexamination Certificate C1 6,284,478 issued Sep. 29, 2009

Certificate of Correction issued Feb. 11, 2003

Related U.S. Application Data

(63) Continuation of application No. 08/299,526, filed on Sep. 1, 1994, now Pat. No. 5,593,852.

(51) Int. Cl.
*C12Q 1/54* (2006.01)
*C12Q 1/26* (2006.01)
*C12Q 1/28* (2006.01)
*C12Q 1/006* (2006.01)
*G01N 33/66* (2006.01)

(52) U.S. Cl.
USPC ... 435/14; 435/4; 435/25; 435/28; 435/288.5; 435/817; 436/63; 436/149; 204/403.1; 204/403.13; 204/403.14; 204/403.15; 205/778; 600/345; 600/347

(58) Field of Classification Search
None
See application file for complete search history.

(56) References Cited

To view the complete listing of prior art documents cited during the proceeding for Reexamination Control Number 90/009,472, please refer to the USPTO's public Patent Application Information Retrieval (PAIR) system under the Display References tab.

*Primary Examiner* — Dwayne Jones

(57) ABSTRACT

A small diameter flexible electrode designed for subcutaneous in vivo amperometric monitoring of glucose is described. The electrode is designed to allow "one-point" in vivo calibration, i.e., to have zero output current at zero glucose concentration, even in the presence of the other electroactive species of serum or blood. The electrode is preferably three or four-layered, with the layers serially deposited within a recess upon the tip of a polyamide insulated gold wire. A first glucose concentration-to-current transducing layer is overcoated with an electrically insulating and glucose flux limiting layer (second layer) on which, optionally, an immobilized interference-eliminating horse-radish peroxidase based film is deposited (third layer). An outer (fourth) layer is biocompatible.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 3-8:

This is a Continuation of application Ser. No. 08/299,526, filed Sep. 1, 1994, now U.S. Pat. No. 5,593,852 [which application are incorporated herein by reference, which is a continuation in part of U.S. patent application Ser. No. 08/161,682, filed Dec. 2, 1993, now U.S. Pat. No. 5,356,786, which is a continuation of U.S. Patent Application having Ser. No. 07/664,054, filed Mar. 4, 1991, now abandoned] which is hereby incorporated by reference for all purposes.

AS A RESULT OF REEXAMINATION, IT HAS BEEN DETERMINED THAT:

The patentability of claims 1-3, 52, 53, 64-73, 75-86, 96 and 97 is confirmed.

Claims 5-8, 38, 45 and 46 were previously cancelled.

Claims 32, 33 and 98-100 are cancelled.

Claims 9 and 61 are determined to be patentable as amended.

Claims 10-31, 34-37, 39-44, 47-51, 54-60, 62, 63, 74 and 93-95, dependent on an amended claim, are determined to be patentable.

Claims 4, 87-92 and 101 were not reexamined.

9. An electrochemical sensor for measuring an analyte in an animal, comprising:
one or more analyte responsive electrodes, at least one of said analyte-responsive electrode adapted for subcutaneous implantation in an animal, each of the analyte responsive electrodes comprising
a non-corroding metal or carbon electrode, and
a sensing layer covering at least a portion of each non-corroding metal or carbon electrode, comprising a redox enzyme and a redox compound,
wherein the redox enzyme and redox compound are non-leachable by fluids in the body of the animal at a pH of between about 6.5 and about 7.8; and
one or more alarms, each alarm responsive to a signal generated by the one or more non-corroding metal or carbon electrodes corresponding to an analyte level,
wherein at least one of the alarms is configured to activate if a signal generated at the electrode indicates impending hypoglycemia or impending hyperglycemia; *and further*
*wherein the sensitivity of the sensor does not change by more than about ±5% for 72 hours of operation at 37° C.*

61. [The method of claim 54] *A method of measuring the concentration of a biochemical in an animal comprising:*
*contacting body fluid of the animal with the electrochemical sensor of claim 9 to generate an electrical signal; and*
*determining from the generated electrical signal the concentration of a biochemical in the body fluid,*
wherein the sensor is capable of being calibrated by [the method of claim 52]
*withdrawing a single calibration sample from an animal;*
*assaying an analyte concentration of the single calibration sample;*
*correlating the assayed analyte concentration to a signal generated by one or more implanted working electrodes of an electrochemical sensor to calibrate the electrochemical sensor, each working electrode having an analyte-responsive enzyme disposed thereon; and*
*allowing a predetermined period of time after implantation of the sensor before the signal generated by the sensor is used as an indicator of analyte concentration to the user.*

* * * * *